US012805829B2

(12) United States Patent
Lerner et al.

(10) Patent No.: US 12,805,829 B2
(45) Date of Patent: Nov. 24, 2026

(54) STEERABLE WEARABLE DOPPLER ULTRASOUND VELOCIMETER

(71) Applicant: CorRen Medical, Inc., Minneapolis, MN (US)

(72) Inventors: David Lerner, St. Paul, MN (US); Raymond Paul Oberleitner, Eden Prairie, MN (US); David J. Haskvitz, Maple Grove, MN (US)

(73) Assignee: CorRen Medical, Inc., Minneapolis, MN (US)

( * ) Notice: Subject to any disclaimer, the term of this patent is extended or adjusted under 35 U.S.C. 154(b) by 5 days.

(21) Appl. No.: 19/041,821

(22) Filed: Jan. 30, 2025

(65) Prior Publication Data

US 2025/0248682 A1 Aug. 7, 2025

Related U.S. Application Data

(63) Continuation of application No. 18/794,865, filed on Aug. 5, 2024, now Pat. No. 12,257,102, which is a (Continued)

(51) Int. Cl.
*A61B 8/06* (2006.01)
*A61B 8/00* (2006.01)

(52) U.S. Cl.
CPC .............. *A61B 8/06* (2013.01); *A61B 8/4227* (2013.01); *A61B 8/488* (2013.01)

(58) Field of Classification Search
CPC ......... A61B 8/06; A61B 8/4227; A61B 8/488; A61B 5/02208; A61B 5/026
See application file for complete search history.

(56) References Cited

U.S. PATENT DOCUMENTS

| | | | | |
|---|---|---|---|---|
| 5,363,848 A * | 11/1994 | Spani | A61B 8/06 | 600/455 |
| 6,261,233 B1 * | 7/2001 | Kantorovich | A61B 8/06 | 600/454 |

(Continued)

FOREIGN PATENT DOCUMENTS

EP 4601548 7/2026

OTHER PUBLICATIONS

U.S. Appl. No. 18/794,865, Examiner Interview Summary mailed Dec. 30, 2024, 2 pgs.

(Continued)

*Primary Examiner* — Baisakhi Roy
(74) *Attorney, Agent, or Firm* — Schwegman Lundberg & Woessner, P.A.

(57) ABSTRACT

A wearable Doppler blood flowmeter can be used with an inflatable cuff to measure blood flow, such as for assessing peripheral artery disease (PAD). The present approach can include techniques such as providing or using a wearable acoustic Doppler blood flowmeter, without requiring the intricate manipulation of a handheld Doppler probe. The system can select a pair of acoustic transmitter and acoustic receiver from a set of more than two transducers, including one or more of different locations, orientations, or spacings, such as to vary a targeted region. The RF echo response signal can be translated to an audio response signal. An audio response signal injection circuit can adaptively inject a noise or other enhancement signal, such as to help improve perceptibility of an audible characteristic of pulsatile arterial blood flow. A trained machine learning model can be employed to select or adjust operating settings, to assess diagnostic information, or both.

27 Claims, 34 Drawing Sheets

Related U.S. Application Data continuation of application No. PCT/US2023/034832, filed on Oct. 10, 2023.

(60) Provisional application No. 63/475,032, filed on Oct. 11, 2022.

(56) References Cited

U.S. PATENT DOCUMENTS

| | | | | |
|---|---|---|---|---|
| 7,284,729 | B2 * | 10/2007 | Walsh | A61M 25/02 128/877 |
| 9,685,802 | B1 * | 6/2017 | Mirov | H02J 7/731 |
| 11,462,324 | B1 * | 10/2022 | Roh | G16H 40/40 |
| 12,257,102 | B1 * | 3/2025 | Lerner | A61B 5/026 |
| 2002/0049389 | A1 * | 4/2002 | Abreu | A61B 3/0058 600/318 |
| 2008/0312534 | A1 * | 12/2008 | Pitsillides | A61B 8/06 600/455 |
| 2013/0116663 | A1 * | 5/2013 | Baym | A61B 5/022 604/20 |
| 2014/0221726 | A1 * | 8/2014 | Pilla | A61N 2/006 600/14 |
| 2015/0013111 | A1 * | 1/2015 | White | H04R 1/025 24/3.1 |
| 2016/0120420 | A1 * | 5/2016 | Liedl | A61B 17/1355 600/492 |
| 2017/0172424 | A1 * | 6/2017 | Eggers | A61B 8/488 |
| 2018/0103859 | A1 * | 4/2018 | Provenzano | A61B 5/0024 |
| 2021/0220210 | A1 * | 7/2021 | Berdahl | A61H 7/001 |
| 2022/0237999 | A1 * | 7/2022 | Shelton, IV | A61B 5/7267 |
| 2023/0093814 | A1 * | 3/2023 | Nazer | A61N 7/00 601/2 |
| 2023/0233179 | A1 * | 7/2023 | Warner | A61B 8/06 600/454 |
| 2024/0389976 | A1 * | 11/2024 | Gold | A61B 8/4281 |
| 2025/0114063 | A1 | 4/2025 | Lerner et al. | |

OTHER PUBLICATIONS

U.S. Appl. No. 18/794,865, Non Final Office Action mailed Dec. 3, 2024, 10 pgs.
U.S. Appl. No. 18/794,865, Notice of Allowance mailed Jan. 23, 2025, 9 pgs.
U.S. Appl. No. 18/794,865, Response filed Sep. 20, 2024 to Non Final Office Action mailed Dec. 3, 2024, 12 pgs.
U.S. Appl. No. 18/794,865, Response Filed Nov. 1, 2024 to Restriction Requirement mailed Oct. 28, 2024, 12 pgs.
U.S. Appl. No. 18/794,865, Restriction Requirement mailed Oct. 28, 2024, 7 pgs.
"U.S. Appl. No. 18/794,865, 312 Amendment filed Jan. 31, 2025", 10 pgs.
"U.S. Appl. No. 18/794,865, PTO Response to Rule 312 Communication mailed Feb. 13, 2025", 4 pgs.
"International Application Serial No. PCT US2023 034832, International Preliminary Report on Patentability mailed Apr. 24, 2025", 11 pgs.

* cited by examiner

STEERABLE WEARABLE DOPPLER ULTRASOUND VELOCIMETER

CLAIM OF PRIORITY

This application is a continuation of U.S. patent application Ser. No. 18/794,865, filed on Aug. 5, 2024, which is a continuation under 35 U.S.C. § 111 of and claims the benefit of priority under 35 U.S.C. § 120 to International Patent Application No. PCT/US2023/034832, filed on Oct. 10, 2023, and published as WO 2024/081244 A1 on Apr. 18, 2024, which claims the benefit of priority under 35 U.S.C. § 119(e) to U.S. Provisional Patent Application Ser. No. 63/475,032, filed on Oct. 11, 2022, each of which is incorporated by reference herein in its entirety, and the benefit of priority of each of which is hereby claimed.

TECHNICAL FIELD

This document pertains generally, but not by way of limitation, to medical diagnostics, and more particularly, but not by way of limitation to a steerable beam wearable Stochastic Resonance (SR) Doppler ultrasound velocimeter for assessing blood vessel patency and function.

BACKGROUND

Peripheral Artery Disease (PAD) is a disease of the blood vessels outside of the heart and the brain. PAD is caused by a narrowing of vessels that carry blood to the legs and feet, arms, brain, stomach or kidneys. In PAD, the blood vessel blockages that occur in the arteries can restrict blood flow to the brain, stomach, arms, kidneys, legs and feet. Left untreated, PAD can lead to gangrene and limb amputation. If the blockage occurs in a carotid artery to the brain, it may cause a stroke. Patients with PAD are at heightened risk for death from both heart attack and stroke. PAD can result in poor kidney circulation, which can lead to sudden high blood pressure, or blood pressure that is difficult to control with lifestyle changes and medications. In some cases, blockage of the kidney arteries may progress to loss of kidney function or kidney failure. Diagnosing PAD begins with a medical history and physical examination. A healthcare provider (HCP) may also perform a noninvasive diagnostic test called an ankle brachial index (ABI). The ABI test compares the blood pressure in the upper and lower extremities to look for a decrease in circulation. Specifically, the ABI in each leg is calculated as follows:

$$ABI = \text{(greater of systolic pressure in posterior tibial and dorsalis pedis arteries)/(greater of right and left brachial systolic pressures)} \quad \text{Eq. 1}$$

As determined by relevant standards bodies, an ABI of less than 0.9 is indicative of PAD. PAD severity increases with decreasing ABI values. The measuring of ABI values should include measurements on both lower limbs, but such measurements can be challenging to measure using a handheld Doppler probe.

SUMMARY/OVERVIEW

In an approach to measuring PAD, the systolic pressure in the lower and upper extremity arteries can be measured. A blood pressure cuff is wrapped around the appropriate limb.

A handheld ultrasonic Doppler probe is then placed by a healthcare provider operator against an external location on the subject that is distal to the cuff in such a way as to insonate (expose to ultrasound; also referred to herein as "insonify") the target artery (e.g., posterior tibial artery). The handheld Doppler probe may be connected via a cable to an electronics unit that is not handheld, but which can be located on a cart or elsewhere. The handheld Doppler probe is carefully moved by the healthcare provider operator over the skin until the healthcare provider can discern a characteristic audio and/or visually based arterial pulse signal, according to the Doppler effect. Once this characteristic audio signal is discerned by the healthcare provider operator, the blood pressure cuff is inflated until the Doppler audio signal can no longer be discerned by the healthcare provider operator. This will occur when the cuff pressure of the blood pressure cuff exceeds the peak systolic pressure in the target artery. Once this is achieved, the blood pressure cuff is slowly deflated. When the cuff pressure decreases to a point that is just below the peak systolic pressure, the Doppler shift audio and/or visual signal will reappear so as to be discernable by the healthcare provider operator. At this point, the pressure in the cuff will be approximately equal the peak systolic pressure in the artery. This is somewhat similar to an auscultatory approach for measuring brachial systolic pressure, except that this approach uses a handheld ultrasonic Doppler probe in place of a stethoscope. In addition to measuring blood pressures, a spectral waveform against time may be created using data from the handheld ultrasonic Doppler probe. This spectral waveform against time will have an amplitude that is proportional to blood flow velocity. This spectral waveform against time may be used by a healthcare provider operator to evaluate a degree of the occlusion of the blood vessel, such as by evaluating a morphology of the waveform.

One challenge with this approach using a handheld ultrasonic Doppler probe is that the healthcare provider operator must first locate a target artery in the lower extremity using the handheld ultrasonic Doppler probe. But these handheld probes have a limited focal range (e.g., limited minimum depth, limited maximum depth, and limited beamwidth). Therefore, such a probe can only be used to discern a blood flow signal when the target blood vessel is located within these ranges so as to be adequately exposed to the handheld Doppler probe beam. Practically, the healthcare provider operator must first apply acoustic coupling gel to the target limb, to the handheld probe, or to both. Applying the acoustic coupling gel can help to provide good impedance matching between the Doppler probe and the patient for insonifying a target region and observing a response signal from the target region. The healthcare provider operator must then carefully orient and manipulate the handheld Doppler probe to bring the focal zone of the handheld Doppler probe's ultrasonic field close to the artery. This can be accomplished by moving the handheld Doppler probe over the skin of the subject near where the target artery is expected to be (e.g., based on surface anatomy markers) or by palpating for a pulse and listening for an audio signal output from the handheld Doppler probe indicative of the Doppler shift frequency relating to blood flow velocity. This handheld Doppler probe audio signal output amplitude may be lower than the background noise that results from the system electronics (e.g., thermal noise, intermodulation distortion products, etc.) and because of weak ultrasonic signals such as can be due to variable patient anatomy, patient body habitus, obesity, edema, or the like. This can render this approach (e.g., moving the handheld Doppler probe and listening for a characteristic audio signal) too difficult to perform on a practical basis—particularly for a healthcare provider operator with insufficient or no training.

When moving the handheld Doppler probe about a target exterior location of the patient, the healthcare provider operator must also change the angle between the long axis of the handheld Doppler probe and the skin surface to ensure that there is an acute angle and also to bring the focal zone of the Doppler probe close to the target blood vessel of interest. The need for an acute angle is because the Doppler frequency shift is related, in part, to the cosine of the angle between the axis of symmetry of the ultrasonic field and the blood velocity vector. This action of adjusting the angle of the handheld Doppler probe can be very challenging, time consuming, and often not feasible. For example, if the target artery is outside the focal zone of the handheld Doppler probe, the above-described approach will not be able to capture the blood flow signal.

A further complication of the above-described approach of using a handheld Doppler probe is that the ultrasonic field is attenuated as it penetrates the body. Lower frequency ultrasonic fields are able to penetrate into the body with less attenuation than higher frequency ultrasonic fields. For a patient with a larger body habitus, the target artery may be located deeper than for a patient with a smaller body habitus. For this reason, the above-described approach may need to employ multiple, separate handheld Doppler probes with different ultrasound insonification frequencies (e.g., 4 MHz for relatively deeper arteries and 8 MHz for relatively superficial arteries). The healthcare provider operator can attempt to capture the blood flow signal using the second handheld Doppler probe if unsuccessful with the first handheld Doppler probe.

In yet another complication for the healthcare provider operator using the above-described approach, acoustic coupling gel ("acoustic couplant") is applied between the handheld Doppler probe surface and the skin. The acoustic coupling gel can help to match acoustic impedances between the handheld Doppler probe and skin of the patient or subject. Without this acoustic couplant, virtually no blood flow signal can be discerned using the above-described approach. As the healthcare provider operator moves the handheld Doppler probe across the skin of the subject to try and locate the target artery, the gel couplant is often moved as well, so that more gel must then be applied. Further, audio static-noise is created by this handheld Doppler probe movement. Such audio static-noise can be distressing to the patient, can be distracting to the healthcare provider operator, or both. Such audio static-noise also may obscure the audio signal carrying the blood flow information that the healthcare provider operator is trying to discern.

All these factors (e.g., focal zone range limitation, acoustic field frequency, patient body habitus, gel application, etc.) can limit the use of the above approach in general clinical practice. The challenges of locating the target artery are such that significant training of the healthcare provider operator is needed for successful use of Doppler ultrasound using the above-described approach. While it is also possible to use an oscillometric approach for measuring blood flow and computing an ankle-brachial index (ABI), such an oscillometric approach may be susceptible to a high degree of oscillometric errors, and the oscillometric readings may be challenging to interpret, such as for determining ABI. Further, oscillometry cannot discern the blood pressure in an individual blood vessel, while a Doppler system can. This means that oscillometry may only produce a (somewhat error prone) pressure reading associated with a limb, rather than a blood pressure of a specific artery. For diagnosing PAD, among other things, it is desirable to obtain measurement of pressures and ABIs in specific arteries rather than bring limited to the limb as a whole.

The present document relates to systems and methods for assessing the patency and functionality of various body structures, such as blood vessel patency of blood vessels. For example, the present approach can be used for diagnosing peripheral arterial disease (PAD), among other things. This can include using a unique physiological continuous wave (CW) Doppler ultrasound device—such as which can be affixed to the subject rather than handheld—to measure the ankle brachial index (ABI), to interpret the blood velocity waveform morphology in the ankle (e.g., posterior tibial and dorsalis pedis) and upper extremity (e.g., brachial) arteries, or both, such as explained herein.

The present approach, which can include using Stochastic Resonance (SR) can be referred to herein as "Doppler-SR". The present approach can potentially help address one or more challenges of above-described handheld Doppler probe approach, such as in one or more of the following ways:

1. Allows automatic focusing of one or more ultrasonic fields, such as to insonate target blood vessels without requiring clinician or healthcare provider operator intervention, which can help simplify determining ABI and other testing processes;
2. Allows measuring and perceptible discernment of very small amplitude ultrasound-derived blood flow signals, such as by using stochastic resonance ("SR") or one or more other methodologies such as described herein;
3. Allows automatic tuning of system electronics for individual ones or for each of multiple ultrasonic fields, such as to help optimize signal quality;
4. Allows preventing cross contamination from one patient to another by providing a wearable disposable appliance for affixing the Doppler probe to the patient's body; or
5. Helps reduce or minimize the need for applying, manipulating, and removing acoustic gel couplant, which would otherwise be required in other approaches.

The present techniques can help provide a system that, when applied to PAD diagnosis, can have both high sensitivity, which can help yield reduced false negative PAD determinations compared to certain other approaches, and high specificity, which can help yield reduced false positive PAD determinations compared to certain other approaches.

A primary challenge for a healthcare provider operator, in using a handheld Doppler ultrasound probe, is locating a blood vessel (e.g., an artery) and discerning a Doppler shift audio or visual signal indicating blood flow. This challenge can be caused by, among other things: the limited focal range of a handheld Doppler ultrasound probe; the use of a handheld Doppler ultrasound probe having ultrasonic fields with multiple points of nullity; attenuation of ultrasonic signals at deeper body structures; excessive signal attenuation by the processing electronics; acoustic impedance mismatches at various boundaries; low blood flow states (such as can be associated with PAD or other disease); variable patient anatomy (e.g., artery location relative to surface anatomy); or the like.

The present Doppler-SR approach can be helpful to address one or more of these challenges. The present Doppler-SR approach can incorporate multiple ultrasonic piezoelectric or other elements, such as to perform as a transmitter or a receiver of an ultrasonic field. Adding even a single additional piezoelectric transducer (PZT) element to a two-element Doppler probe can help increase both the focal longitudinal and transverse ranges of the Doppler probe. This can help enable the more-than-two element Doppler probe to register blood vessels more easily than a two-element system, such as explained further herein.

Further, in the present Doppler-SR approach, one or more of these PZT ultrasound elements can be included within a wearable carrier that can be affixed to a subject at a desired location. In this way, the one or more of these PZT ultrasound elements can be moveable with respect to subject (and with respect to a portion of the carrier that is affixed to the subject). Thus, with the carrier in place against the subject, the one or more of these PZT ultrasound probes can be moved across the surface of the skin, such as explained further herein. Such movement of the probe can be guided or otherwise facilitated by the wearable carrier.

Additionally or alternatively, a location or a relative angle of an individual one, of more than one, or of each one of the PZT elements can be adjustable with respect to the subject, such as after the carrier has been affixed to the subject (e.g., manually or automatically, either or both of which can be carried out mechanically, electronically, or both). Automatic selection or adjustment of a location or orientation of a PZT transducer element carried by a wearable device that can be adhered or otherwise secured to a limb of a patient can help enable complete insonation and interrogation of a target volume without requiring user-manipulation for changing a handheld probe-vessel angle or a handheld probe position. The present approach can help enable focusing the ultrasonic field on one or more target blood vessels regardless of a location of the target blood vessel within the body. Additionally or alternatively, ultrasonic field expansivity can be attained by addressing or exciting different ultrasound transducer elements (e.g., in an array or other arrangement) either separately, or in combination. This can help enable locating an ultrasonic field at different locations within the subject, such as when the carrier is affixed to the subject, even without requiring any physical movement of the ultrasonic element. This, in turn, can help ease the task of locating and measuring blood flow in the target blood vessel.

The PZT ultrasound transducer elements can be mounted onto a semi-rigid electromechanical carrier structure. The carrier structure can include one or more of an electrical, mechanical, or electromechanical actuator that can allow for selectively addressing, positioning, or both, of one or more individual PZT ultrasound transducer elements. This can help enable translocation or angulation, or both, of one or more individual PZT ultrasound transducer elements. As explained in more detail herein, the carrier can include a movable housing or stage carrying one or more of the individual PZT ultrasound transducer elements. This can help allow positioning or movement of an individual PZT ultrasound transducer element with respect to the subject when the carrier is affixed to the subject. For example, the movable stage can include a disk-shaped structure ("disk"). The disk can be actuated to rotate about at least one axis, and optionally, to rotate about each of two axes, such as which can be orthogonal to each other. The disk can be configured to rotate using one or more threads, such that rotating the disk adjusts a skin offset distance of at least one of the acoustic transmitter or the acoustic receiver with respect to the skin of the subject. The disk-shaped movable stage structure can be actuated by an electrical micro-motor. The micro-motor can be powered by an on-board battery. The battery can also be carried by the carrier. The battery need not be located on the movable stage portion of the carrier. The on-board battery can be chargeable or re-chargeable using either a wired or wireless (e.g., inductive) coupling for performing the charging or re-charging. Processing circuitry can also be included on the carrier. The processing circuitry can control charging or re-charging of the battery, operation of the PZT transducer elements, or both, and can be configured to provide communications or other functionality as well. The processing circuitry can be communicatively coupled to a local or remote user interface, such as via a Bluetooth transceiver connection to a local computer or mobile smart-phone or the like.

The ultrasound transducer elements may be mounted on the disk-shaped or other movable stage on the carrier, such as in one or more of a rectangular (x-y), circular, spiral, linear, or other arrangement. For example, the PZT ultrasound transducer elements can be mounted on concentric circular rings. Individual rings can be configured to rotate independently with respect to the portion of the carrier that is affixed to the subject. This can help allow for pairing (or otherwise selectively combining) operation of various individual PZT ultrasound elements, such as can be of or in different geometries, dimensions, or both, thus permitting or facilitating insonating different anatomic locations within the subject. For example, an acoustic transmitter element can be paired with one or more acoustic receiver elements.

The disk carrying the individual PZT ultrasound elements can also include an acoustic impedance matching substance. For example, the disk can be contained within a fluid-filled (e.g., oil-filled) reservoir that can be sealed. The Doppler probe including the fluid-filled reservoir and the disk carrying the individual PZT ultrasound elements can be referred to as a Doppler-SR probe. A significant potential advantage of the present Doppler-SR probe approach is that moving the one or more PZT ultrasound elements relative to the skin of the subject need not require any moving a location of actual physical contact between the PZT ultrasound element and the skin. Therefore, the present Doppler-SR approach need not involve any resulting friction between the Doppler-SR probe surface and the surface of the skin of the subject, which would otherwise result in audio static-noise.

For example, the Doppler-SR probe can include various layers (and boundaries between layers) that, starting with the PZT ultrasound elements and moving in a direction toward the target artery of interest, can include: (1) the PZT ultrasound element; (2) an acoustic impedance matching fluid or substance; (3) a reservoir surface; (4) an acoustic impedance matching gel pad; (5) the skin of the subject; (6) sub-dermal tissue of the subject; and (7) the target artery for which a blood flow characteristic is to be determined. This arrangement can help allow for moving the ultrasonic fields with respect to the target region of interest, without producing the associated static-noise that would be encountered by a handheld Doppler probe being slid along a gel-coated skin surface of the subject. As mentioned, such static-noise can obscure the audio signal that the health care provider operator is trying to discern, and can cause stress or anxiousness for the patient when heard by the patient.

Additionally or alternatively, the individual PZT ultrasound transducer elements can be configured to provide different insonation center frequencies. This can help with measuring a blood flow characteristic of both deep and superficial target blood vessels. This is because higher frequency ultrasound is more attenuated than lower frequency ultrasound as the ultrasound waves penetrate the body tissue.

Certain clinical and anatomic conditions may lead to very small Doppler-shifted audio response signal amplitudes. Accordingly, the present inventor has recognized that there is a need to be able to augment or enhance such a small-amplitude Doppler-shifted audio response signal. Such augmentation or enhancement can help allow for a healthcare provider operator or a device performing a detection algorithm to register or discern such a small-amplitude Doppler-shifted audio response signal. The present Doppler-SR system can employ an approach for augmenting or enhancing the small-amplitude Doppler-shifted audio response signal, such as to make it easier to register or discern.

For example, the present Doppler-SR system can include an audio response enhancement signal injection circuit. The audio response enhancement signal injection circuit can be configured to vary at least one of an amplitude or bandwidth of an audio response enhancement signal. The variable audio response enhancement signal can be combined with the audio response signal to make it easier to register or discern. For example, the audio response enhancement signal can include at least one of a carrier signal, a noise signal, or a tone signal to help enhance the audio response signal for audio playback to a user of the system.

For example, the audio response signal can be enhanced based on stochastic resonance. Stochastic resonance allows a sub-detection-threshold signal to be enhanced, such as by adding an audio response enhancement signal that includes noise of sufficient amplitude. Such enhancement can thereby result in a non-zero Doppler-SR sensor output signal that is discernable to the user or algorithm using the Doppler-SR sensor to evaluate blood flow in a target vessel. Further, if the input Doppler-SR sensor audio response signal amplitude changes over time, the optimal noise level for enhancing the audio response signal can be estimated and can be established or adjusted, such as in a feedback loop, such as in a manner that can be based upon a resonance curve. For example, a variable bandwidth noise signal (e.g., including at least one of white, brown, or pink noise) can be added to the Doppler-shifted baseband audio response signal that is obtained in response to insonation of a target region of interest. White noise includes similar noise components at all (human) audible frequencies. Brown noise is more attenuated at lower audible frequencies than at higher audible frequencies. Pink noise is more attenuated at higher audible frequencies than at lower audible frequencies. Because the Doppler baseband audio response signal is always within the frequency range of human hearing, a "white noise" signal is likely to contain some overlapping frequencies. Thus, enhancing the Doppler baseband audio response signal by adding in a white noise signal can help render the Doppler baseband audio response signal perceivable to a healthcare provider operator or to an algorithm-enabled device. Once a perceivable Doppler baseband audio response signal is attained, one or more other characteristics of the Doppler-SR system may be employed, such as to help increase the signal amplitude of the enhanced Doppler baseband audio response signal.

Additionally or alternatively, to help locate initial placement of the wearable carrier component of the present system, a separate or integral microphone can be included and used to detect and discern an arterial pulse. This "electronic stethoscope" approach can be used to listen for an indication of blood flow indicating the presence of a target vessel. Using information obtained by such listening, the healthcare provider or other user can adjust a location or other attribute of a harness of the wearable carrier. For example, this can be performed such as to help center or otherwise appropriately position the Doppler-SR probe to help ensure that the various ultrasonic fields that can be created by the Doppler-SR probe are likely to intersect with the target blood vessel.

Additionally or alternatively, to help increase or maximize signal integrity, the present Doppler-SR probe system can include a tuned or tunable circuit. For example, the tuned or tunable circuit can be used to help amplify the raw piezoelectric Doppler-shifted audio response signal emanating from one or more of the PZT ultrasound transducer receiver elements, as explained herein. In addition, a transformer-coupled interface can be included between the PZT ultrasound transducer receiver element and an audio response signal amplifier, such as to help ensure maximum power transfer therebetween. The tuned or tunable circuit can be arranged with the transformer-interface such that the tuned or tunable circuit can include a capacitor. The capacitor in the tuned or tunable circuit can be arranged in parallel with a secondary coil of the transformer. In this way, a resonant frequency of the transformer secondary coil inductance paired with the tuning capacitor can be made equal to a center frequency of the insonation signal providing the ultrasonic field. To help ensure that this can always be at or near an optimal match, an electronically-tuned capacitor (e.g., varactor diode) can be used, such as to electronically tunably adjust the capacitance value of the capacitor, such as before each use or as needed.

This Summary/Overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, systems, methods, and other techniques that can help provide an easier way of measuring a blood flow characteristic in a target blood vessel, such as for assessing peripheral artery disease (PAD) of a subject. The present approach can include techniques such as providing or using a wearable acoustic Doppler blood flowmeter. The wearable acoustic Doppler blood flowmeter can include one or more features for at least one of insonifying a region of interest, locating a target blood vessel, providing assistance or automaticity in acquiring a blood flow signal from the target blood vessel, or providing an audible or visual indicator to a user of the system, such as to help in discerning the Doppler-shifted blood flow signal or to help in evaluating a PAD characteristic or other physiological characteristic. The present techniques can include or be used together with an inflatable cuff. The present techniques need not require the experience and training needed for successfully performing an alternative approach that would involve intricate manipulation of a handheld Doppler probe. For example, the system can include an audio response signal injection circuit, such as can vary at least one of an amplitude or a bandwidth of an audio response enhancement signal. The audio response enhancement signal can be combined with an audio response signal that is generated in response to Doppler insonification of the target region. Examples of the audio response enhancement signal can include at least one of a carrier signal, a noise signal, or atone signal, such as which can be summed, superpositioned onto, or otherwise combined with an audio response signal for audio playback to a user of the system, such as explained in more detail herein.

Figure 1:
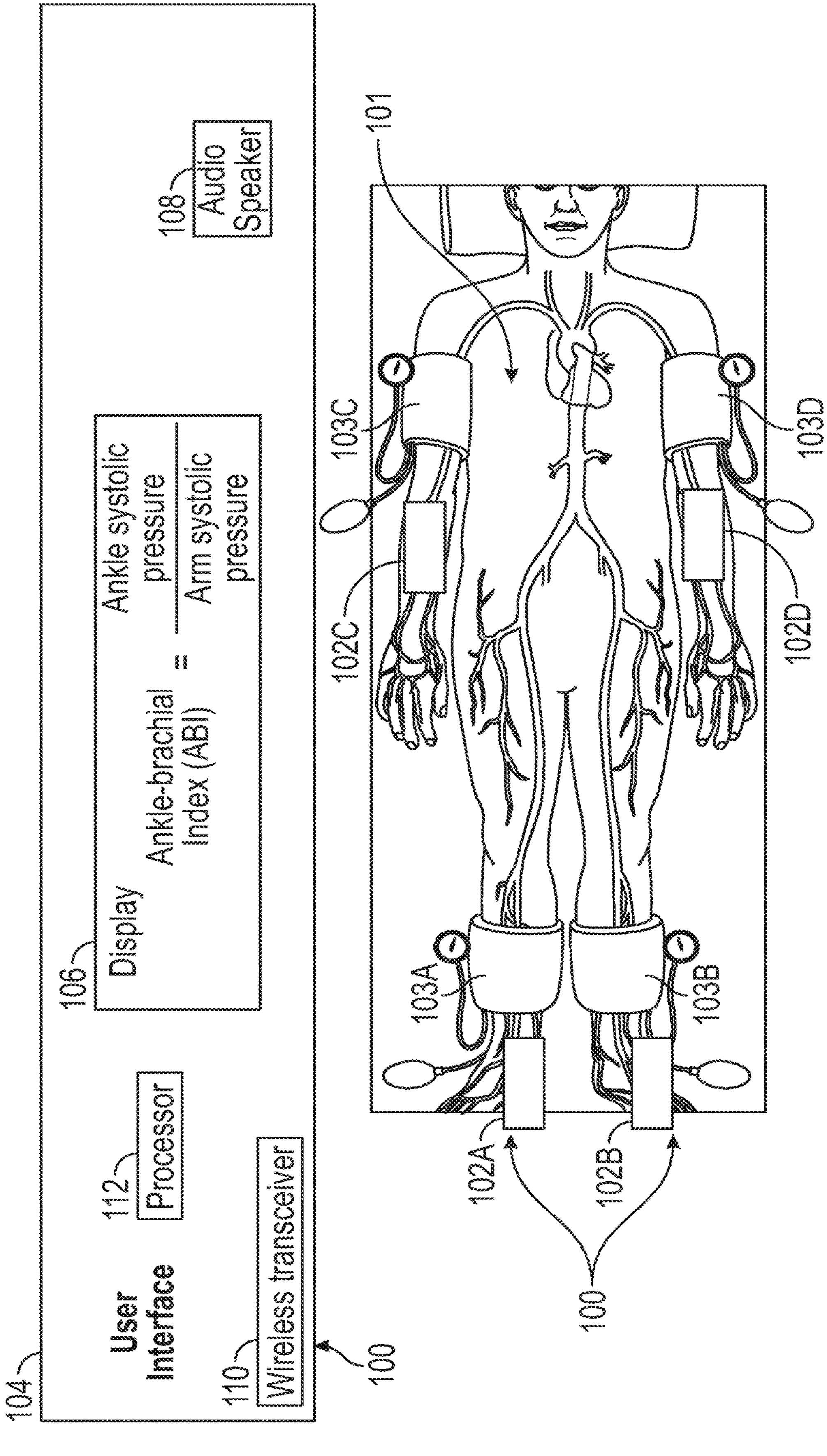
FIG. 1 is a schematic diagram illustrating an example of portions of the present Doppler-SR system and portions of an environment in which it can be used, such as for measuring ankle and arm systolic blood pressures for diagnosing the ankle brachial index (ABI) of a subject, such as for assessing Peripheral Artery Disease (PAD).

FIG. 1 is a schematic diagram illustrating portions of the present Doppler-SR system 100 and portions of an environment in which it can be used. For example, such uses can include measuring ankle and arm systolic blood pressures. Such measured blood pressure can be used for diagnosing the ankle brachial index (ABI) of a subject 101, such as for assessing Peripheral Artery Disease (PAD). In FIG. 1, the system 100 can include inflatable cuffs 103A-D. The inflatable cuffs 103A-D can be respectively worn on different individual limbs of the subject 101. Each of the inflatable cuffs 103A-D can be inflated and deflated, such as by a healthcare provider operator or upon receiving an electrical command signal from processor or controller circuitry. Also, each of the inflatable cuffs 103A-D can include a corresponding inflation pressure sensor. This can permit reading a measurement of the inflation pressure of the corresponding inflatable cuff 103A-D. For example, a Doppler flow measurement signal can be acquired from a target blood vessel on the limb at a location that is distal to the inflatable cuff 103A-D. The inflation pressure sensor of the inflatable cuff 103A-D can be used to record the inflation pressure of the inflatable cuff 103A-D, such as at which the corresponding Doppler flow measurement signal appears or ceases.

The present system 100 can include wearable carriers 102A-D, such as for carrying one or more Doppler ultrasound flow transducers and associated componentry. An individual one of the wearable carriers 102A-D can be worn on a limb of the subject 101, such as at a location that is distal to the corresponding individual ones of the inflatable cuffs 103A-D worn by the subject 101 on that same limb. The wearable carrier 102A-D can include a sleeve, a strap, or other affixation device for holding or affixing the carrier 102A-D at the desired location. The wearable carrier 102A-D can be sized, shaped, or otherwise configured to allow placement and affixation at the target location. Thus, the carriers 102A-B can be sized, shaped, or can otherwise be configured for being placed and affixed at or near respective ankles of the subject 101, such as to locate their corresponding Doppler probes at or near a posterior tibial artery or at or near a dorsalis pedis artery. The carriers 102C-D can be sized, shaped, or otherwise configured for being placed and affixed at or near respective elbows of the subject 101, such as to locate their corresponding Doppler probes at or near a brachial artery of the subject 101. By providing wearable carriers 102A-D that can be affixed to a respective limb of the subject, and that carry onboard Doppler probes, the more complicated use of a handheld Doppler probe—which involves careful positioning and manipulation by a well-trained user to acquire a suitable blood flow signal from a target artery—is not required and can be avoided. The wearable carrier 102A-D can be separate from or integrated with the corresponding inflatable cuff 103A-D that is to be placed or worn on the same limb.

An individual one of the wearable carriers 102A-D can include an electronics unit and one or more ultrasound or other acoustic transducers, such as to provide one or more corresponding Doppler flow probes attached to the wearable carrier 102A-D. The electronics unit of an individual wearable carrier 102A-D can include controller or processor circuitry, such as a microcontroller or a microprocessor. The processor circuitry can be configured for controlling operation of the corresponding Doppler flow probe such as by determining and providing one or more control signals. The one or more control signals provided by the processor circuitry can be used to adjust an orientation, position, or other characteristic of an ultrasound field from the Doppler flow probe insonating a target area, such as a target area in which a target blood vessel can be located. The controller or processor circuitry of an individual wearable carrier 102A-D can include signal processing circuitry, such as for processing a resulting Doppler-shifted response signal from the subject 101. An individual wearable carrier 102A-D can include wired or wireless communication circuitry, such as for communicating with a wired or wireless transceiver 110 of a local or remote user interface device 104, for example, using a Bluetooth wireless communication signal or the like. A carrier 102 can also optionally include an electrical, chemical, or other heating element, such as which can optionally be controlled by a controller to provide localized heating to the target region of the subject, such as to help promote vasodilation.

The user interface 104 can also include one or more of processor 112 circuitry, a display 106, and an audio speaker 108. The processor 112 can include stored instructions that, when performed by the processor 112, can allow the processor 112 to compute an ankle-brachial index (ABI). The ABI can represent a comparison between (1) the blood pressure at the arms of the subject 101 to (2) the blood pressure at the ankles of the same subject 101. The ABI can be displayed to the healthcare provider operator or other user on the display 106. The audio speaker 108 can be used to play an audible audio Doppler-shifted signal acquired by one or more Doppler probes associated with one or more of the carriers 102A-D that are affixed to the subject 101. The system can optionally be configured such that the speaker operates in a quieter first mode until a Doppler blood flow signal is detected. The processor circuitry can be configured to increase a volume of the audible signal provided by the speaker when a Doppler blood flow signal characteristic of arterial blood flow has been detected by the processor circuitry.

Figure 2:
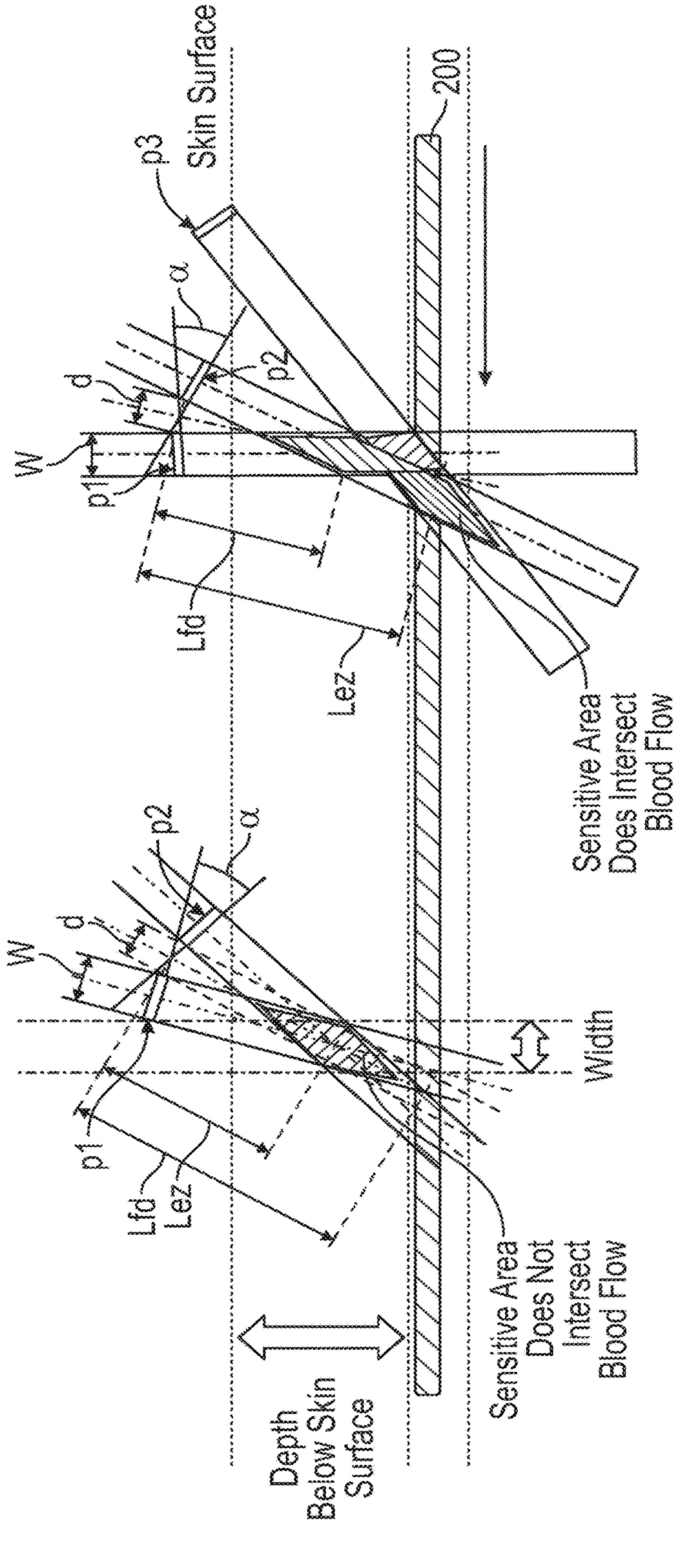
FIG. 2 is a schematic illustration illustrating conceptually the advantages of using multiple Doppler ultrasound transducer elements for obtaining more flexibility in insonating and measuring blood flow information from a particular target blood vessel.

FIG. 2 is a schematic illustration illustrating conceptually the advantages of using multiple Doppler ultrasound transducer elements for obtaining more flexibility in insonating and measuring blood flow information from a particular target blood vessel 200. For a particular patient, the blood vessel 200 is located at an unknown depth below the skin surface of the patient. The left portion of FIG. 2 shows an arrangement of Doppler piezoelectric transducer elements p1 and p2. One of the piezoelectric transducer elements p1 and p2 can be configured to operate in a transmit mode as an ultrasound transmitter such as to transmit acoustic energy at an acoustic radiofrequency (RF). The other of the piezoelectric transducer elements p1 and p2 can be configured to operate in a receive mode as an ultrasound receiver such as to receive an acoustic radiofrequency (RF) response signal. The piezoelectric transducer elements p1 and p2 can be configured (or re-configured) to operate in either one of the transmit mode or the receive mode.

For example, the piezoelectric transducer element p1 can be configured to operate as an ultrasound transmitter, defining an insonation transmit beam having a longitudinal central axis extending orthogonal to a central location on the piezoelectric transducer element p1, having a lateral insonation transmit beamwidth "w" orthogonal to the longitudinal central axis of the insonation transmit beam being provided by p1, and having an effective insonation transmit depth below the skin surface that depends on a frequency of the insonation transmit signal provided by p1. The piezoelectric transducer element p2 can be configured to operate as an ultrasound receiver, defining an insonation receive beam having a longitudinal central axis extending orthogonal to a central location on the piezoelectric transducer element p2, having a lateral insonation receive beamwidth "w" that is orthogonal to the longitudinal central axis of the insonation receive beam corresponding to p2, and having an effective insonation receive depth below the skin surface that depends on an insonation receive frequency for which p2 is configured.

Although the transmit and receive beams are shown in FIG. 2 (as well as in other the other FIGS. in this document) as being rectangular as drawn, this is for conceptual ease of illustration in a two-dimensional drawing. It is understood that acoustic beams will occupy a volume, and that the volume will spread out (diverge) and attenuate during travel from source to destination, whether being transmitted by a transducer or reflected back as an echo response signal that is being received by a receive transducer.

Using this combination of p1 in transmit mode and p2 in receive mode, an area or volume of intersection between the insonation transmit beam and the insonation receive beam can be defined. This area or volume of intersection is the effective area from which blood flow information can be acquired. But as seen in the left portion of FIG. 2, this area or volume of intersection does not intersect the target blood vessel 200. Thus, the arrangement shown on the left portion of FIG. 2 is not sensitive to blood flow in the target vessel 200.

The right hand portion of FIG. 2 illustrates the addition of a similar third ultrasound transducer element p3. The ultrasound transducer element p3 can be located and oriented to define an area or volume of intersection with one or both of the piezoelectric transducer elements p1 and p2 that does also intersect with the target blood vessel 200. Thus, by configuring p1 in transmit mode and p3 in receive mode (or vice-versa), the arrangement shown in the right hand portion of FIG. 2 can be useful for obtaining blood flow information from the blood vessel 200. In sum, (1) adding one or more additional piezoelectric transducer elements (e.g., using any number of transducer elements beyond 2, as space and cost allow), and (2) configuring a controller to control operation of various permutations or combinations of piezoelectric transducer elements (e.g., in transmit mode, in receive mode, or off), can help allow additional flexibility for detecting blood flow in a target blood vessel located at an unknown depth. The configuration of more than two piezoelectric transducer elements may be static or may allow movement of one or more of the piezoelectric transducers. In a static arrangement, the controller or processor 112 can be configured to selectively address various ones of the piezoelectric transducers, such as in a desired one of a transmit mode or a receive mode, to permit an effective transmit and receive insonation intersection area that overlaps with the target blood vessel from which blood flow is to be detected. Such selective addressing can also be used with a moveable arrangement, either before or after actuating a physical movement of at least one of the transducers, which can also be controlled by the controller or processor 112. The controller or processor 112 can also select a combination of particular transducers having compatible transmit and receive frequencies for use together. Providing more than two piezoelectric transducers (e.g., from which two can be selected as a transmit transducer and a receive transducer, respectively), can also allow selection or re-configuration of the transducers being used in such a manner so as to help avoid null areas of low sensitivity (e.g., near-field Fresnel zone) that can sometimes otherwise be present in a two-transducer CW Doppler arrangement. For example, two transducers can be selected by the processor 112 from a set of more than two transducers (e.g., 3, 4, 5, 6, . . . , 12, or even more transducers) to provide an insonation intersection region that also intersects the target blood vessel 200 of interest. In situations where multiple transducer pairs can provide such an insonation intersection region that also intersects the target blood vessel 200 of interest, a transmit and receive transducer pair can be selected that has maximum sensitivity at the insonation intersection region, or that has consistent sensitivity (e.g., relatively fewer or no nulls) at the insonation intersection region. The nulls occur in what is called the “near field” or “Fresnel zone.” The shape of this near field region is defined by the shape or dimensions of the crystal piezoelectric transducer and its frequency of operation. For example, for a circular crystal piezoelectric transducer of radius R operating at frequency f where the speed of ultrasound in tissue is C, the near field ends at a distance (from the crystal face of the transducer) d=(R^2)*f/C. The formula may differ with transducer shape, size, or both, so that the formula may be somewhat different for a rectangular crystal. It may be desirable to locate the intersection zone to be just beyond this distance d (i.e., in the near part of the far field region).

Figure 3:
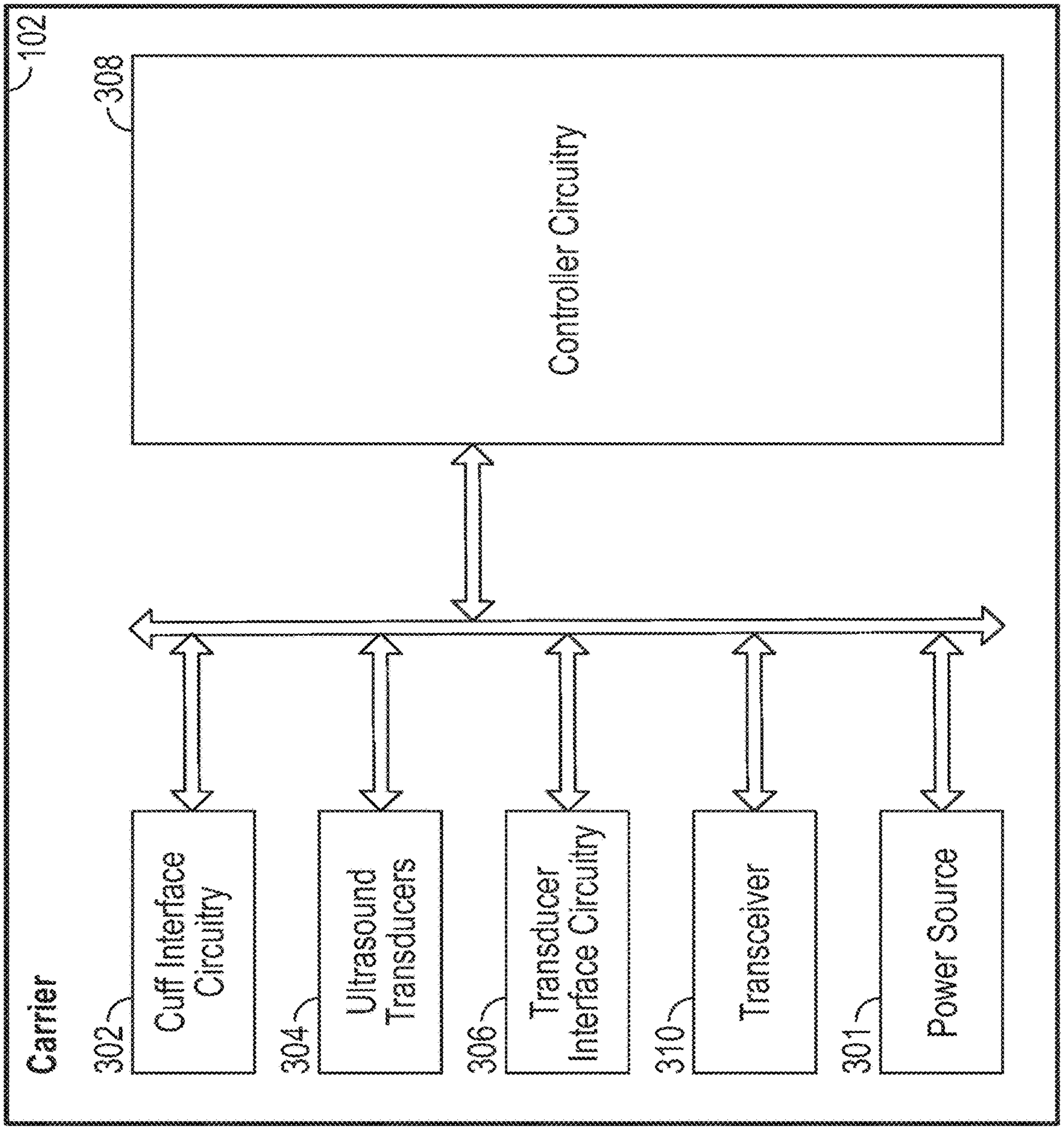
FIG. 3 is a schematic block diagram example of portions of the wearable carrier, such as the carriers shown in FIG. 1.

FIG. 3 is a schematic block diagram example of portions of the wearable carrier 102, such as the carriers 102A-D shown in FIG. 1. The wearable carrier 102 can include a sleeve, a strap, or other affixation device for holding or affixing the carrier 102A-D at the desired location, such as described elsewhere herein. The carrier 102 can also include controller circuitry 308, which can include microcontroller or microprocessor circuitry. The controller circuitry 308 can include memory circuitry, which can include programmable or other stored instructions. When such instructions are performed by the controller circuitry 308, the controller circuitry 308 can perform methods such as described herein. The controller circuitry 308 can include other hardware, software, or firmware, such as which may be configured to provide signal processing circuitry for performing signal processing, such as described herein. The controller circuitry 308 can be electrically connected or otherwise coupled, such as via one or more buses, to other circuitry or componentry located on the carrier 102. Processing performed by the controller circuitry 308 can be offloaded to the processor 112 for being performed there, or vice-versa.

Cuff interface circuitry 302 can be included in or coupled to the controller circuitry 308. The cuff interface circuitry 302 can include a cuff pressure input that can be coupled to a corresponding inflatable cuff 103, such as to receive an electrical or other cuff pressure signal from a pressure transducer located with the inflatable cuff 103. The cuff interface circuitry 302 can also include a cuff inflation output that can provide an electrical or other cuff inflation signal to the inflatable cuff 103 such as for controlling or actuating inflation and deflation of the inflatable cuff 103. Cuff pressure information, cuff pressure control information, or both can be communicated to a transceiver 310 located on the carrier 102, such as via the controller circuitry 308 or otherwise. The transceiver 310 can communicate such information with a corresponding transceiver 110 of the user interface 104, such as for signal processing by the processor 112 of the user interface 104 or for display by the display 106 of the user interface 104. Regardless of whether processing steps are described herein as being performed by the processor 112 on the user interface 104 or by the controller 308 of the carrier 102, it is understood that the location of such processing steps being performed can be interchanged, such as to offload processing from the controller 308 to the processor 112, or vice-versa.

The carrier 102 can also include acoustic transducers such as ultrasound transducers 304. The ultrasound transducers 304 can be configured or configurable or re-configurable to operate in transmit mode, to insonify a target region, or in receive mode, to receive ultrasound energy from an insonified target region in the patient, such as at a depth beyond a skin surface of the patient against which the ultrasound transducer 304 or a coupling element is provided. In an example, the ultrasound transducers 304 can include two ultrasound transducers 304, arranged to define an intersecting target region in the patient from which ultrasound information can be acquired in response to insonation of the target region. In another example, the ultrasound transducers 304 can include more than two transducers, such as 3, 4, 5, 6, 7, 8, 9, 10, 11, 12, 13, 14, 15, 16 or even more transducers 304, such as which can be arranged in one or various fixed or variable orientations with respect to each other, and selectively actuated or located in a desired pair, permutation, or combination. As described herein, by using additional transducers 304 beyond two, by providing variable locations or orientations of such transducers 304, or by appropriate selecting of a particular pair, permutation, or combination of transducers 304, or by additionally or alternatively selecting an appropriate transmit or receive mode frequency, additional flexibility can be obtained for obtaining the desired blood flow information from the target region location. This, in turn, can make it easier to establish a target region location that intersects with a blood vessel of interest, such as for determining blood flow in such a blood vessel.

The carrier 102 can include transducer interface circuitry 306, such as for selecting, powering, enabling, operating, moving, or otherwise controlling the ultrasound transducers 304. The transducer interface circuitry 306 can also be configured to receive one or more electrical signals transduced from one or more of the ultrasound transducers 304. The transducer interface circuitry 306 can also be configured to perform signal processing or pre-processing, such as for ultrasound signals being further communicated to at least one of the controller circuitry 308 on the carrier 102 or (via the transceiver 310) by the processor 112 circuitry located on the local or remote user interface 104. The carrier 102 can also include a battery or other power source 301, such as for providing electrical power to electronic circuitry included in an electronics unit of the carrier 102.

Figure 4:
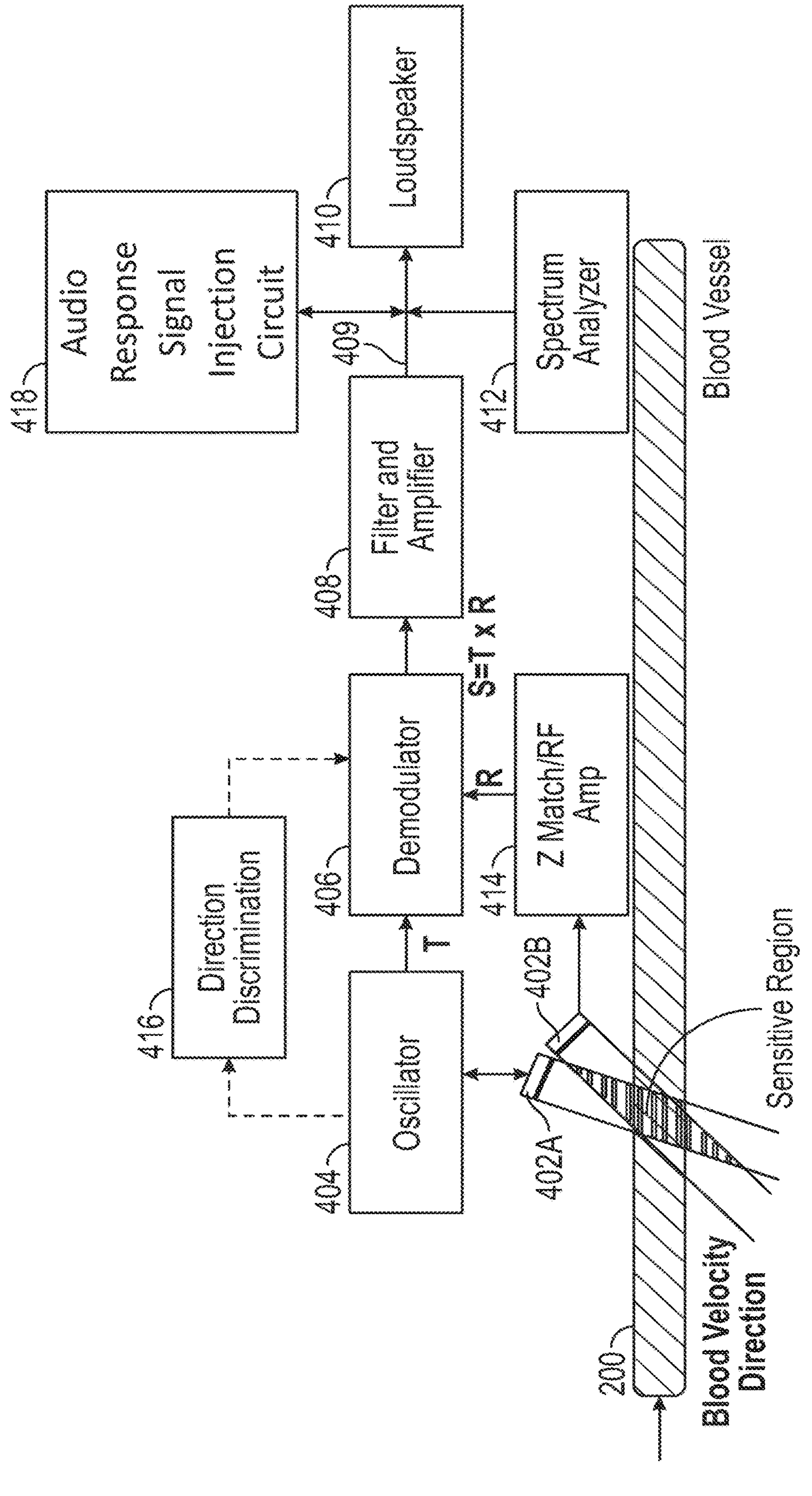
FIG. 4 is a schematic block diagram showing portions of the signal processing and other circuitry associated with the system-portions of which can be located at one of the wearable carriers, other portions of which can be located at the local or remote user interface.

FIG. 4 is a schematic block diagram showing portions of the signal processing and other circuitry associated with the system 100—portions of which can be located at one of the wearable carriers 102, other portions of which can be located at the local or remote user interface 104. Communications therebetween can be established and performed using the transceiver 310 at the carrier 102 and the transceiver 110 at the user interface 104. Although FIG. 4 shows two transducer elements, including a transmitting element 402A and a receiving element 402B, more than two transducer elements can be included, as explained herein.

At least one oscillator 404 can be included in the transducer interface circuitry 306 or elsewhere in the system 100. The oscillator 404 can provide an AC electrical drive signal to drive a piezoelectric transducer element 402A-B operating in transmit mode, such as with a frequency in the ultrasound frequency range that generates a resulting ultrasound signal for insonating a target region of interest. The oscillator 404 can optionally be tunable, such as to select an appropriate drive signal frequency for a particular one of the piezoelectric transducer elements 402A-B. A demodulator 406 can be used to receive from the target region a detected ultrasound signal received at one of the piezoelectric transducer elements 402A-B, such as in response to insonation by another one of the piezoelectric transducer elements 401A-B. The demodulator 406 can demodulate the received electrical signal representative of the ultrasound response to insonation of the target region, and can demodulate its carrier frequency to a lower base frequency that is in the audio range. A filter and amplifier 408 can include inputs that can be electrically connected to corresponding outputs of the demodulator 406 to receive the resulting demodulated signal from the demodulator 406. The filter and amplifier 408 can perform further signal processing, such as highpass, lowpass, or bandpass filtering, slew rate filtering (e.g., to pass large slew rate signals and attenuate small slew rate signals such as typical of noise), and signal amplification (or attenuation) of the demodulated audio signal. This can help improve a dynamic range of the system 100, which, in turn, can help allow the healthcare provider user to listen to very small and very large audio signals, such as via a loudspeaker 410. The loudspeaker 410 can include inputs that can be electrically connected to corresponding outputs of the filter and amplifier 408. The loudspeaker 410 can play a resulting human audible sound signal that can be detected by the healthcare provider to discern the characteristic sounds of arterial blood flow generated using the Doppler flow meter. As discussed further in more detail herein, an audio response enhancement signal injection circuit can be included, for example, in the filter and amplifier 408, to boost the human audible sound signal above the noise floor to help enhance human perceptibility of the audible sound signal being played by the loudspeaker 410, such as by employing Stochastic Resonance (SR).

A spectrum analyzer 412 can be included, such as in the user interface 104. The spectrum analyzer 412 can be used to analyze frequency content of the audio signal that is output by the filter and amplifier 408 to the loudspeaker 410. The spectral content information from the audio signal can include information that can be analyzed spectrally to determine information about blood flow that can be diagnostically useful to the healthcare provider. Such raw or signal-processed spectral information, or an indication generated based therefrom, can be displayed to the healthcare provider on the display 106 of the user interface 104.

An impedance-matched RF amplifier 414 can be included in the system 100. For example, the RF amplifier 414 can be located at the wearable carrier 102. Inputs of the RF amplifier 414 can be electrically connected to outputs of one or more of the transducer elements 402, such as the receiving transducer element 402B in FIG. 4. The receiving ultrasound transducer element 402B can be configured to operate in a receive mode. In the receive mode, the receiving ultrasound transducer element 402B can receive an ultrasound response signal in response to insonation of a target area by another ultrasound transducer element, such as the transmitting transducer element 402A in FIG. 4. The RF amplifier 414 can include impedance-matching circuitry. The impedance matching circuitry can detect a transducer-skin interface impedance associated with one or multiple ones of the transducer elements 402. In response to the detected transducer-skin interface impedance, the impedance matching circuitry can match one or more filtering or amplifying parameters of the RF amplifier 414. For example, a center frequency of filtering circuitry of the RF amplifier 414 can be tuned in response to a measurement of the detected transducer-skin interface impedance. This can help increase a signal-to-noise ratio of the system 100.

Direction discrimination circuitry 416 can also optionally be included in the system 100. The direction discrimination circuitry 416 can be employed to help determine a direction of blood flow in a target blood vessel of interest-such as to help distinguish between an artery and a vein, for example. The piezoelectric transducer elements 402 can be configured to distinguish between blood flow toward the Doppler transducer element 402 and blood flow away from the Doppler transducer element 402. For PAD diagnosis, for which arterial blood pressure and flow are of interest, it is desirable to measure arterial flow as opposed to venous flow. If a handheld "pencil-style" Doppler transducer is oriented by the healthcare provider user to be roughly parallel to the longitudinal axis of the blood vessel 200, then the resulting audio signal obtained from arterial blood flow can be directed to a different audio channel than the resulting audio signal obtained from venous blood flow. However, it can be difficult using a handheld Doppler probe to identify the orientation of the blood vessel. While it is true that limb arteries may often run somewhat parallel to the limb itself, this is not always the case. Thus, it is difficult to discriminate between arterial flow and venous flow solely based upon directional information associated with the blood vessel being analyzed.

The direction discrimination circuitry 416 can be employed to help identify the direction of the blood vessel with respect to the limb. The direction discrimination circuitry 416 can be programmed to select between different permutations or combinations of individual ones the transducer elements 402 within an arrangement of more than two or even many such transducer elements 402. This can include performing a search for a combination of piezoelectric ultrasound transducer elements 402 that yields the highest Doppler shift frequency among the various combinations of transducer elements 402. A particular combination of piezoelectric ultrasound transducer elements 402 that yields the highest Doppler shift frequency can be used to define the directional geometry of the blood vessel path as being associated with that particular combination.

Doppler tomography can therefore be performed by the system, such as can employ the direction discrimination circuitry 416. By trying various combinations of the piezoelectric ultrasound transducer elements 402, the system 100 can be used to locate the actual arterial blood vessel in the limb. An indication of the located arterial blood vessel can be displayed to the healthcare provider user. For example, an LED-type display on the carrier 102 can be lighted in a manner to help indicate the blood vessel location, orientation, or both. Additionally or alternatively, this information can be displayed on the display 106 of the user interface device 104, and can be overlaid or otherwise combined with other useful diagnostic information, such as an image or a representation of the patient's limb. Thus, the direction discrimination circuitry 416 can be used to help identify an artery, to help identify a vein, or to help distinguish between an artery and a vein. This is useful for PAD diagnosis so that arterial flow is properly being considered and venous flow is properly being disregarded. This can also be useful for a purpose other than for PAD diagnosis. For example, a similar technique can be used to distinguish between arterial flow and venous flow of a blood vessel to help identify or locate a vein on a limb (as opposed to an artery) such as for inserting a needle or intravenous catheter into a vein and to avoid doing so into an artery, for example.

An audio response enhancement signal injection circuit 418 can be included in the system 100, such as at the user interface device 104. The audio response enhancement signal injection circuit 418 can be configured to generate and vary at least one of an amplitude or bandwidth of an audio response enhancement signal that can be summed onto or otherwise injected onto a signal pathway, such as at node or bus 409, being provided to the inputs of the loudspeaker 410, such as using one or more aspects of the adaptive or other stochastic resonance (SR) techniques described herein. The variable audio response enhancement signal from the audio response enhancement signal injection circuit 418 can be summed, superpositioned, or otherwise combined with the audio response signal from the filter and amplifier 408, such as at node or bus 409, to make it easier for the healthcare provider user to register or discern the audio response signal at the node or bus 409 from the filter and amplifier 408 when played over the loudspeaker 410. This can help a healthcare provider user listen to the audio frequency Doppler flow signal for the pulsatile arterial blood flow sound characteristics, which can be very weak in clinical practice, particularly in a patient with PAD or another physiological condition that tends to impede blood flow.

For example, the audio response enhancement signal delivered by the audio response signal injection circuit 418 at the node or bus 409 can include at least one of a carrier signal, a noise signal, or atone signal to help enhance the audio response signal from the filter and amplifier 408 for audio playback to a user of the system, such as via the loudspeaker 410. As explained herein, such audio response signal injection can help the healthcare provider user listen for and hear the characteristic sounds of arterial blood flow, which might otherwise be too weak such that it may otherwise be difficult or impossible to hear when the audio signal of interest is at a level that is at or below a noise floor of other noise in the system 100 or its environment.

For example, the audio response signal from the audio response signal injection circuit 418 can be enhanced by an injected noise or other enhancement signal. This can be referred to herein as stochastic resonance. While stochastic resonance can be applied in an imaging context, here it can be uniquely employed in a non-imaging context to enhance an audio signal carrying Doppler-shifted audio information indicative or characteristic of pulsatile arterial blood flow. Stochastic resonance allows enhancement of a sub-detection-threshold signal that can include Doppler-shifted audio information indicative or characteristic of pulsatile arterial blood flow. Such enhancement can include using the audio response signal injection circuit 418 for adding a stochastic resonance or other audio response enhancement signal at the node or bus 409. Such an audio response enhancement signal being added at the node or bus 409 can include adding noise of sufficient amplitude to the audio response signal that is otherwise obtained and signal-processed from the ultrasound transducer elements 402 and presented by the filter and amplifier 408 at the node or bus 409 to the loudspeaker 410. Such enhancement can thereby result in anon-zero Doppler-SR enhanced sensor output signal being played over the loudspeaker 410 that can be audibly discernable of pulsatile arterial blood flow to the healthcare provider or other user or algorithm using the Doppler-SR sensor to evaluate blood flow in a target vessel 200. Further, if the input Doppler-SR enhanced sensor audio response signal amplitude from the filter and amplifier 408 at the node or bus 409 changes overtime, then the optimal noise level of the audio response enhancement signal, provided by the audio response signal injection circuit 418 for enhancing the audio response signal being provided by the filter and amplifier 408 can be estimated and can be established or adjusted or its application time-window can be gated by the audio response signal injection circuit 418. Such adjustment can be performed in an open-loop manner, such as for calibration. Additionally or alternatively, such adjustment can be performed adaptively such as in a closed-loop feedback manner, such as on an ongoing or recurrent basis. In either an open-loop or closed-loop configuration, adjustment of the audio response enhancement signal can be performed in a manner that can be based upon a resonance curve, such as shown in FIG. 5.

Figure 5:
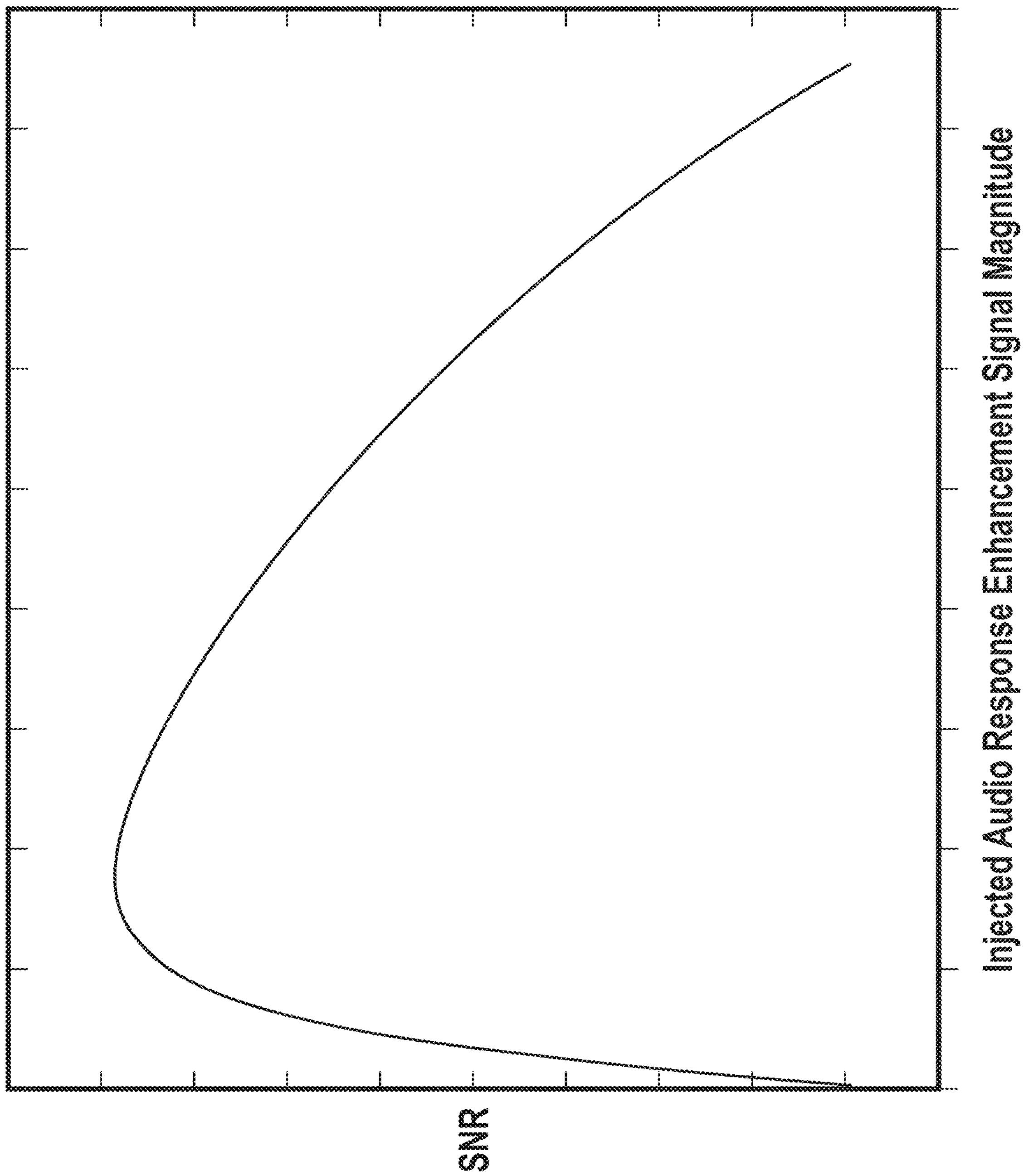
FIG. 5 shows a computer-simulated graph having a vertical axis representing Signal-To-Noise-Ratio (SNR) against a horizontal axis representing injected white noise amplitude.

FIG. 5 shows a computer-simulated graph having a vertical axis representing Signal-To-Noise-Ratio (SNR) against a horizontal axis representing injected enhancement signal amplitude, which in the example of FIG. 5 includes white noise amplitude. As shown in FIG. 5, as injected white noise amplitude is increased from zero, the SNR improves and peaks at some maximum, such as at least about 1.0, then the SNR begins to decline as the injected white noise amplitude is further increased. Operating the system 100 at or near peak SNR may be desirable, such as can include adapting the injected stochastic resonance or other enhancement signal being adjusted by the audio response signal injection circuit 418. The resonance curve shown in FIG. 5 can be stored in a lookup table, or as a representative fitted equation, in memory circuitry associated with the audio response signal injection circuit 418. As shown in FIG. 5, the present techniques of augmenting the Doppler-shifted baseband audio response signal with a superimposed noise signal can help a healthcare provider user (or proxy algorithm) to discern the characteristic sounds of pulsatile arterial blood flow even when the SNR is approaching 1.0.

For example, a variable bandwidth noise signal (e.g., including at least one of white, brown, or pink noise) can be added by the audio response signal injection circuit 418 as an audio response enhancement signal to the Doppler-shifted baseband audio response signal that is obtained from the filter and amplifier 408 at the node or bus 409 in response to insonation of a target region of interest. Because the Doppler baseband audio response signal is always within the frequency range of human hearing, a "white noise" audio response enhancement signal is likely to contain some overlapping frequencies. Thus, enhancing the Doppler baseband audio response signal from the filter and amplifier 408 by adding in a white noise signal as the audio response enhancement signal from the audio response signal injection circuit 418 for combined playback by the loudspeaker 410 can help render the Doppler baseband audio response signal from the filter and amplifier 408 perceivable to a healthcare provider operator or to another user or to an algorithm-enabled device.

Once a perceivable Doppler baseband audio response signal is attained, or using an alternative auxiliary cardiac cycle signal as explained herein, one or more other characteristics of the Doppler-SR system may be employed, such as to help increase the signal amplitude or the SNR of the enhanced Doppler baseband audio response signal. Additionally or alternatively, once a human-perceivable or device-perceivable Doppler baseband audio signal is obtained, or using auxiliary cardiac cycle information, the audio response signal injection circuit 418 can be employed to establish or adjust one or more characteristics of the audio response enhancement signal, if desired. For example, upon detecting a perceivable Doppler-shifted baseband audio signal (enhanced by the audio response enhancement signal) indicative of pulsatile arterial blood flow being played by the loudspeaker 410, the audio response signal injection circuit can adaptively switch from broadband white noise injection via the audio response enhancement signal to a narrower band noise injection, such as can be band-limited to a measured audio frequency range of the Doppler baseband audio response signal. The spectrum analyzer 412 can be used to measure the audio frequency range of the Doppler baseband audio response signal. This band-limiting of the injected enhancement signal can help increase the signal-to-noise ratio of the Doppler baseband audio response signal of interest while helping preserve its perceptibility by continuing to inject the audio response enhancement signal, if helpful.

Figure 6A:
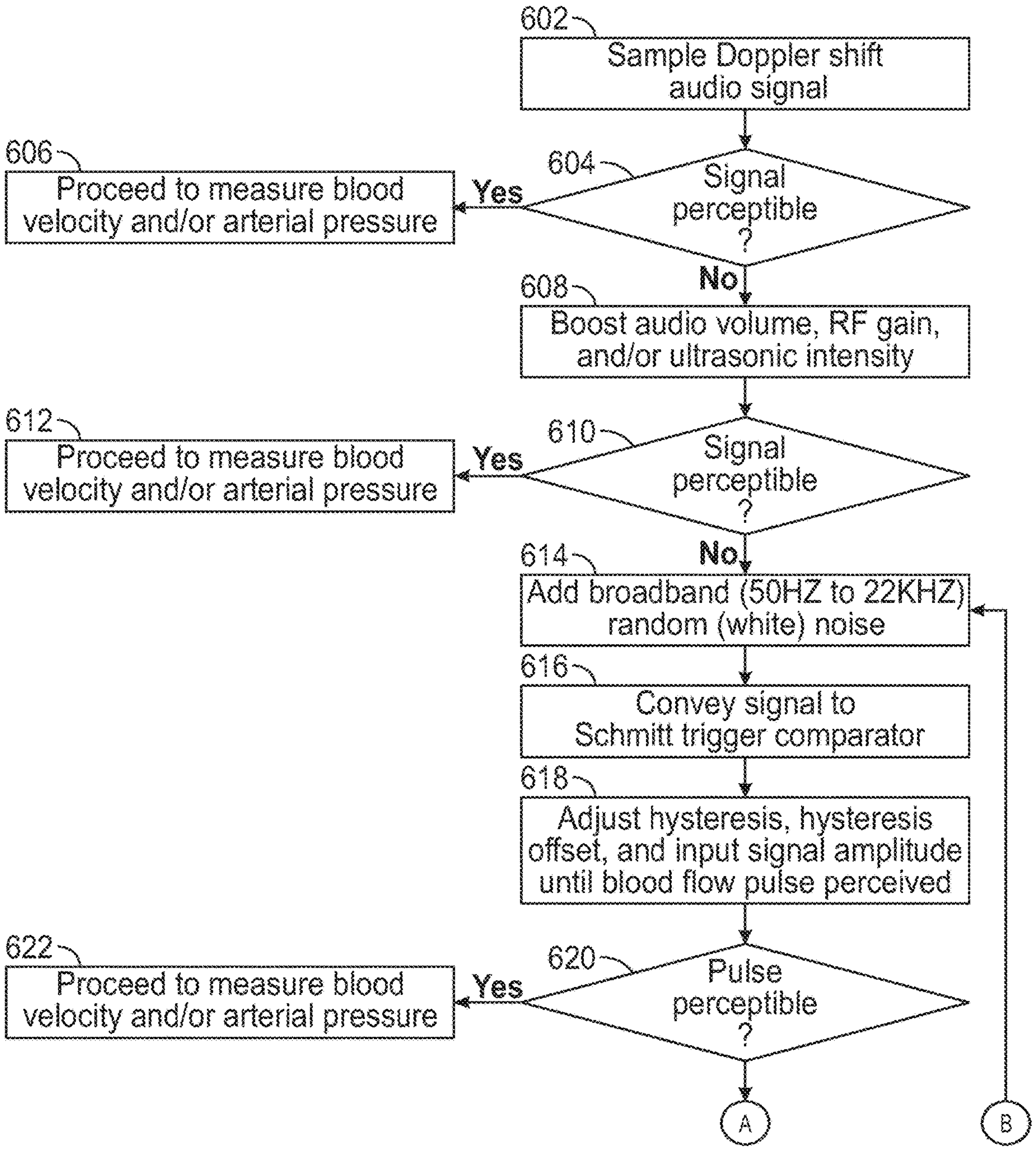
FIGS. 6A-6B shows a flow chart of an example of operating the audio response signal injection circuit 418, such as for SR-assisted discernment of the Doppler baseband audio response signal, which can include using one or more control signals provided by the controller circuitry, the processor, or both.
Figure 6B:
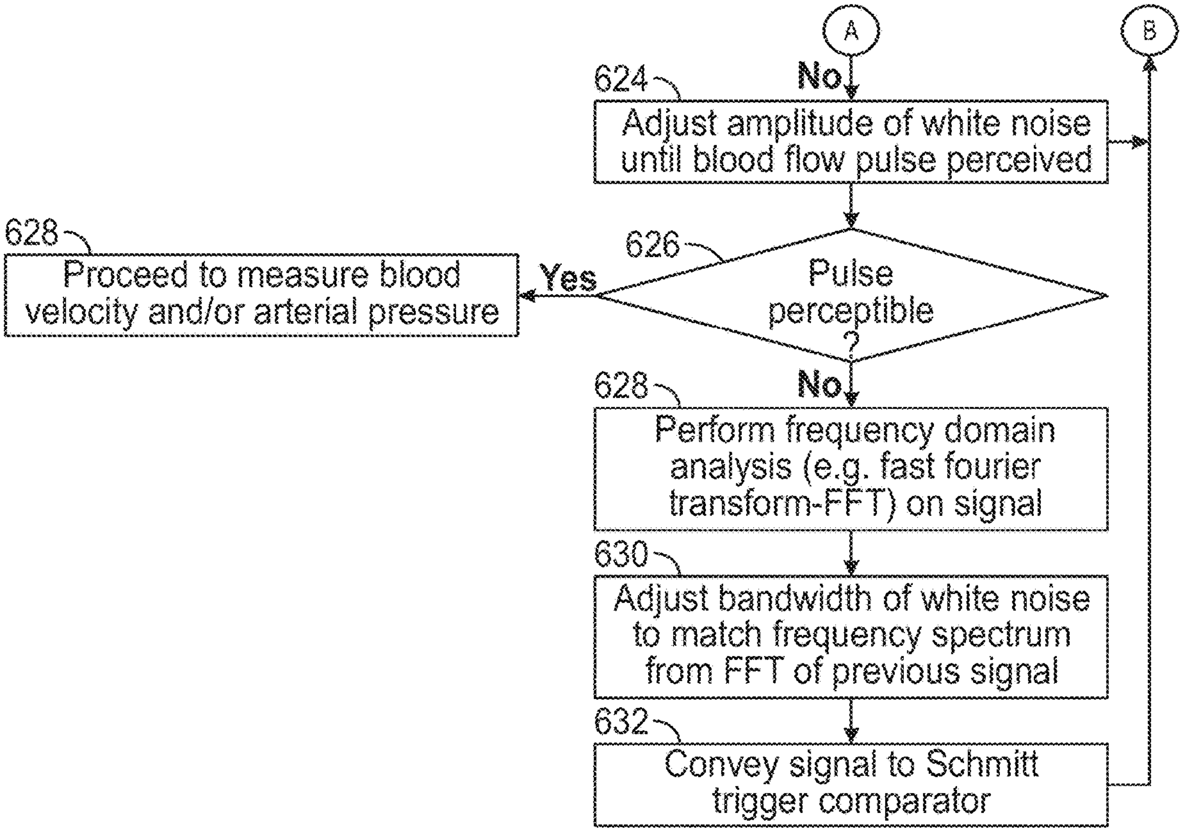

FIGS. 6A-6B show a flow chart of an example of portions of methods for operating the audio response signal injection circuit 418, such as for SR-assisted discernment of the pulsatile arterial blood flow information in the Doppler-shifted baseband audio response signal, which can include using one or more control signals provided by the controller circuitry 308, the processor 112, or both.

At 602, the Doppler-shifted audio signal output by the filter and amplifier 408 at the node or bus 409 can be acquired or sampled, in the analog or digital domain. The acquired or sampled signal can be signal-processed and provided to the loudspeaker 410, such as for playback to a healthcare provider user to discern the characteristic sounds of pulsatile arterial blood flow, or for further signal processing, such as which can serve as a proxy for the healthcare provider user to discern the characteristic sounds of pulsatile arterial blood flow.

At 604, it can be determined whether the Doppler shifted audio signal output by the filter and amplifier 408 at the node or bus 409 includes characteristic sounds of pulsatile arterial blood flow that are perceptible, such as to the healthcare provider user listening via the loudspeaker 410 or to a signal-processing algorithm serving in a similar role to the healthcare provider in listening for the distinct Doppler blood flow sounds. For example, the healthcare provider user can provide user-input, such as via the user interface 104, when the Doppler shifted audio signal output heard over the loudspeaker 410 has become perceptible. Such information can be used for diagnostic purposes for a particular patient, or as part of ground truth training data for training a machine learning model, such as explained herein. Alternatively or additionally, a signal-processing algorithm can use a trained learning model to detect perceptibility of the characteristic of pulsatile arterial Doppler blood flow sounds, such as described herein.

At 604, if the Doppler shifted audio signal output provided by the filter and amplifier 408 at the node or bus 409 includes characteristic pulsatile arterial blood flow sounds that are perceptible, then, at 606, the system 100 can proceed to measure blood velocity, arterial blood pressure, or both. Such measurements can be performed using Doppler flow measurements from the arrangement of piezoelectric transducers 402. Otherwise, if at 604 the characteristic sounds of the Doppler shifted audio signal output provided by the filter and amplifier 408 at the node or bus 409 are not perceptible, then, at 608, one or more system parameters can be adaptively adjusted, such as can be controlled by one or both of the controller 308 or the processor 112.

At 608, adjusting one or more system parameters can include boosting the audio signal level. This can include adjusting an amplifier gain of the filter and amplifier 408. Additionally or alternatively, it can include adjusting an ultrasound transmit energy intensity, such as by increasing an amplitude of a driver signal being provided to one or more of the ultrasound transducer elements 402 being used for insonating the target regions. Additionally or alternatively, it can further include adjusting an ultrasound receive energy intensity, such as by increasing a gain of the RF amplifier 414. Additionally or alternatively, it can further include using a tunable bandpass or other filter circuit for attenuating transmit or response signal frequencies away from the insonification frequency.

At 610, after adjusting a system parameter at 608, another check can be performed to determine whether the Doppler shifted audio signal output provided by the filter and amplifier 408 at the node or bus 409 includes characteristic pulsatile arterial blood flow sounds that are perceptible, such as in a similar manner to that described herein with respect to 604. If so, then at 612, the system 100 can proceed to measure blood velocity, arterial blood pressure, or both, such as in a similar manner to that described herein with respect to 606. Otherwise, stochastic resonance type signal enhancement can be performed, such as can include adding noise at 614.

At 614, the audio response signal injection circuit 418 can be used to enhance the Doppler shifted audio signal provided by the filter and amplifier 408 at the node or bus 409. This can include injecting broadband (e.g., 50 Hz to 22 kHz, inclusive) random white noise that can be summed with or superpositioned upon the Doppler shifted audio signal output by the filter and amplifier 408 at the node or bus 409. As explained herein, summing or superpositioning such white noise can actually help bring the Doppler shifted audio signal provided by the filter and amplifier 408 at the node or bus 409 into a range of perceptibility for a human healthcare provider user or for a signal processing algorithm proxy for such a user.

At 616, after injecting the noise at 614, such as using the audio response signal injection circuit 418, the resulting summed or superpositioned signal at the node or bus 409 can be conveyed to the loudspeaker 410 and to a threshold or other detection circuit, such as a Schmitt trigger buffer or other comparator circuit that can be included in the signal-processing circuitry of the audio response signal injection circuit 418. The Schmitt trigger buffer or other comparator can include a comparison detection threshold, such as which can include offset, hysteresis, or both. Including hysteresis can help inhibit or prevent unwanted comparator switching, such as due to noise that is either injected to enhance perceptibility or that is otherwise present.

At 618, one or more of the hysteresis, offset, the audio response signal amplitude provided by the filter and amplifier 408, or the injected noise signal amplitude or bandwidth can adaptively be adjusted, such as until the characteristic Doppler flow pulsatile signal is perceived at 620.

At 620, the comparison detection threshold of the Schmitt trigger buffer or other comparator in the signal-processing circuitry of the audio response signal injection circuit 418 can be used to determine whether sounds characteristic of arterial pulsatile blood flow are perceptible in the enhanced signal at the node or bus 409, which includes the injected noise summed or superpositioned onto the audio response signal provided by the filter and amplifier circuit 408. If so, then at 622, the system 100 can proceed to measure blood velocity, arterial blood pressure, or both, such as in a similar manner to that described herein with respect to 606. Otherwise, amplitude of the injected noise signal can be adjusted at 624, and process flow can return to 614.

At 626, after adapting or adjusting the amplitude of the noise signal at 624, the comparison detection threshold of the Schmitt trigger buffer or other comparator in the signal-processing circuitry of the audio response signal injection circuit 418 can be used to determine whether sounds characteristic of arterial pulsatile blood flow are perceptible in the enhanced signal at the node or bus 409. If so, then at 628, the system 100 can proceed to measure blood velocity, arterial blood pressure, or both, such as in a similar manner to that described herein with respect to 606. Otherwise, further signal processing and adaptation or adjustment can be performed at 630.

At 630, the spectrum analyzer 412 can be used to perform frequency domain analysis on the raw Doppler-shifted audio response signal or on the noise-enhanced signal provided by the filter and amplifier 408 at the node or bus 409. This can include transforming the time-domain signal of interest into the frequency domain, such as by performing a Fast Fourier Transform (FFT). For example, by performing a FFT on the raw Doppler-shifted audio response signal provided by the filter and amplifier 408, a frequency spectrum and spectral bandwidth of this signal can be determined. A bandwidth of the noise being injected by the audio response signal injection circuit 418 can then be adapted or adjusted at 630, such as to match the spectral bandwidth of the raw Doppler-shifted audio response signal provided by the filter and amplifier 408. By doing such adaptation or adjustment of the injected stochastic resonance or other enhancement signal, the injected noise of the enhancement signal will only include frequencies that are within the spectral bandwidth of the raw Doppler-shifted audio response signal provided by the filter and amplifier 408, which can help improve pulsatile blood flow perceptibility and SNR. Then, at 632, the bandwidth-adjusted noise-enhanced signal at node 409 can be conveyed to the Schmitt trigger buffer or other comparator, such as described herein with respect to 616, and process flow can return to 624.

Although FIGS. 6A-6B describes techniques of measuring one or more blood flow parameters, such as blood velocity, arterial pressure, or the like, including how to adapt or adjust the injected stochastic resonance or other enhancement signal or various operational parameters in order to obtain such measurements at one or more of 612, 622, 628, such static or adaptive continuous wave Doppler measurements can be included in recurrent or ongoing polling of one or more pairs of transducers 402. This polling can include recurrently repeating such measurements at one or more of 612, 622, 628. Including such ongoing polling can sometimes be desirable, for example, to help ensure that the continuous wave Doppler blood flow signal is maintained over the course of such polling, for example, even if there is some physical movement of the patient being monitored during a diagnostic or therapeutic medical procedure.

Figure 6C:
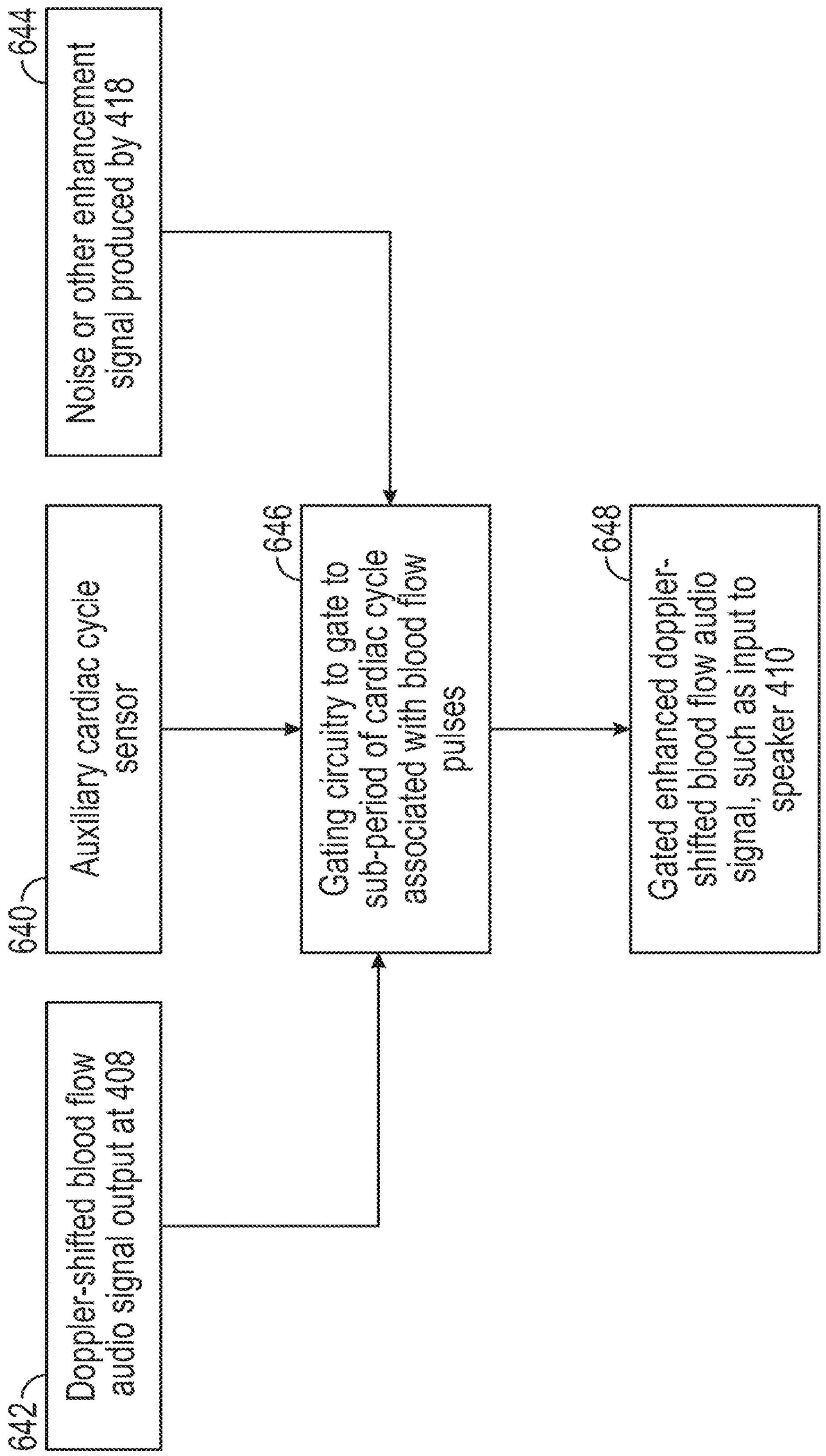
FIG. 6C is a block diagram that shows an example of portions of an additional or alternative technique of adaptively applying stochastic resonance noise-enhancement or other enhancement signal being injected, such as which can include gating the injected enhancement signal to synchronize applying the noise or other enhancement signal during a subperiod of the time period of the subject's cardiac cycle.

FIG. 6C is a block diagram that shows an example of portions of an additional or alternative technique of adaptively applying stochastic resonance noise-enhancement or other enhancement signal being injected at node 409. FIG. 6C illustrates a technique that can include adjusting a duty cycle of the injected enhancement signal, such as can include gating a timing of the injected enhancement signal such as to synchronize applying the noise or other enhancement signal during a subperiod of the time period of the subject's cardiac cycle that is limited to the time subperiod associated with the arterial pulses, and to avoid applying the noise during the remainder of the cardiac cycle.

An auxiliary cardiac cycle sensor 640 can optionally be included in the system 100, such as on the carrier 102 or located elsewhere, to sense the cardiac cycle of the subject without requiring determining the cardiac cycle of the subject from the Doppler-shifted blood flow audio signal itself-however, cardiac cycle information can alternatively be obtained from the Doppler-shifted blood flow audio signal itself, if desired. The auxiliary cardiac cycle sensor 640 can take various forms. For example, the auxiliary cardiac cycle sensor 640 can include a microphone and associated audio amplification circuitry to listen for audible indications of the pulsatile blood flow sub-period of the cardiac cycle. In other examples, the auxiliary cardiac cycle sensor 640 can include an electrocardiogram (ECG) signal sensor, an impedance sensor, a blood pressure cuff sensor, a photoplethysmographic (PPG) or other optical sensor.

Cardiac cycle information from the auxiliary cardiac cycle sensor 640, Doppler-shifted blood flow audio signal output at 408, and noise or another enhancement signal produced by the audio response signal injection circuit 418 can all be received at 646 by gating circuitry that can be included within or coupled to the audio response signal injection circuit 418. The gating circuitry can be used to gate application of the noise or other enhancement signal produced by the audio response signal injection circuit 418 in the time domain. The gating circuitry can use a time-domain threshold or level detection comparison or other determination of the sub-period associated with the arterial blood flow pulses to limit application of the noise or other enhancement signal to that sub-period, which can be a small fraction of the entire cardiac cycle. By adaptively limiting application of stochastic resonance noise or any other enhancement signal to the sub-period associated with the pulsatile blood flow to be perceived in the Doppler-shifted blood flow audio signal, the SNR can be improved relative to applying the stochastic resonance noise or any other enhancement signal over a larger duration or the full duration of the cardiac cycle.

Also, repeated, recurrent, or ongoing monitoring of the raw or enhanced Doppler shift audio response signal at 409 can be helpful to evaluate the effectiveness of an interventional therapy or other therapeutic treatment, such as by performing such measurements before and after such treatment, for comparison, or even performing measurements repeatedly during such treatment. For example, in the case of PAD, treatment can include surgery on one of the great blood vessels in the thigh or calf, such as a femoral artery or a popliteal artery. By placing the carrier 102 of the system 100 on the ankle or foot before surgery, a pre-operative baseline raw or enhanced Doppler shift audio response signal at 409 can be obtained from, for example, a first measurement of a posterior tibial artery. Then, all or part of the therapeutic procedure (e.g., atherectomy, stent, or the like) can be performed. After performing all or part of the therapeutic procedure, a repeated second blood flow measurement can be performed, e.g., using the same operational parameters that were used for making the pre-operative baseline first measurement. The repeated second blood flow measurement can be compared to the pre-operative baseline first blood flow measurement. Such a comparison can be used to assess, confirm, or document any improvement in blood flow resulting from the therapeutic procedure. For example, improved blood flow can be represented by an increase in Doppler-shifted signal amplitude, an increase in Doppler-shifted frequency, and a reduction in spectral broadening, such as described elsewhere herein.

Figure 6D:
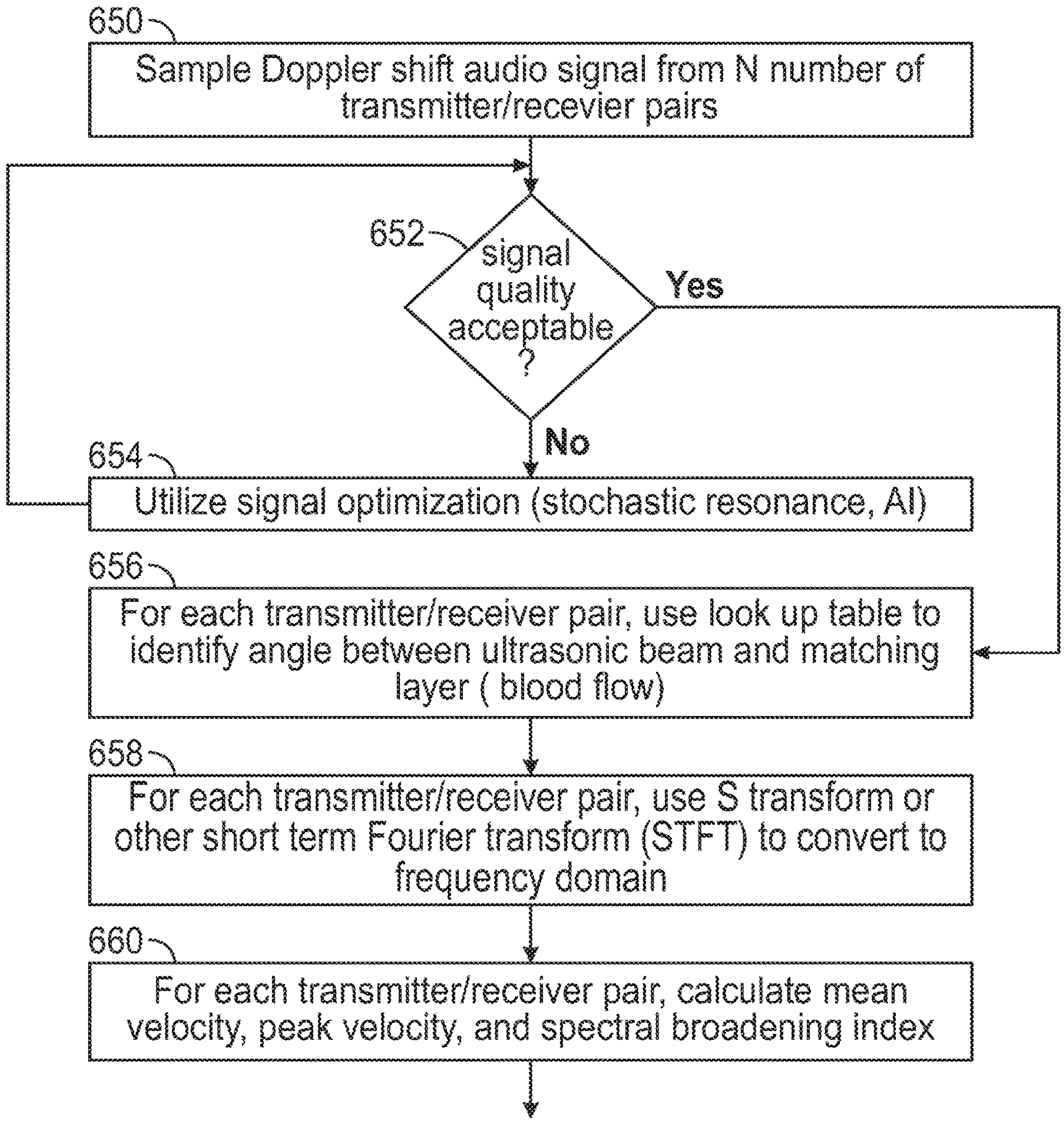
FIGS. 6D-6E are flow charts illustrating an example of portions of techniques for: (1) using various combinations of transducers and optimization (FIG. 6D) such as to help determine one or more Figures of Merit (FOMs) from raw or enhanced Doppler-shifted audio response signal information; and (2) evaluating efficacy of a therapeutic medical procedure (FIG. 6E).
Figure 6E:
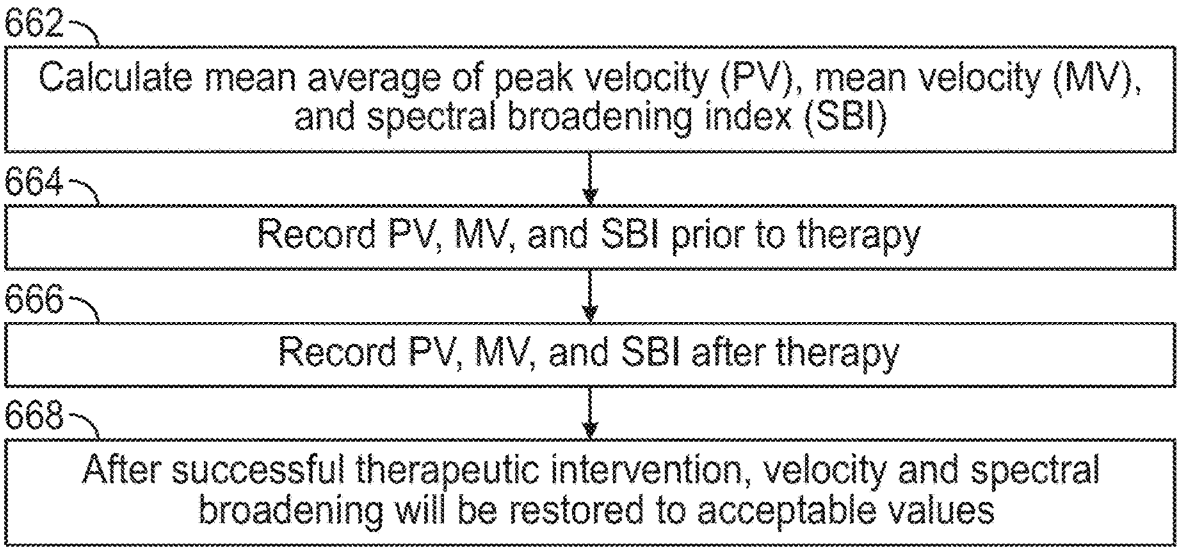

FIGS. 6D-6E are flow charts illustrating an example of portions of techniques for: (1) using various combinations of transducers and optimization (FIG. 6D) such as to help determine one or more Figures of Merit (FOMs) from raw or enhanced Doppler-shifted audio response signal information; and (2) evaluating efficacy of a therapeutic medical procedure (FIG. 6E).

In FIG. 6D, at 650, a raw Doppler-shifted audio response signal can be acquired. This can include sampling the raw Doppler-shifted audio response signal provided by the amplifier 408 from a number "N" of pairs (or other combinations) of transmit and receive transducers 402.

At 652, it can be determined whether the signal quality of the raw Doppler-shifted audio response signal provided by the amplifier 408 is acceptable for one or more of the N pairs of transducers 402. This can involve determining whether or to what degree pulsatile sounds characteristic of arterial blood flow are present. Additionally or alternatively, it can involve evaluating one or more time or frequency domain parameters of the signal, such as signal strength, Doppler frequency shift, a degree of spectral broadening, or the like. At 652, if the signal quality is deemed not acceptable, then process flow can proceed to 654. At 652, if the signal quality is deemed acceptable, then process flow can continue to 656.

At 654, signal optimization can be performed for one or more of the N pairs of transducers 402. This can involve using or adapting the stochastic resonance noise or other enhancement signal that can be injected by the audio response signal injection circuitry 418, such as described herein. This can additionally or alternatively involve using a trained machine learning model or other techniques such as described herein, such as for improving or optimizing one or more operating parameters of the system 100. After performing such signal optimization for one or more of the N pairs of transducers 402, process flow can return to 652.

At 656, for individual ones or each of transmitter and receiver pair of interest in the N pairs of transducers 402, a look-up table can be used to identify the angle between its corresponding ultrasonic beam and the plane of a matching layer or other interface with the patient's skin. Because the angles of individual transducers 402 may differ, but are fixed by the arrangement of the particular transducer carrier, the expected target region of interest associated with a particular pair of transducers 402 can be determined.

At 658, for individual ones or each of the transmitter and receiver pairs of interest in the N pairs of transducers 402, an "S" transform or other Short Term Fourier Transform (STFT) can be used to convert the time-domain signal into the frequency domain, such as using the spectrum analyzer 412.

At 660, for individual ones or each of the transmitter and receiver pairs of interest in the N pairs of transducers 402, one or more of a mean (or other central tendency) of blood flow velocity can be calculated, a peak blood flow velocity can be calculated, or a spectral broadening index (SBI) can be calculated. Process flow can then proceed to 662 in FIG. 6E.

In FIG. 6E, at 662, a mean or other central tendency of one or more of the values calculated at 660 for individual pairs can be determined across multiple ones or all of the pairs of interest in the N pairs of transducers 402.

At 664, baseline (pre-therapy) values of peak velocity, mean velocity, and spectral broadening index can be acquired, such as just before performing a medical therapy procedure.

At 666, post-therapy values of peak velocity, mean velocity, and spectral broadening index can be acquired, such as just after performing a medical therapy procedure.

At 668, the effect of the medical therapy procedure can be characterized, such as by comparing one or more or all of the post-operative values to the corresponding pre-operative baseline values. After a successful medical therapy procedure, the blood flow velocity and spectral broadening should demonstrate improvement or be restored to acceptable values.

FIGS. 7A, 7B, 7C, and 7D illustrate various views of an illustrative example of an arrangement of multiple ultrasound acoustic transducer elements 402 that can be included in the system 100, such as on the carrier 102.

Figure 7A:
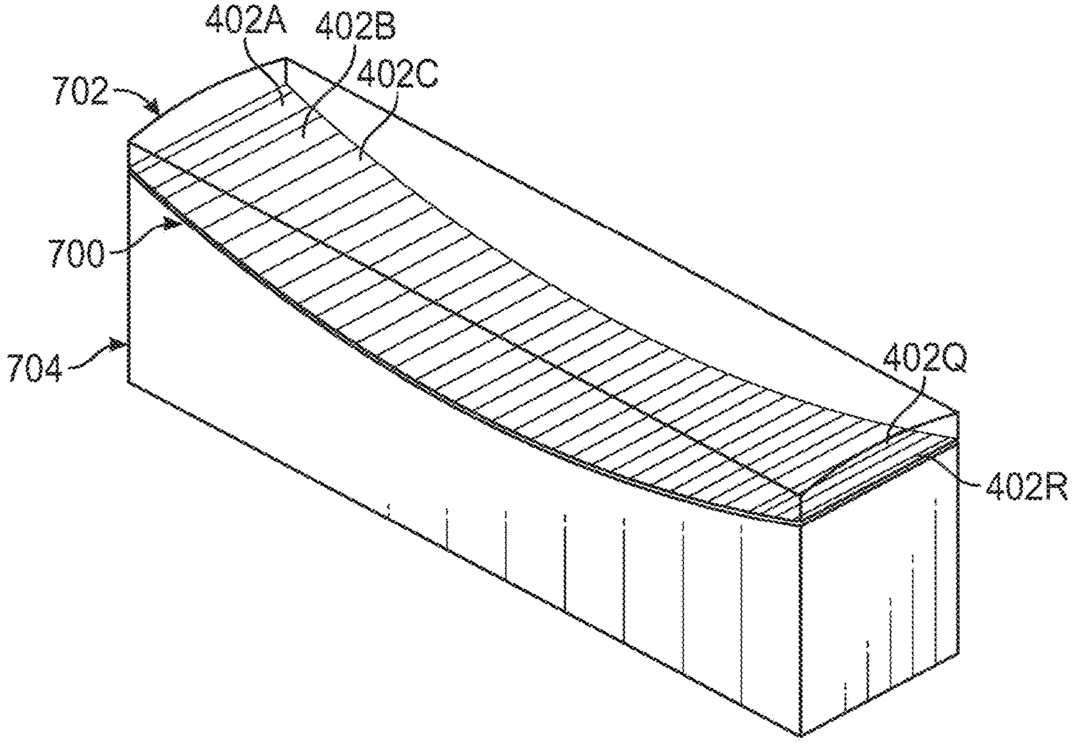
FIGS. 7A, 7B, 7C, and 7D illustrate various views of an illustrative example of an arrangement of multiple ultrasound acoustic transducer elements 402 that can be included in the system, such as on the carrier.

FIG. 7A shows a perspective view of an illustrative curved row phased array 700 of eighteen electronically-selectable piezoelectric acoustic transducer elements 402. In this example, the elongated transducer elements can be arranged side-by-side in a straight line with their widths separated by a spacing that can be defined therebetween. This straight line row of transducer elements 402 can be curved with respect to the faces of the various transducer elements 402, such as shown in FIGS. 7A and 7C. Such curvature can provide different locations, different angles, or both, with respect to a surface of the patient, from which insonation can be delivered or interrogation of a response signal can be achieved. Such ability to provide such variation can be helpful, such as to help establish an appropriate target zone from which blood vessel flow information can be obtained, or for avoiding a physiological structure, such as a wound or ulcer, in such insonation and interrogation. This curved row phased array 700 is a particular example of a one-dimensional (1D) array arrangement of the transducer elements 402. Other arrangements are also possible. In an example, the transducer elements 402 can be arranged in a two-dimensional (2D) array, such as can include an "n" by "m" 2D grid arrangement, in which "n" and "m" can each be an integer greater than 1. In an example, the transducer elements 402 can be arranged in a circular or in an annular configuration, which can additionally optionally include one or more transducers 402 located more centrally within the circular or annular arrangement. In an example, the transducers 402 that are circularly or annularly arranged can be located or positioned within a carrier such as to provide different angles between a face of such transducer elements 402 and a skin surface of the patient, while the transducers 402 that are located more centrally within such circular or annular arrangement of transducer elements 402 can be oriented with a face of such transducer elements more parallel to the skin surface of the patient. In this way, the corresponding acoustic field of individual ones of the circumferentially arranged transducer elements 402 can be configured with different angles so as to intersect with the interrogation response reception field of the more centrally-located transducer elements 402 at differently specifiable depths beneath a surface of the skin of the patient. Deeper focused transducer elements 402 can employ a lower ultrasound insonation frequency than more superficially focused transducer elements 402, such as to help account for the increased attenuation associated with structures that are located deeper below the skin surface.

The elongate piezoelectric crystal PZT transducer elements 402 can include or consist of an 1-3 composite material. This can help provide higher conversion gain and sensitivity, wider excitation frequency bandwidth, and easier or better acoustic matching between the ultrasonic transducer elements 402 and the patient. Such easier or better acoustic matching between the ultrasonic transducer element 402 and the patient, in turn, can help yield smaller boundary reflections and a higher amplitude Doppler-shift flow signal. Each transducer element 402 can be configured for use as an ultrasound acoustic transmitter or receiver. As explained herein, by software-assisted or automatically (e.g., algorithmically or using a trained learning model) or manually selecting a particular combination of transmitter and receiver, different depths into the tissue, different positions on the patient's surface anatomy, or both, can be targeted.

As shown in FIGS. 7A, 7B, 7C, and 7D, the transducer elements 402 can be covered by an acoustic lens 702 or other covering on a top side of the transducer elements 402. The lens 702 can provide a spacing between skin of the subject and at least one of the acoustic transmitter or the acoustic receiver that is equal to a positive integer multiple of ¼ of an acoustic wavelength of the insonification signal, at the insonification frequency, in the lens 702. The transducer elements 402 can be backed by a non-transmissive acoustically absorptive or acoustically reflective acoustic backing 704 on a bottom side of the transducer elements 402 (e.g., in a direction away from the subject or in a direction away from a shortest path between a particular transducer element and an interface with the subject) to which the transducer elements 402 can be affixed. The acoustic backing 704 can take different forms, such as an air backing or a mixture of tungsten and epoxy, as examples. The acoustic backing 704 can help provide mechanical support, such as for affixing the transducer elements 402 to a fixture. The acoustic backing 704 can include a non-air material that can be selected so as to help reduce or eliminate reflections of ultrasound from the boundary between the PZT crystal transducer elements 402 and any air that would otherwise be located with a boundary against the PZT crystal transducer elements 402 in the absence of the acoustic backing 704. In a pulsed Doppler system, the non-air acoustic backing 704 can be used to help provide a wide bandwidth to the PZT crystal transducer elements 402. While wide bandwidth is useful in a pulsed Doppler flow or imaging system, a wider bandwidth may be associated with reduced sensitivity. Thus, in a system in which a high sensitivity is desired, such as in a continuous wave (CW) Doppler system, for example, an air acoustic backing 704 region may be selected over a non-air acoustic backing 704. In an example of the present approach in which the air acoustic backing 704 is used, a sufficiently wide insonation bandwidth, such as between 70 Hertz and 25 kiloHertz can still be obtained, with a resulting response signal having a high enough SNR to obviate the need for bandpass filtering of the audio signal that is communicated via the audio speaker 108 for sound playback to a healthcare provider user listening for characteristic pulsatile arterial blood flow, or to a device or algorithm or both that can serve as proxy for such a user.

Figure 7B:
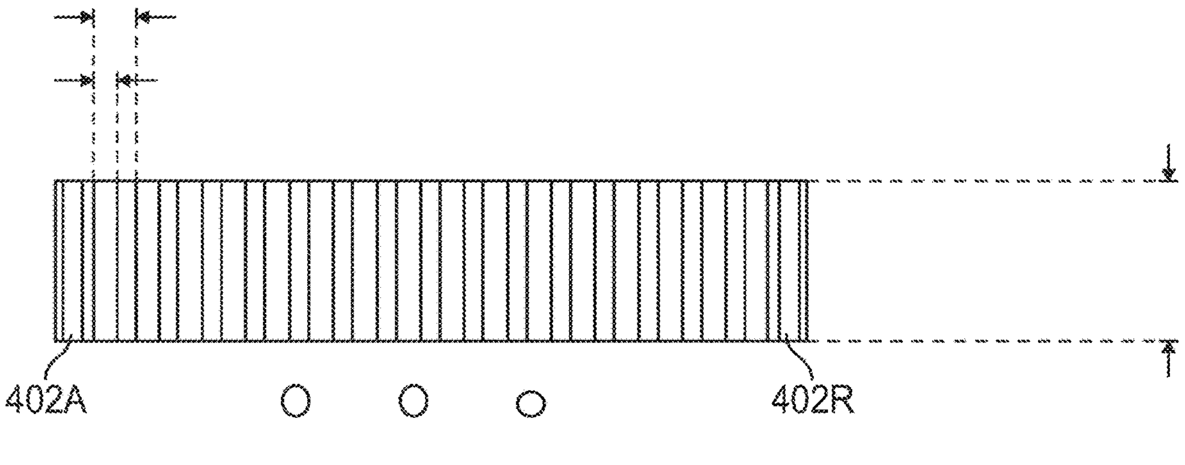
Figure 7C:
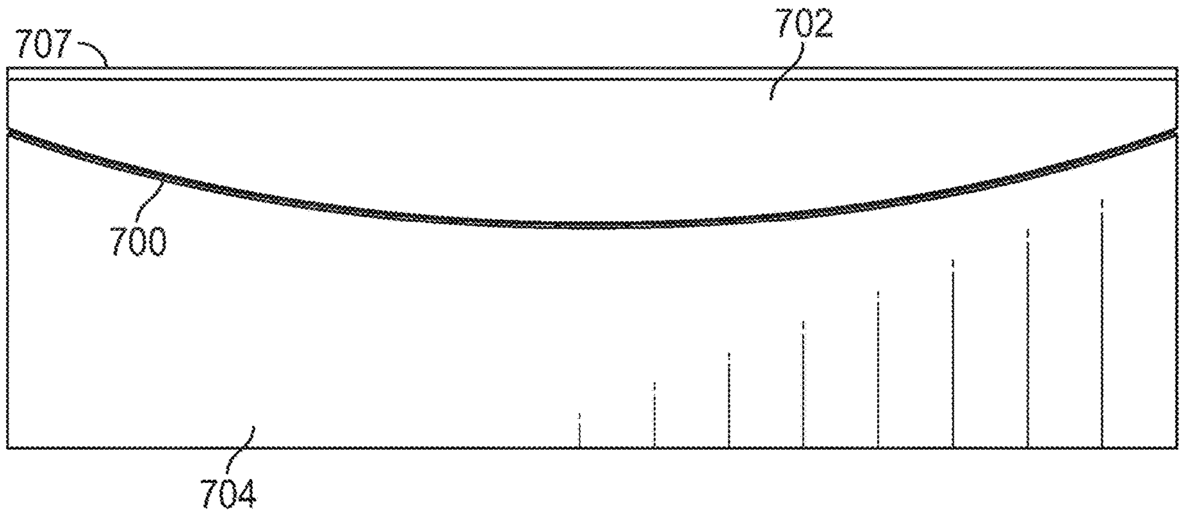

FIG. 7B shows atop view of the illustrative example of the phased array 700 of FIG. 7A, in which the piezoelectric transducer elements 402 are shown. In the example of FIG. 7B, each transducer element 402 can include an elongate 16 millimeter by 1 millimeter rectangular active transducer element 402. These transducer elements 402 can be arranged in a row, which can optionally be curved as shown in FIG. 7A. An illustrative example having 2 millimeter pitch spacing between longitudinal centerlines of respective adjacent transducer elements 402 is shown in FIG. 7B. The individual ones of the piezoelectric transducer elements 402 can be electronically selectable. For example, the various transducer elements 402 can be electronically selectable individually or in one or more groups, or in a phased array sequencing. The transducer elements 402 can be configured or re-configured, individually or in one or more of the same or different groups, such as to operate in a transmit mode to insonate a target region or to operate in a receive mode to receive response ultrasonic energy from the insonated target region. The curvature of the curved row of transducer elements 402 can be a concave circular or parabolic curvature or other similar arrangement. The curvature can help orient the focal points of the respective transducer elements 402 toward a commonly shared target point, a commonly shared target location, or a commonly shared target region. Alternatively or additionally, the curvature can help accommodate a physiological curved exterior placement location on the limb or other region of the patient undergoing analysis, if desired.

FIG. 7C shows a side view in which the radius of curvature of the phased array 700 of transducer elements 402 is shown as 50 millimeters. An ultrasound or other acoustic spacer or lens 702 can be affixed over the transducer elements 402. The lens 702 can help provide physical separation, a protective covering, or can help focus ultrasound energy being communicated to or from the target region by the various individual transducer elements 402 that are selectively being operated. A bottom surface of the lens 702, located against the transducer elements 402, can be curved, such as to accommodate the curvature of the phased array 700 of transducer elements 402. A top surface of the lens 702, located away from the transducer elements 402, can be flat, such as shown in FIG. 7C, or can be curved in a similar manner to the curvature of the phased array 700 of transducer elements 402, if desired, such as to accommodate a physiologically curved structure against which the lens 702 is to be placed. An acoustic matching layer 707 can optionally be provided on the top surface of the lens 702.

Figure 7D:
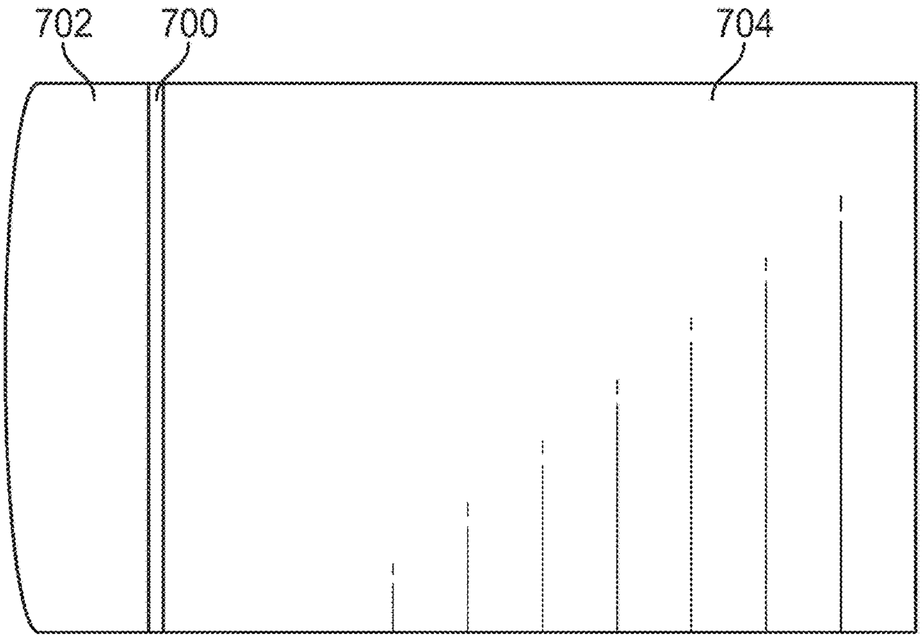

FIG. 7D shows another side view, orthogonal to the side view of FIG. 7C, showing the lens 702 and the backing 704. In the illustrative example of FIG. 7D, a height of the lens 702 extending beyond a tallest end or edge portion of the backing 704 is shown as 20 millimeters. As shown in FIG. 7D, the lens 702 may include lateral tapered edges. Additionally or alternatively, the lens 702 may include some lateral curvature, if desired.

Figure 8A:
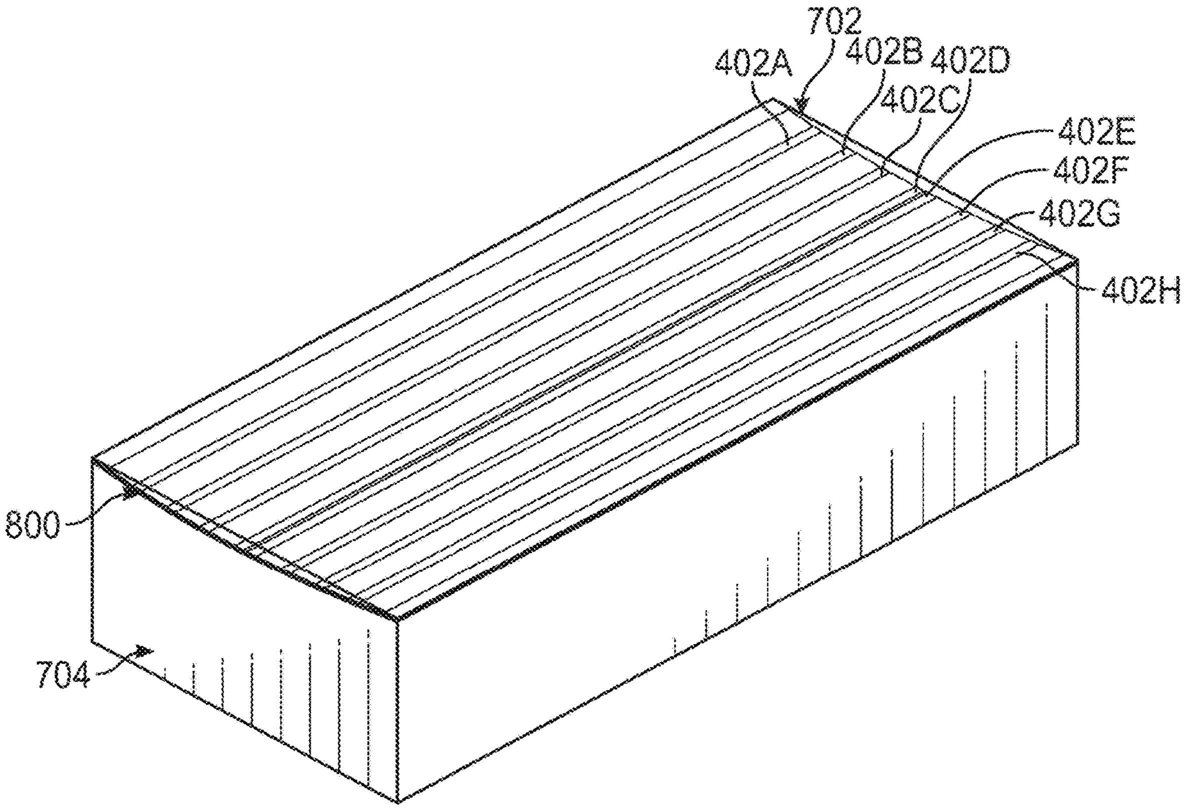
FIGS. 8A, 8B, and 8C illustrate various views of another arrangement of multiple transducer elements that can be included in the system, such as on the carrier.
Figure 8B:
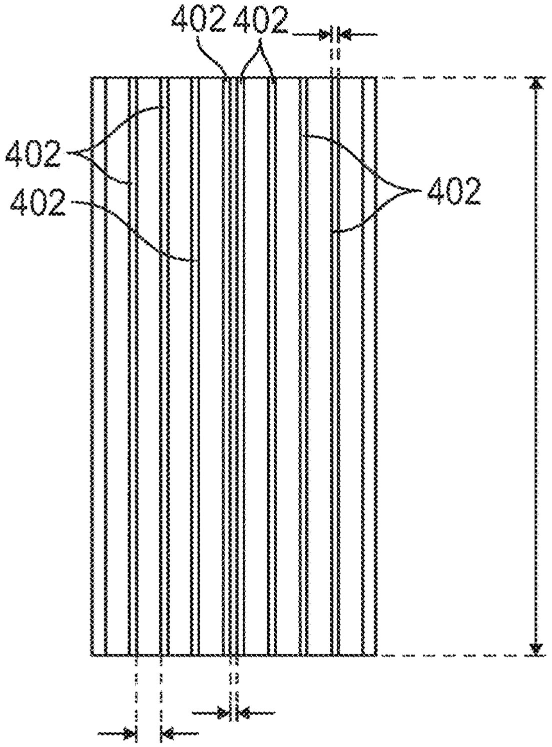
Figure 8C:
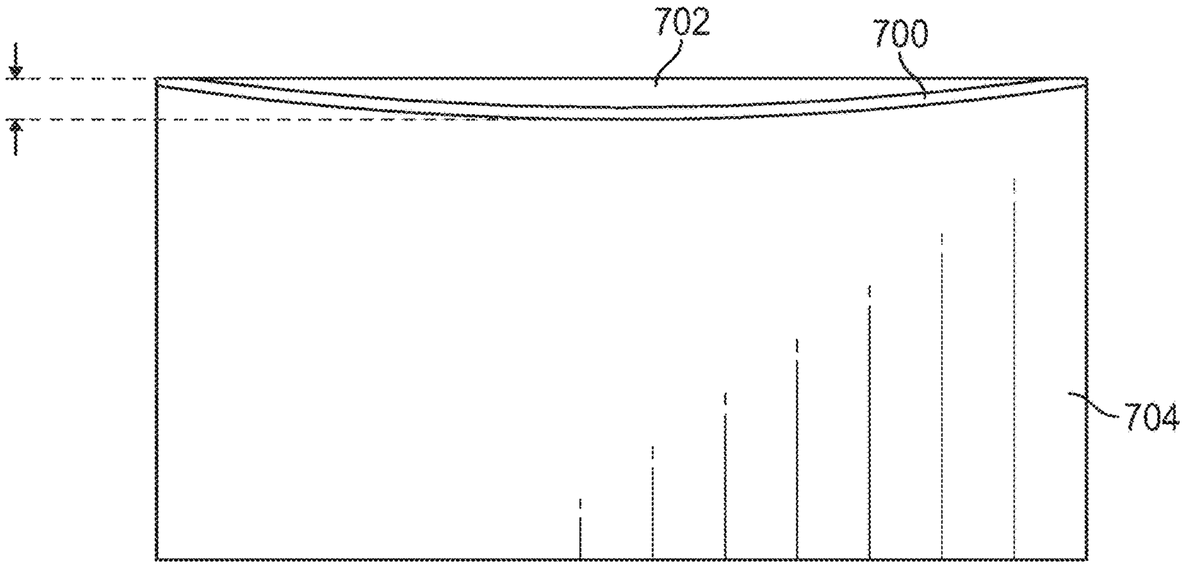

FIGS. 8A, 8B, and 8C illustrate various views of another arrangement of multiple transducer elements 402 that can be included in the system 100, such as on the carrier 102. FIG. 8A shows a perspective view of an illustrative curved row phased array 800 of eight electronically-selectable piezoelectric transducer elements 402. FIG. 8B shows a top view of the phased array 800 arrangement shown in FIG. 8A. FIG. 8C shows a side view of the phased array 800 arrangement shown in FIG. 8B. The phased array shown in FIGS. 8A, 8B, and 8C is similar to that shown in FIGS. 7A-7D, the description of which is not repeated here, for brevity. In FIGS. 8A-8C, the number of transducer elements is different from that shown in FIGS. 7A-7D. The sizes of the elongate transducer elements 402 in FIGS. 8A-8D are also different from those shown in FIGS. 7A-7D. As shown in FIGS. 8A-8D, the elongate transducer elements 402 can include a length of 40 millimeters and a width of 0.5 millimeters, with a spacing between the elongate transducer elements 402 being 1.5 millimeters, except between the center-most two transducer elements 402C and 402D, between which the spacing is 0.2 millimeters. A symmetric arrangement is shown with respect to a centerline that can extend between and parallel to the center-most two transducer elements 402C and 402D.

Figure 9A:
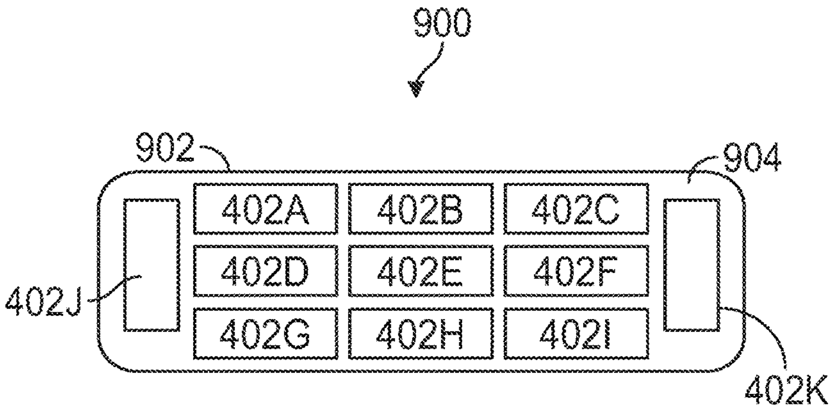
FIGS. 9A, 9B, and 9C illustrate another arrangement of elongate transducer elements that need not be arranged linearly in a row, such as shown and described with respect to FIGS. 7A-7D and FIGS. 8A-8D.
Figure 9B:
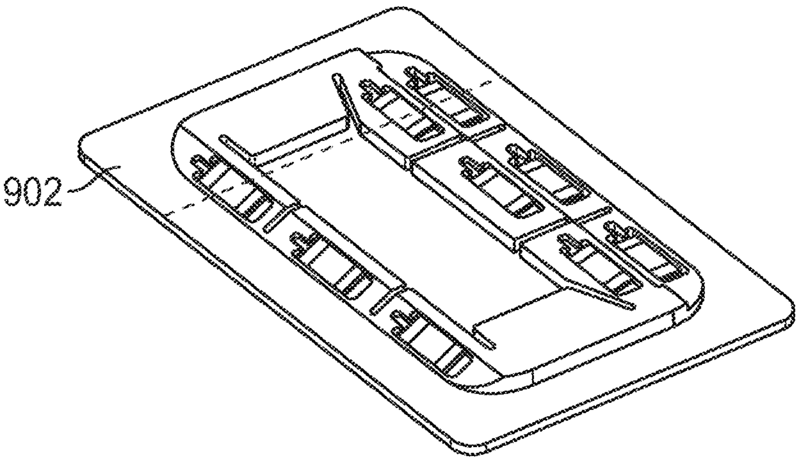
Figure 9C:
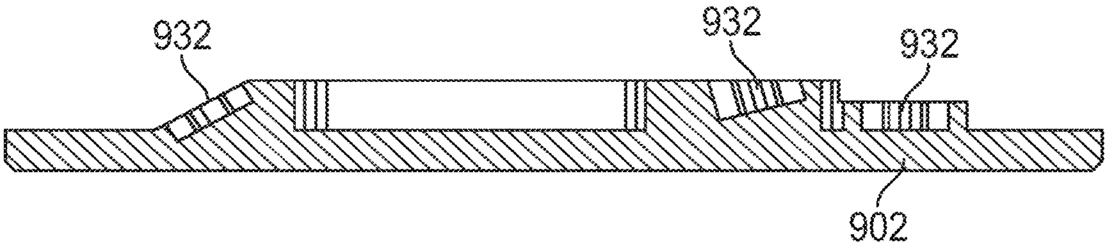

FIGS. 9A, 9B, and 9C illustrate another arrangement 900 of elongate transducer elements 402 that need not be arranged linearly in a row, such as shown and described with respect to FIGS. 7A-7D and FIGS. 8A-8D. Instead, as shown conceptually in a high-level top view of FIG. 9A, the arrangement 900 of elongate transducer elements 402A-K can include some transducer elements 402, such as transducer elements 402J-K, that are not aligned with other transducer elements 402, such as other transducer elements 402A-I, and that are even oblique or orthogonal to such other transducer elements 402A-I.

The arrangement 900 of elongate transducer elements 402A-K can be facilitated by such transducer elements 402A-K being affixed to and carried by a transducer carrier 902, which, in turn, can be located on the carrier 102 described herein that can be affixed to a desired limb of a patient. The arrangement 900 of transducers 402A-K shown in FIGS. 9A, 9B, and 9C can include three rows, such as a first row of transducers 402A-C, a second row of transducers 402D-F, and a third row of transducers 402G-I. Each of these rows can include three elongate transducers 402 arranged parallel and side-by-side to each other such as shown in FIG. 9A. At respective ends of the region defined by these three rows of transducers 402 can be located one or more end transducers, such as the end transducers 402J-K. The end transducers 402J-K can be arranged obliquely or orthogonally to the transducers 402 in the three rows. Acoustic barriers 904 can be provided between or about or behind individual ones of the transducers 402, in a manner similar to that described elsewhere herein.

Figure 9D:
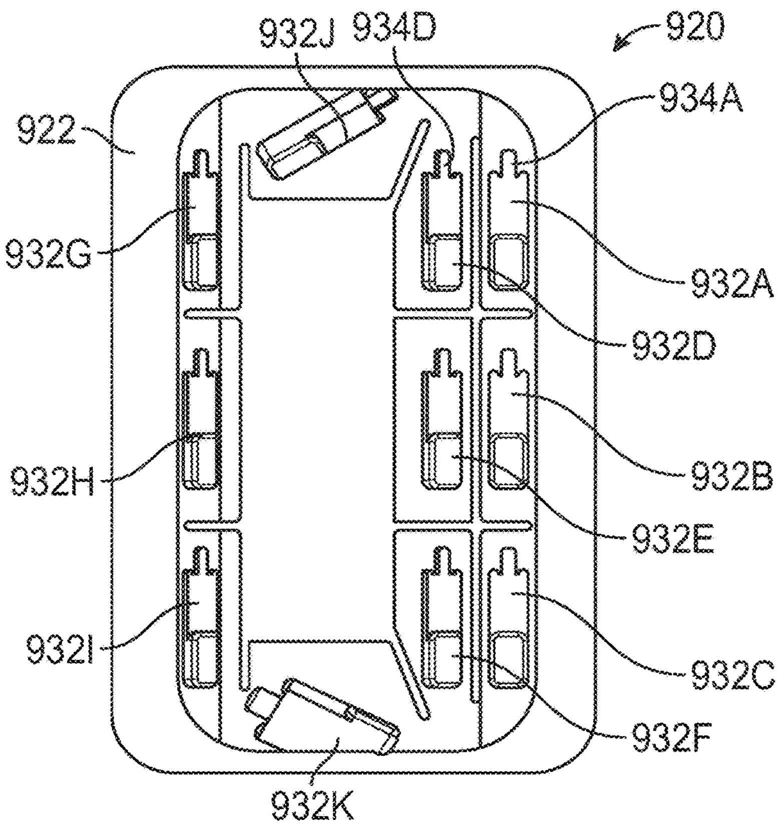
FIGS. 9D-9E show an example of another arrangement 920 of transducers 402 on a transducer carrier 922, similar to the arrangement 900 of transducers 402 on the transducer carrier 902 shown in FIG. 9A, but with some variations.
Figure 9E:
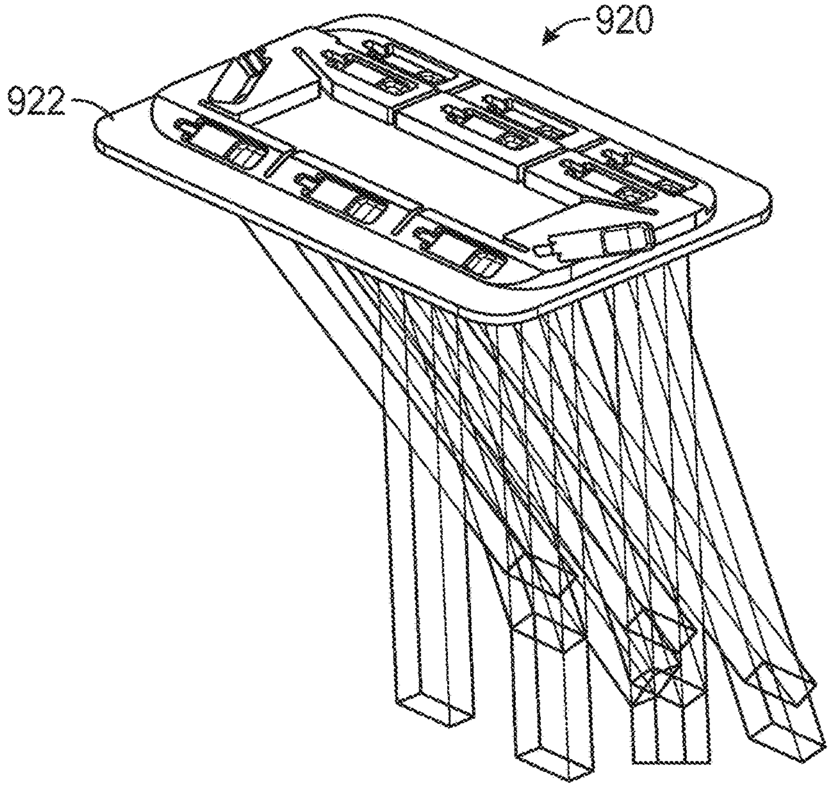

In general, the orientation of the elongate transducers 402 with respect to a direction of blood flow in the blood vessel, can impact the Doppler-shifted echo response signal obtained from a target region in response to insonation of the target region. For example, if a long axis of an elongate transducer 402 is perpendicular to a direction of blood flow in an underlying blood vessel in a target region of interest, that will obtain a relatively higher frequency echo response signal than an elongate transducer 402 having its long axis parallel to a direction of blood flow in the underlying blood vessel in the target region of interest, which will yield a relatively lower frequency echo response signal in comparison. However, the elongate transducer 402 with its long axis perpendicular to the direction of blood flow in the underlying blood vessel in the target region of interest will obtain a relatively smaller signal strength echo response signal than the elongate transducer having its long axis parallel to the direction of blood flow in the underlying blood vessel in the target region of interest, which will yield a relatively higher signal strength in comparison. A transducer arrangement 900, such as shown in FIG. 9A, can help increase or maximize these differences, such as by orienting the transducers 402A-I parallel to each other, and orienting the end transducers 402J-K perpendicular thereto. By contrast, a transducer arrangement, such as shown in FIGS. 9D-9E, in which the end transducers 402J-K are arranged at an oblique angle (e.g., between 30 degrees and 60 degrees, such as 45 degrees, or between 120 degrees and 150 degrees, such as 135 degrees) can obtain some benefit of a higher echo response frequency associated with an elongate transducer 402 having its long axis perpendicular to the direction of blood flow, and can also obtain some benefit of the higher signal strength associated with an elongate transducer 402 having its long axis parallel to the direction of blood flow.

Receptacles can be included in the transducer carrier 902, such as to receive corresponding transducers 402 that can be secured in such receptacles. The receptacles can be arranged so that face portions of the individual transducers 902 can be oriented as desired with respect to a flat plane defined by the transducer carrier 902 or defined by an interface with the subject's skin-either parallel to such a flat plane, or at a desired angle with respect to the flat plane defined by the transducer carrier 902. The arrangement, the angled orientations, the operating frequencies, the intensities of the ultrasound energy employed, and the relative orientation between selected transmit and receive pairs or other combinations or permutations of the transducers 402 can help permit obtaining a targeted insonation region that intersects a blood vessel of interest from which Doppler flow information can be obtained using such selected transducers 402.

For example, as shown in the example of FIG. 9A, one or more of the transducers 402 in the center row of transducers 402 can be configured to act as receive transducers 402, such as in combination with one or more of the other transducers 402, which can be configured to act as transmit transducers.

In FIG. 9A, the top right transducer 402 in the right-most row of transducers 402 can have its face be angled with respect to an interface with the subject's skin and provided with an insonation frequency to insonate a target region that is between 20 millimeters and 40 millimeters deep, in combination with one or more of the center row of transducer elements 402 acting in a receive mode. The right-most transducer 402 that is to the right of and, in the example of FIG. 9A, is shown as orthogonal to the right-most row of transducer elements 402 can have its face be angled with respect to an interface with the subject's skin and provided with an insonation frequency to insonate a target region that is about 30 millimeters deep, in combination with one of the center row of transducer elements 402 acting in a receive mode. The bottom right transducer 402 in the right-most row of transducer 402 can have its face be angled with respect to an interface with the subject's skin and provided with an insonation frequency to insonate a target region that is between 3 millimeters and 20 millimeters deep, in combination with one or more of the center row of transducer elements acting in a receive mode. The left-most transducer 402 that is to the left of and, in the example of FIG. 9A, is shown as orthogonal to the left-most row of transducer elements 402, can be angled and provided with an insonation frequency to insonate a target region that is about 10 millimeters deep, in combination with one of the center row of transducer elements acting in a receive mode. The left-most row of transducers 402 can be oriented with their respective faces parallel to an interface with the subject's skin, such as to define respective orthogonal axis that are perpendicular to the face plane of such a transducer 402, such that the orthogonal axis is also perpendicular to the front face of the transducer 402 and to the plane of the underlying skin of the subject, located behind the back surface of the transducer carrier 902.

As shown in FIG. 9C, the transducer carrier 902 can include or consist of a material having suitable structural and acoustic properties. In an example, the transducer carrier 902 can include or consist of polystyrene. Polystyrene can provide suitable structural support. Polystyrene can also have a suitably low acoustic impedance, which can help in impedance matching between the acoustic impedance of the transducer 402 and the subject's skin. To illustrate, if a transducer 402 has an acoustic impedance of 10 MegaRayles, and the subject's skin and body have an acoustic impedance of 1.5 MegaRayles, then it can be desirable to have an intervening material located therebetween, wherein the acoustic impedance of the intervening material is at a value that is at or near a geometric mean between the transducer acoustic impedance (e.g., 10 MegaRayles) and the body acoustic impedance (e.g., 1.5 MegaRayles). In this example, the intervening material having an acoustic impedance at or near the geometric mean of 3.87 MegaRayles, which can help reduce or avoid acoustic reflections in the intervening material. This, in turn, will help more of the acoustic energy be transmitted or received through the intervening material between the body and the transducers 402. Also, a thickness of the intervening portion of the polystyrene or other material of the transducer carrier 902 can be an odd positive integer multiple of $\lambda/4$, where $\lambda$ represents the wavelength associated with the RF ultrasound frequency being transmitted from or received by a transducer 402. This can also help reduce or avoid acoustic reflection at an interface with the intervening polystyrene portion of the transducer carrier 902.

FIGS. 9D-9E show an example of another arrangement 920 of transducers 402 on a transducer carrier 922, similar to the arrangement 900 of transducers 402 on the transducer carrier 902, but with some variations. In FIG. 9D, the end transducers 402J and 402K can be oriented obliquely to the other transducers 402A-I, rather than orthogonally thereto as shown in FIG. 9A. This is shown in FIG. 9D by the obliquely angled transducer receptacles 932J-K that are arranged to receive transducers 402J and 402K, respectively. In FIG. 9D, the other receptacles 932A-I can be arranged in rows to receive corresponding transducers 402A-I, such as shown in FIG. 9A. For example, the obliquely angled elongate transducers 402J and 402K can define longitudinal axes that can respectively be obliquely angled at 45 degrees and 135 degrees respectively with respect to a longitudinal axis defined by one of the rows of elongate transducers 402A-I, which are shown in FIG. 9D by their corresponding receptacles 932A-I.

As explained above, a transducer arrangement, such as shown in FIGS. 9D-9E, in which the end transducers 402J-K are arranged at an oblique angle (e.g., between 30 degrees and 60 degrees, such as 45 degrees, or between 120 degrees and 150 degrees, such as 135 degrees) can obtain some benefit of a higher echo response frequency associated with an elongate transducer 402 having its long axis perpendicular to the direction of blood flow, and can also obtain some benefit of the higher signal strength associated with an elongate transducer 402 having its long axis parallel to the direction of blood flow. In sum, the arrangement of the end transducers 402J-K with respect to the array of parallel transducer 402A-I can help ensure that the insonation and receive fields will appropriately intersect and yield a suitable signal from a blood vessel located in a target region of interest in the underlying subject.

FIG. 9E is an isometric view of the arrangement 920 and the transducer carrier 922 shown in FIG. 9D, showing directionality of the transmit or receive beams associated with the respective transducers 402A-K. In the example shown in FIGS. 9D and 9E, the receptacles 932G-I can be angled such that respective faces of corresponding transducers 402G-I are oriented at a 30 degree angle (e.g., slanted toward a central longitudinal axis of the transducer carrier 922 as shown in FIGS. 9D-9E) with respect to an interface with the subject's skin, such as can be parallel to an underside planar face of the transducer carrier 922. Similarly, the receptacles 932D-F can be angled such that respective faces of corresponding transducers 402D-F are oriented at 15 degree angle (e.g., (e.g., slanted toward a central longitudinal axis of the transducer carrier 922 as shown in FIGS. 9D-9E) with respect to an interface with the subject's skin, such as can be parallel to an underside planar face of the transducer carrier 922. The receptacles 932A-C can be oriented such that respective faces of corresponding transducers 402A-C can be parallel to an interface with the subject's skin, such as can be parallel to an underside planar face of the transducer carrier 922. The receptacle 932J can be oriented such that the face of corresponding transducer 402J received therein can be angled with respect to an interface with the subject's skin, such as can be parallel to an underside planar face of the transducer carrier 922, such that a targeted area of interest associated with the transducer 402J is approximately 30 millimeters beneath the surface interface with the subject's skin. The receptacle 932K can be oriented such that the face of corresponding transducer 402K received therein can be angled with respect to an interface with the subject's skin, such as can be parallel to an underside planar face of the transducer carrier 922, such that a targeted area of interest associated with the transducer 402K is approximately 10 millimeters beneath the surface interface with the subject's skin. The particular locations and angles shown in the arrangement 920 are merely illustrative examples. Other locations and angles are also possible.

In FIGS. 9A-9E, individual ones of the various transducers 402 can have locations and angles that can be different from other individual ones of the various transducers 402, but that fixed by the particular arrangement of the transducers 402 within the transducer carrier 902. Different angles of one or both of the transmit or receive transducers 402 may yield different blood flow velocity estimates. The blood vessel of interest may fall within multiple areas of intersection of more than one transmit/receive pair (or other combination) of the transducers 402. In such a situation, such multiple pairs (or other combinations) of the transducers can be used to perform a particular measurement, and these individual measurements can be combined by signal-processing circuitry, such as to determine a mean or other central tendency of such individual measurements from corresponding particular pairs or other combinations of individual transducers 402. Spread information, such as variance or standard deviation, can also be determined, such as for use in selecting a particular pair or other combination of transducers 402 for using measurements from that selected pair or combination of transducers 402. A particular subset of a pair or other combination of transducers 402 can additionally or alternatively be selected or ranked based on signal strength of the RF response signal or the audio response signal.

In FIGS. 9D and 9E, each of the receptacles 932A-K is shown as having a optional corresponding lateral bondwire access pathway 934. Each of the piezoelectric transducers 402A-K can include electrical terminals on each of its opposing faces for providing electrical input and return paths for each transducer 402A-K. For good performance, each transducer 402A-K should be seated flat within its corresponding receptacle 932A-K. While the wire bonds attached to the rear faces (facing away from the subject) of such transducers 402A-K are easily accessible and do not interfere with proper seating of the transducers 402A-K within their corresponding receptacles 932A-K, the wire bonds attached to the front faces (facing toward the subject) of such transducers 402A-K can interfere with proper seating of the transducers 402A-K within their corresponding receptacles 932A-K in the absence of providing respective lateral bondwire access pathways 934. But by providing respective lateral bondwire access pathways 934 for corresponding receptacles 932, a flatter seating of the transducer 402 within a receptacle 932 can be obtained, which can significantly help improve the performance of the transducers 402.

As shown in FIGS. 9D, 9E, the lateral bondwire access pathways 934 can include respective recesses extending laterally from the recessed receptacles 932A-K into which the corresponding transducers 402A-K are inserted. The recesses provided by the lateral bondwire access pathways 934 can be wide enough to accommodate a bondwire thickness of the bondwire that is affixed to a patient-facing face of the corresponding transducer 402 for providing electrical and mechanical contact thereto. The recesses provided by the lateral bondwire access pathways 934 can be long enough to accommodate a curving away of the bondwire passing therethrough, such as to accommodate a gentle curve of the bondwire (without breaking the bondwire or dislodging its connection from the patient-facing face of the corresponding transducer 402) through 90 degrees, from a lateral direction from the transducer 402 toward a direction that faces away from the patient, such that the bondwire can be electrically and mechanically connected to a printed circuit board that can be located above the transducer carrier 922 in a direction that is away from the patient.

Figure 10A:
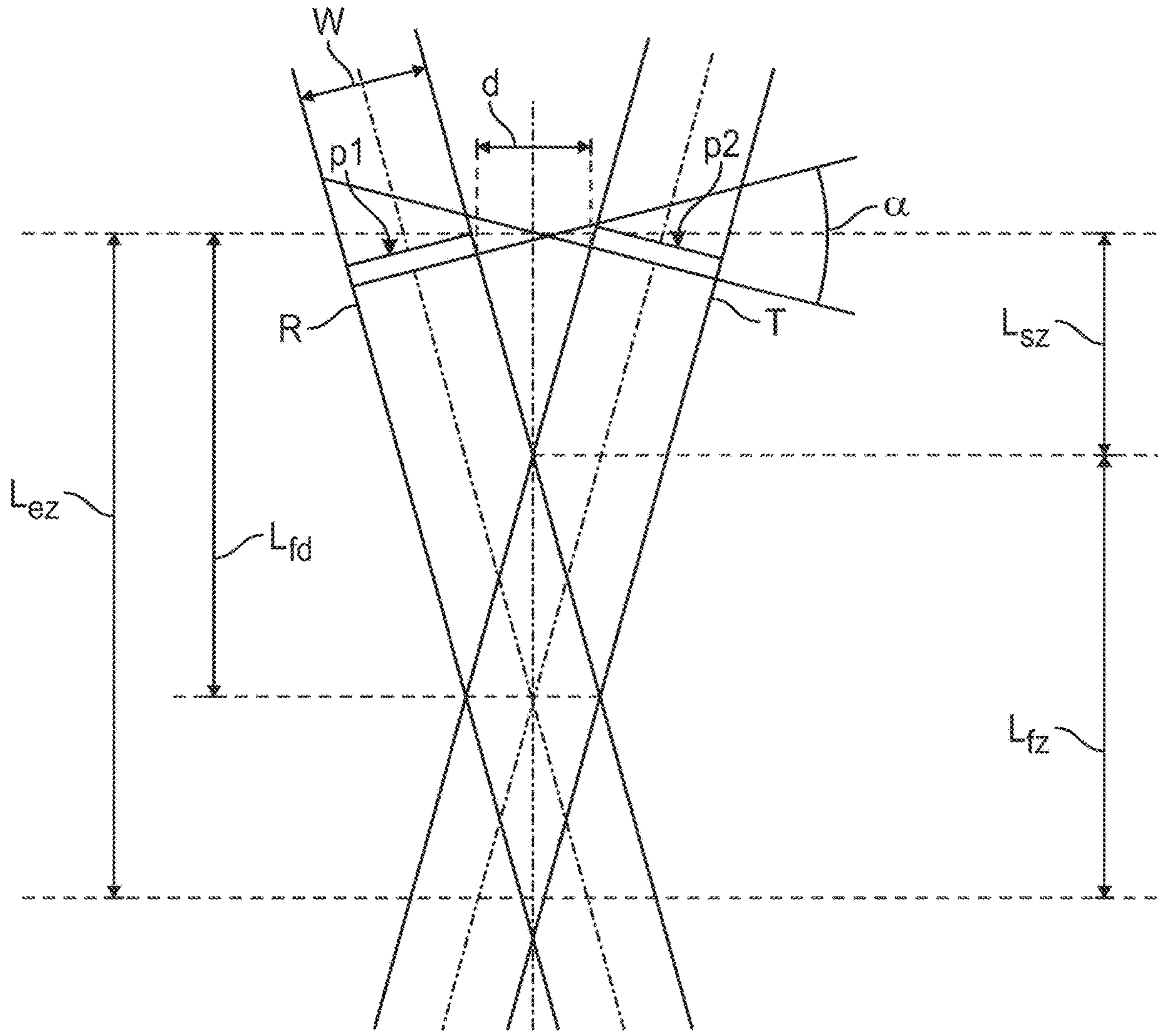
FIGS. 10A, 10B, and 10C together provide an illustrative example of selectively addressing of individual ones, pairs, groups, permutations, or combinations of the transducer elements.
Figure 10B:
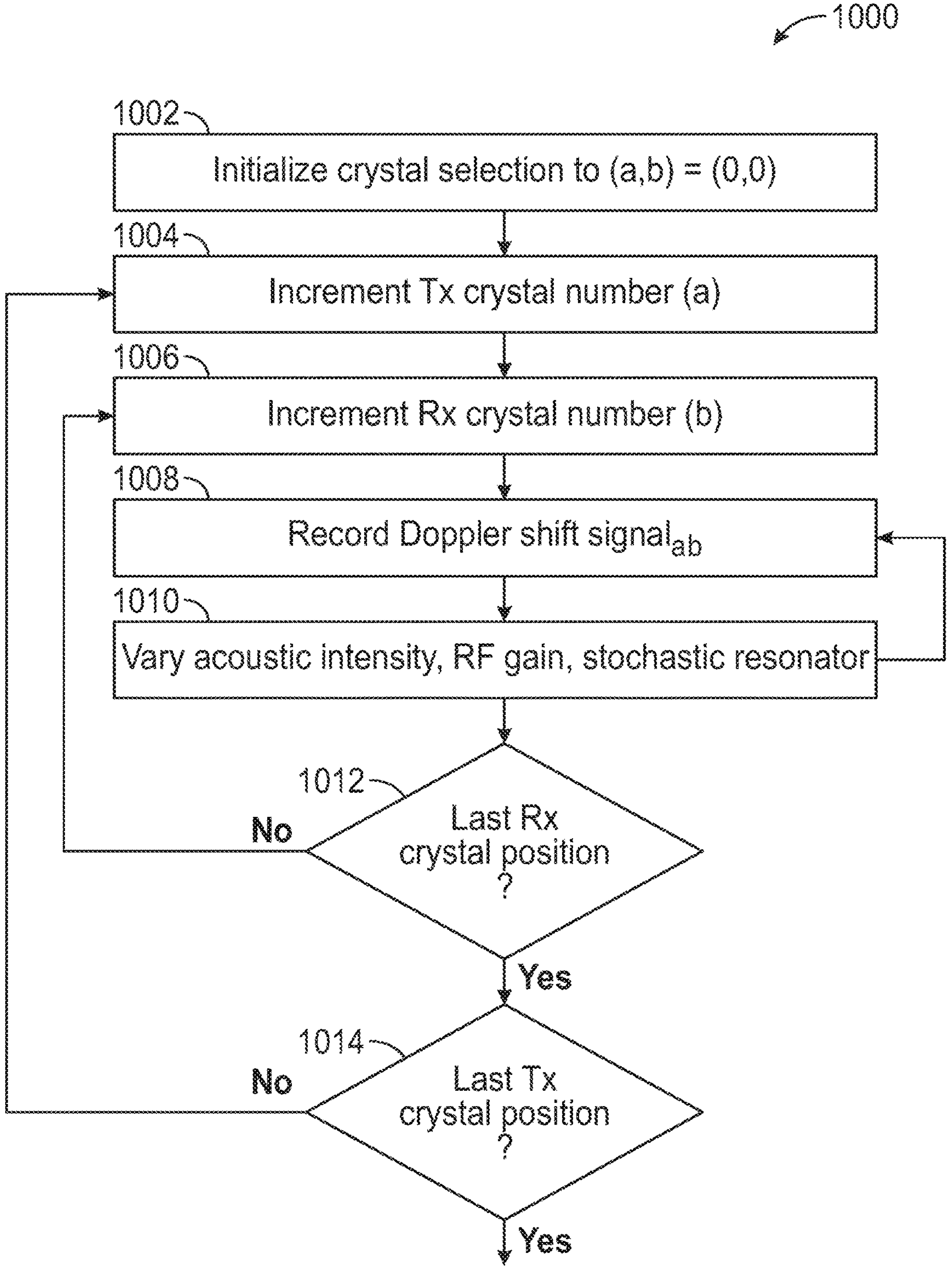
Figure 10C:
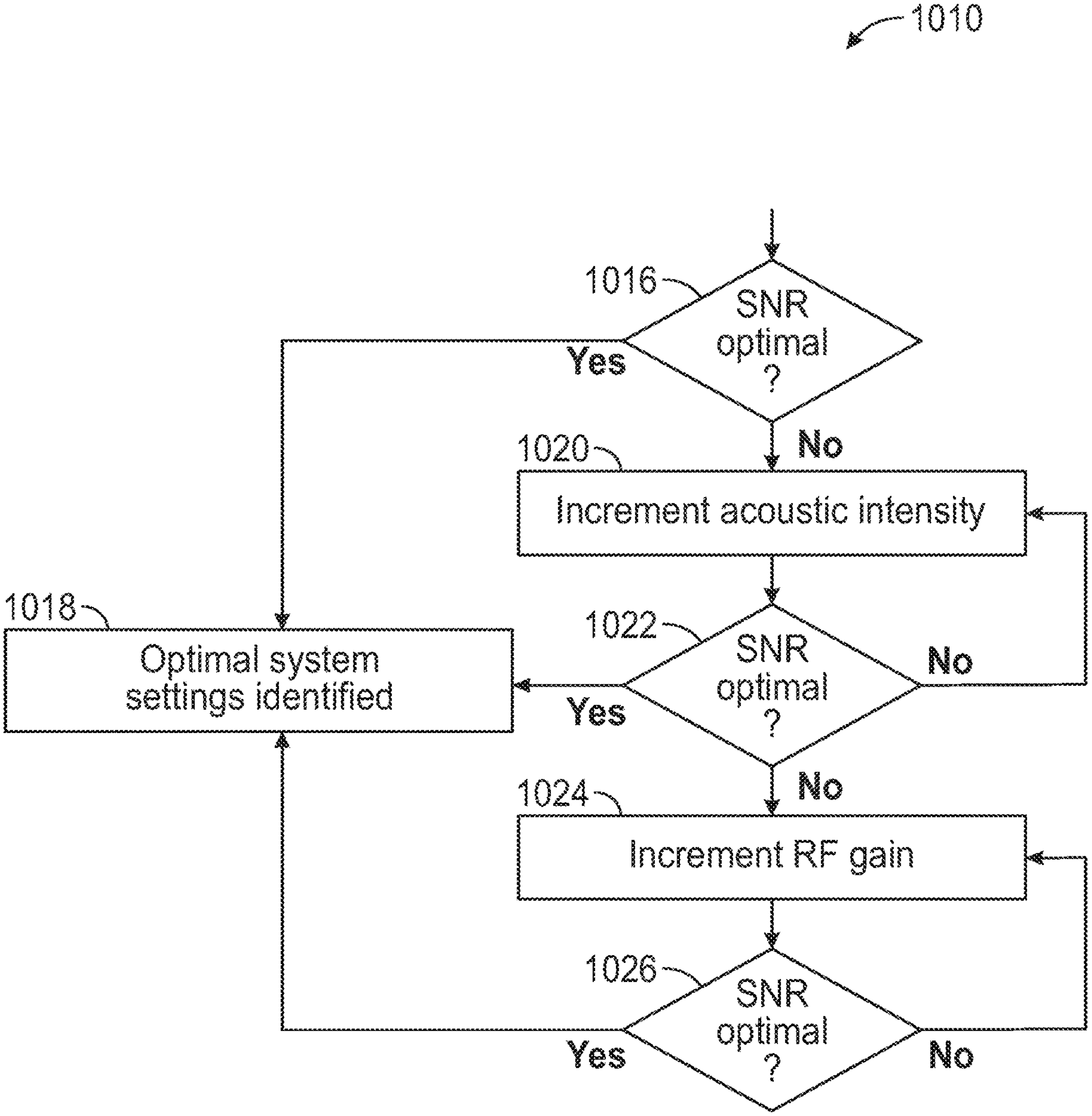

FIGS. 10A, 10B, and 10C together provide an illustrative example of selectively addressing of individual ones, pairs, groups, permutations, or combinations of the transducer elements, such as can include using one or more control signals from the controller circuitry 308 or the transducer interface circuitry 306, or both, for performing the selective addressing to obtain a desired target region of interest at an appropriate depth and location for acquiring Doppler blood flow information from a target region of interest, such as at various depths below the surface of the subject's skin. Such selective addressing can via an arrangement of transducers 402 on a carrier 102 affixed to the patient can make the task of acquiring such information much easier than otherwise would be the case using a handheld ultrasound Doppler probe, particularly by an inexperienced healthcare provider operator.

FIG. 10A shows an arrangement of two piezoelectric transducer elements, similar to that shown and described with respect to the left-hand portion of FIG. 1.

For a particular patient, the blood vessel 200 of interest is located at an unknown depth below the skin surface of the patient. FIG. 10A shows an arrangement of Doppler piezoelectric transducer elements p1 and p2, which can also be referred to as PZT crystals. One of the piezoelectric transducer elements p1 and p2 can be configured to operate in a transmit mode as an ultrasound transmitter. The other of the piezoelectric transducer elements p1 and p2 can be configured to operate in a receive mode as an ultrasound receiver. The piezoelectric transducer elements p1 and p2 can be configured (or re-configured) to operate in either one of the transmit mode or the receive mode.

For example, the piezoelectric transducer element p1 can be configured to operate as an ultrasound transmitter, defining an insonation transmit beam having a longitudinal central axis extending orthogonally to a central location on the piezoelectric transducer element p1, having a lateral insonation transmit beamwidth corresponding to a width dimension "w" of p1 that is orthogonal to the longitudinal central axis of the insonation transmit beam being provided by p1, and having an effective insonation transmit depth, $L_{fd}$, below the skin surface that depends on a frequency of the insonation transmit signal provided by p1. The piezoelectric transducer element p2 can be configured to operate as an ultrasound receiver, defining an insonation receive beam having a longitudinal central axis extending orthogonal to a central location on the piezoelectric transducer element p2, having a lateral insonation receive beamwidth "w" corresponding to a width dimension "w" of p2 that is orthogonal to the longitudinal central axis of the insonation receive beam corresponding to p2, and having an effective insonation receive depth, $L_{fd}$, below the skin surface that depends on an insonation receive frequency for which p2 is configured. Using this combination of p1 in transmit mode and p2 in receive mode, an area or volume of intersection between the insonation transmit beam and the insonation receive beam can be defined. This area or volume of intersection is the effective area or volume from which blood flow information can be acquired. To recap, in FIG. 10A, "w" can represent the width of the corresponding PZT crystal transducer elements p1 or p2, "d" can represent a distance between the PZT crystal transducer elements p1 and p2, "α" can represent an angle between the PZT crystal transducer elements p1 and p2, and "$L_{fd}$" can represent a distance between respective ones of the PZT crystal transducer elements p1 and p2 and a center of the target volume corresponding to the arrangement. The focal depth $L_{fd}$ can be represented by the following Equation:

$$L_{fd} = \frac{w + d\cos\left(\frac{\alpha}{2}\right)}{2\sin\left(\frac{\alpha}{2}\right)}$$

In an illustrative, non-limiting example, α=12 degrees, d=0.25 millimeters, w=2.0 millimeters, and $L_{fd}$=10.75 millimeters. By varying w, d, and a, the depth of focus, $L_{fd}$, may be adjusted. By using multiple (e.g., two or more) PZT crystal transducer elements p1 and p2, but with various values of w, d, and α, multiple depths can be examined, multiple locations in a line or plane at such one or more depths can be examined, or both.

FIG. 10B is a flow chart illustrating an example of portions of a method 1000 for selecting among various transducers 402, such as for selectively addressing a pair of transducers 402 such that a first one of the pair of transducers 402 can be configured to operate in a transmit mode for insonating a target region, and the other one of the pair of transducers 402 can be configured to operate in a receive mode, such as for detecting a response from the target region to insonating by the first transducer 402.

At 1002, the piezoelectric crystal selection, from a group of 2 or more transducers 402, can be initialized. For a pair (a, b) of transmit and receive transducers 402 in a group of 2 or more transducers 402, numbered from 1 to n, where n is an integer that is greater than or equal to 2, the initial selection can be set to (0, 0). In FIG. 10B, the first transducer 402 in the ordered pair can represent the transducer 402 selected to operate in transmit mode, and the second transducer 402 in the ordered pair can represent the transducer 402 selected to operate in receive mode. Because the transmit transducer 402 should be different from the receive transducer 402, at least when operating in a continuous wave (CW) mode, the number “a” in the ordered pair should be different from the number “b” in the ordered pair.

At 1004, the index number associated with the transmit transducer can be incremented, such as from 0 to 1.

At 1006, the index number associated with the receive transducer 402 can be incremented, such as from 0 to 2 (because the transmit transducer and receive transducers should be different for CW transducers operating in transmit and receive modes, respectively).

At 1008, the selected transmit and receive transducers 402 are used to insonate a corresponding target region, and to receive a response signal to the insonation. The corresponding Doppler shift signal for the selectively addressed pair (a, b) of transducers 402 is observed and recorded. Then, at 1010, one or more transmit or receive parameters (e.g., intensity, RF gain, stochastic resonance signal injection parameter, etc.) can be varied, and process flow can return to 1008, such as for repeating the insonation and recording of the response to insonation. This can continue for various permutations or combinations of one or more of the transmit or receive parameters. This can then be repeated across the different combinations of non-identical of transducers 402 in a pair (a, b) of transducers 402.

The insonation intensity can be controlled by one or both of the controller 308 or the transducer interface circuitry 306, such as which can adjust an amplitude of an electrical input signal being provided to an acoustic transducer 402 being used for insonation. The particular intensity setting can be based on one or more patient-specific parameters, such as weight, height, Body Mass Index (BMI), or the like. One or more of these can be used as an index in a lookup table or a function that relates the electrical insonation drive signal intensity to one or more of these factors. Additionally or alternatively, a trained statistical learning model can employ artificial intelligence (AI) such as to help select an appropriate electrical insonation drive signal intensity, such as can be based on one or more such factors. Training of the model can involve storing an appropriate electrical insonation drive signal intensity, that yielded an appropriate blood flow signal, in combination with one or more patient-specific parameters for a particular patient from which such data was obtained. In this way, an appropriate acoustic output intensity can be provided, while remaining under a defined maximum allowable acoustic energy level, such as may be specified or required by a regulatory agency or otherwise determined.

At 1012, if not at the index number of the last receive transducer 402 in the arrangement of transducers 402, then process flow can return to 1006 and the receive transducer index can be incremented.

At 1014, if not at the index number of the last transmit transducer 402 in the arrangement of transducers 402, then process flow can return to 1004 and the transmit transducer index can be incremented. At 1014, if the index number of the last transmit transducer 402 has been reached, then the different combinations of transducers 402 in a pair (a, b) of transducers 402 have all been tested, including varying parameters at 1010 in FIG. 10B.

FIG. 10C is a flow chart showing an example of more details of portions of the act of varying parameters at 1010 in FIG. 10B. As shown in FIG. 10C, this can include, at 1016, determining whether a sufficiently large Signal-To-Noise-Ratio (SNR) has been obtained for a given set of operating parameters.

The largest obtainable SNR may be deemed optimal. Such operating parameters can include acoustic intensity, such as can be determined or varied by the controller circuitry 308 or the transducer interface circuitry 306 for controlling other componentry, such as the oscillator 404 and the transmitting element 402A. The operating parameters to be varied can additionally or alternatively include a gain in the system 100, such as the RF gain of the impedance matching RF amplifier 414. The operating parameters to be varied can additionally or alternatively include one or more Stochastic Resonator parameters. For example, these can include one or both of an amplitude or a bandwidth of an audio response enhancement signal, such as can be injected by the audio response signal injection circuit 418, such as described herein.

At 1016, if an optimal SNR can be identified for a particular set of transducers 406 and operating parameters, then process flow can proceed to 1018, where such optimal system settings can be saved in an appropriate location in memory circuitry, such as which can be included in or coupled to the controller circuitry 308. Otherwise, process flow can continue at 1020.

At 1020, acoustic intensity can be adjusted. This can include incrementing acoustic intensity to a higher-intensity setting in a set of multiple intensity settings. This can be performed by the controller circuitry 308 or the transducer interface circuitry 306 for controlling other componentry, such as the oscillator 404 and the transmitting element 402A.

At 1022, whether an optimal SNR has been attained can again be determined, such as in a similar manner to that described above with respect to 1016. If so, then process flow can proceed to 1018, where such optimal system settings can be saved in an appropriate location in memory circuitry, such as which can be included in or coupled to the controller circuitry 308. Otherwise, if the entire acoustic intensity setting range has not been completed, process flow can return to 1020, and acoustic intensity can again be incremented. If the entire acoustic intensity setting range has been completed, then process flow can continue at 1024.

At 1024, a gain in the system 100 can be varied. This can include incrementing an RF gain of the impedance matching RF amplifier 414, such as to a higher gain setting in a set of multiple available gain settings. At 1026, whether an optimal SNR has been attained can again be determined, such as in a similar manner to that described above with respect to 1016. If so, then process flow can proceed to 1018, where such optimal system settings can be saved in an appropriate location in memory circuitry, such as which can be included in or coupled to the controller circuitry 308. Otherwise, if the entire RF gain range has not been completed, process flow can return to 1024, and RF gain can again be incremented. If the entire RF gain range setting has been completed, and the SNR is still unsatisfactory, then one or more Stochastic Resonator parameters can be varied. This can include varying one or both of an amplitude or a bandwidth of an audio response enhancement signal, such as can be injected by the audio response signal injection circuit 418, such as described herein.

Figure 11:
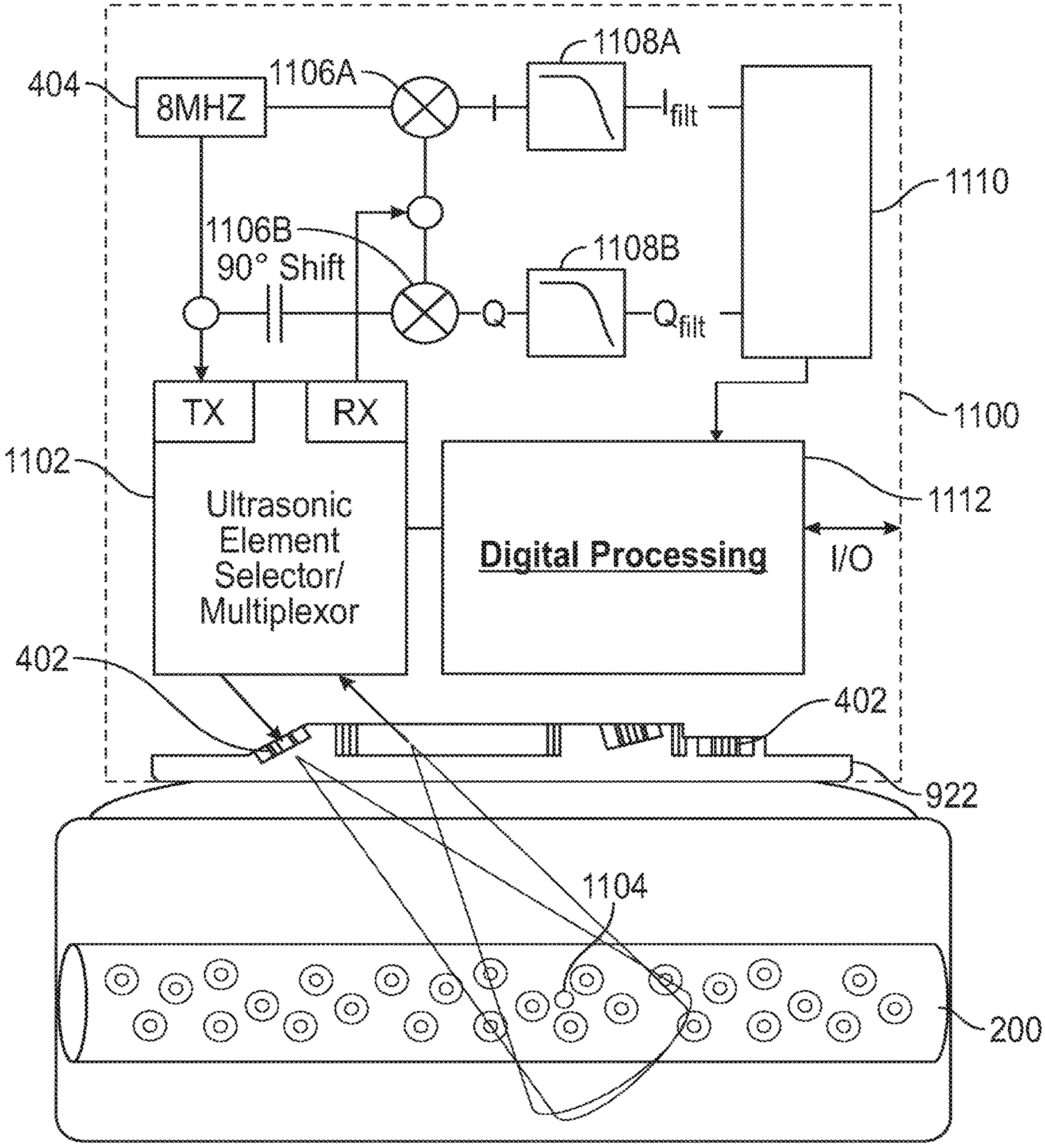
FIG. 11 is a block diagram illustrating generally an example of portions of the system that can include bidirectional Doppler flow velocimetry that can distinguish between different directions of blood flow within a target blood vessel of interest.

FIG. 11 is a block diagram illustrating generally an example of portions of the system 100 that can include bidirectional Doppler flow velocimetry that can distinguish between different directions of blood flow within a target blood vessel of interest 200. The system 100 can include an electronics unit 1100. The electronics unit 1100 can be located on the carrier 102. The electronics unit can include transducers 402, such as can be arranged and variously oriented and carried onboard a multi-element array transducer carrier 902, such as described with respect to FIGS. 9A, 9B, and 9C. An ultrasonic element selector or multiplexor 1102 can be included in the electronics unit 1100, such as with the transducer interface circuitry 306, the controller circuitry 308, or both. The multiplexor 1102 can be used to select a pair (a, b) of transducers 402 for operating in a transmit mode (TX) and a receive mode (RX) respectively. The multiplexor 1102 can route a transducer energizing signal from an oscillator 404 to the selected transmit transducer 402 for producing the resulting insonation toward the target volume 1104. The multiplexor 1102 can route a resulting response signal from the target volume 1104, received from a selected receive transducer 402, such as for one or more of signal pre-processing, signal acquisition, or signal-processing.

Amplifiers and mixers 1106A-B can be included in the electronics unit 1100. The amplifier/mixer 1106A can receive an output signal from the oscillator 404, which can be mixed with the received response signal from the selected receive transducer 402 for producing an in-phase mixed signal component, I. The amplifier/mixer 1106B can receive a 90 degree phase-shifted output signal from the oscillator 402, which can be mixed with the received response signal from the selected receive transducer 402 for producing a phase-quadrature mixed signal component, Q. The mixed signal components I, Q can respectively be filtered, such as by corresponding lowpass filter circuits 1108A-B, to produce corresponding filtered signals $I_{filt}$, $Q_{filt}$. The resulting filtered analog signals $I_{filt}$, $Q_{filt}$, can be provided to a dual-channel or other analog-to-digital converter (ADC) 1110 and converted into corresponding digital signals. The resulting corresponding digital signals can be provided to Digital Signal Processing (DSP) circuitry 1112, such as for decomposing the digitized filtered I, Q signals into forward flow and reverse flow signals, for performing frequency analysis, and for being communicated from the carrier 102 to the user interface 104, such as by corresponding wireless transceiver circuit 310 on the carrier 102 and the wireless transceiver circuit 110 on at the user interface 104. Further processing can be performed at the user interface 104, such as by the processor 112. Information from such further processing can be displayed on the display 106. An audio Doppler flow signal can be played on the audio speaker 108.

Figure 12:
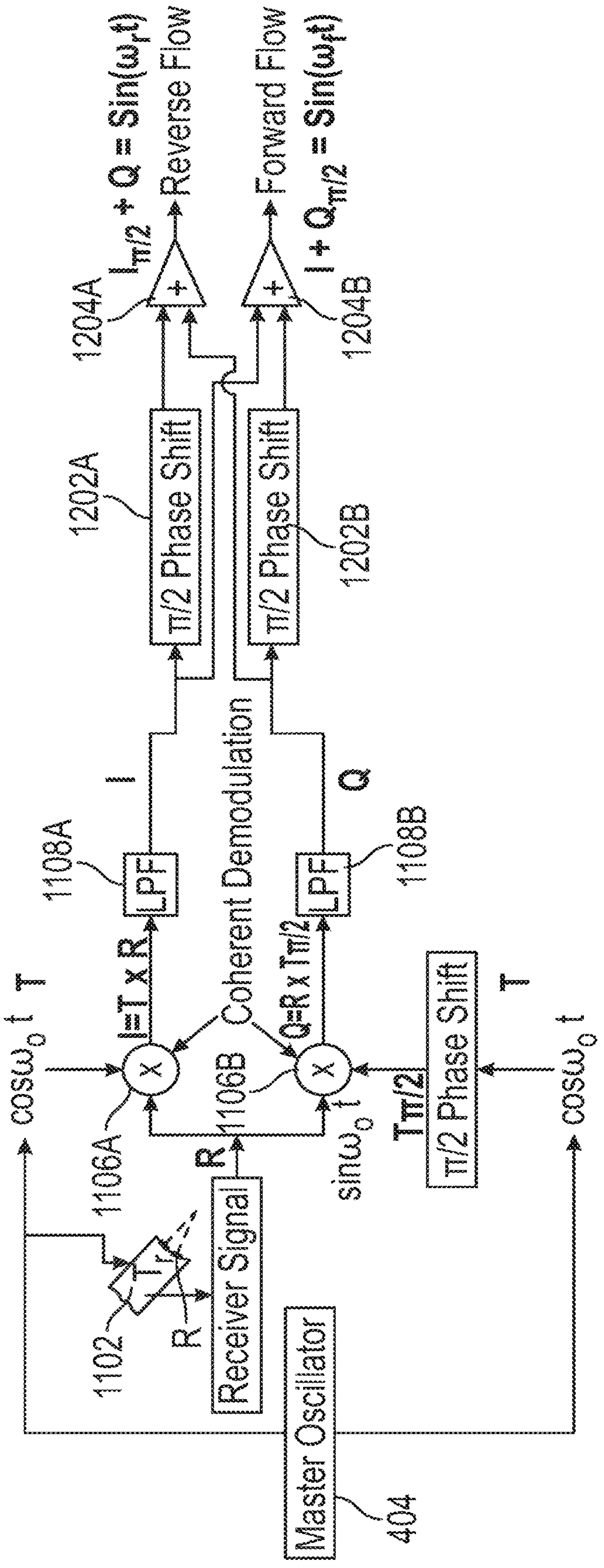
FIG. 12 is a block diagram illustrating generally more details of bidirectional flow determination, such as which can be used to provide the flow direction discrimination shown in FIG. 4.

FIG. 12 is a block diagram illustrating generally more details of bidirectional flow determination, such as which can be used to provide the flow direction discrimination 416 of FIG. 4. This can be useful for, among other things, distinguishing arterial flow from venous flow, such as to help ensure that an arterial blood pressure measurement is appropriately associated with an artery, not a vein, in which the direction of arterial blood flow will generally be toward a more distal portion of the limb, whereas the direction of venous blood flow will generally be toward a more proximal portion of the limb. In an elongate handheld Doppler flow device approach, the Doppler transducer is oriented by the user to be roughly parallel to the long axis of the blood vessel. In such an approach, arterial flow will be located on one audio output channel, and venous flow will be located on a different second audio output channel, because venous and arterial blood flow in opposite directions. However, in such an approach, it can be difficult to identify the orientation of the blood vessel. While limb arteries often run somewhat parallel to the limb itself, this is not always the case. Thus, separating arterial and venous flow by direction using a handheld Doppler flow device can sometimes fail or be difficult. By contrast, the present approach can identify the direction of the blood vessel with respect to the limb. As explained herein, the present approach can involve searching for a combination of piezoelectric transducers 402 that yields the highest Doppler-shift frequency. This combination can define the geometry or orientation of the blood vessel path, as explained herein. Such information can be recorded, displayed, or used for further signal processing, such as described herein.

In FIG. 12, the filtered I, Q signals can respectively be phase-shifted by 90 degrees by corresponding phase shift elements 1202A-B. The resulting phase shifted signals can be provided to corresponding summing amplifiers 1204A-B, each of which can also receive the non-phase-shifted signal from the other of the filtered I, Q signals for summing. The corresponding outputs from the summing amplifiers 1204A-B can provide respective signals representing reverse flow and forward flow. The respective signals representing reverse flow and forward flow can be provided, such as via separate audio channels, to the audio speaker 108. This can permit separate verification of each, such as by a healthcare provider user listening to the resulting sound signal or by a device or algorithm serving as a proxy for such a healthcare provider user. Portions of the signal processing shown in FIG. 12 can be performed either in the analog domain or the digital domain. For example, the 90 degree phase shift performed by corresponding phase shift elements 1202A-B can include using Infinite Impulse Response (IIR) or other digital filters capable of providing such 90 degree phase shift digitally via a Hilbert transform.

FIGS. 11-12 show componentry that can include frequency mixers 1106A-B. Such mixers 1106A-B can receive signal inputs at two different frequencies, $f_1$ and $f_2$ and, in response, can produce sum ($f_1+f_2$) and difference ($f_1-f_2$) signal outputs. Types of mixers can include a passive mixer (e.g., using one or more diodes) or an active mixer (e.g., using transistors or an integrated circuit). A mixer can further be configured as unbalanced (input signals are not galvanically isolated or ground-referenced), single balanced (one of the two input signals is galvanically isolated), or double balanced (each one of the two input signals is galvanically isolated). Using a double balanced suppressed carrier frequency mixer 1106A-B can offer potential advantages, such to help suppress distortion products, carrier frequency feedthrough, and unwanted frequency sidebands. Any of these could otherwise propagate through the system and manifest in the resulting sound signal played by the audio speaker 108 as background noise (e.g. "hiss"). Such background noise can mask a true blood flow Doppler shift signal—particularly when such a true blood flow Doppler shift signal is weak, such as may be the case in a PAD patient.

Figure 13:
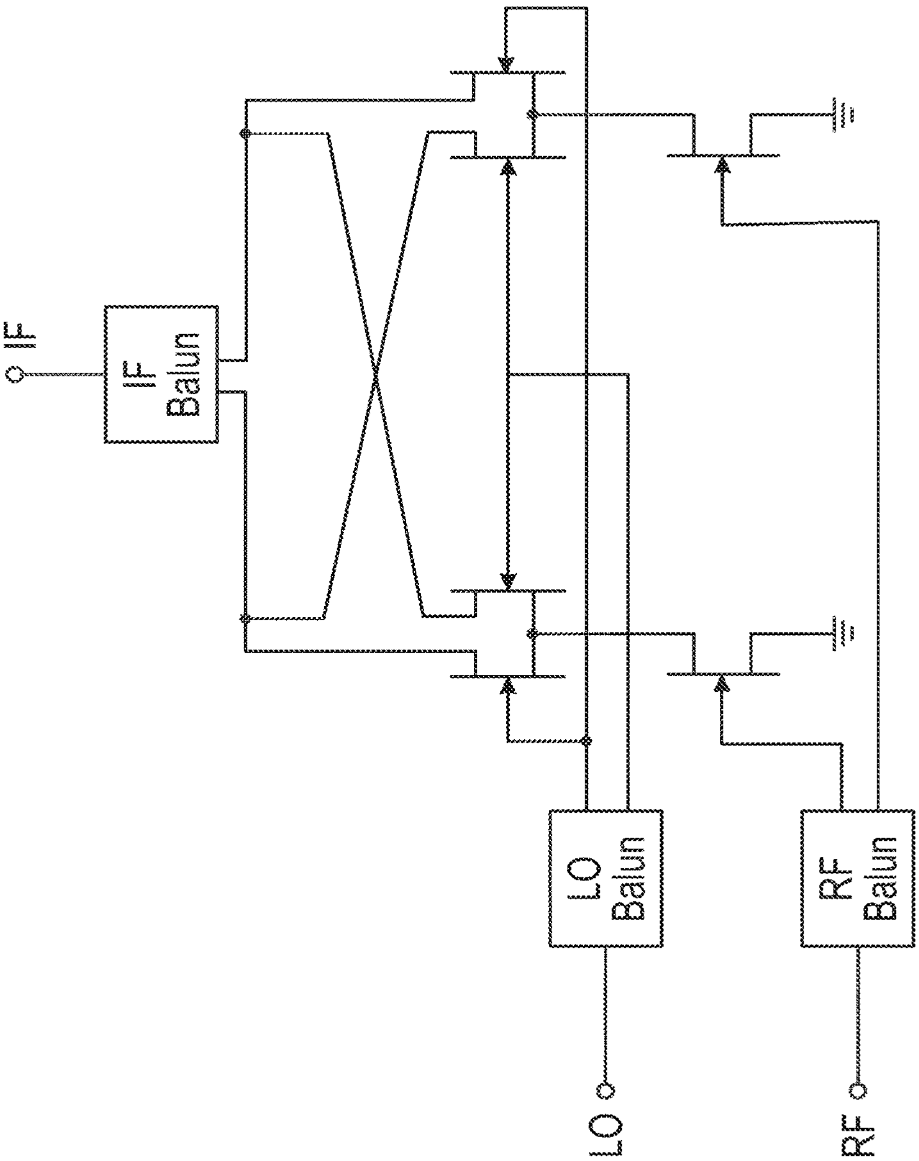
FIG. 13 is a schematic diagram of an illustrative example of a double-balanced mixer configuration.

A basic double-balanced mixer, can include four Schottky diodes, such as in a quad ring configuration. The baluns or hybrids can be located at both the radio frequency (RF) and local oscillator (LO) input ports, and the IF signal can be tapped off from the RF balun. In operation a double balanced mixer has a high level of LO-RF isolation and LO-IF isolation and it provides a reasonable level of RF-IF isolation. Using double balanced mixers can help reduce the level of intermodulation products by up to 75% when compared to a single diode unbalanced RF mixer. Like the single balanced mixer, the double balanced mixer can also be replicated using balanced modes of operation within field-effect transistor (FET) or other transistor circuit designs. When included within an integrated circuit, a double balanced mixer configuration can be included at negligible increase in cost. An illustrative example of a double-balanced mixer configuration is shown in FIG. 13.

Wearables. Modularity, and Mechanical Componentry Examples

FIG. 1 showed an example of portions of a system 100, such as can include a user interface 104, inflatable cuffs 103, and corresponding carriers 102. As shown in FIG. 3, the carriers 102 can include transducers and an electronics unit. As explained herein, some control and processing functionality can be performed at the carrier 102, other control and processing functionality can be performed at the user interface 104, or elsewhere. Similarly, the componentry of the system 100 can include variations in partitioning of such componentry, as well as variations in wearable or other affixation devices employed, and various user input/output devices such as which can present information or content to a user in a variety of different ways.

Figure 14:
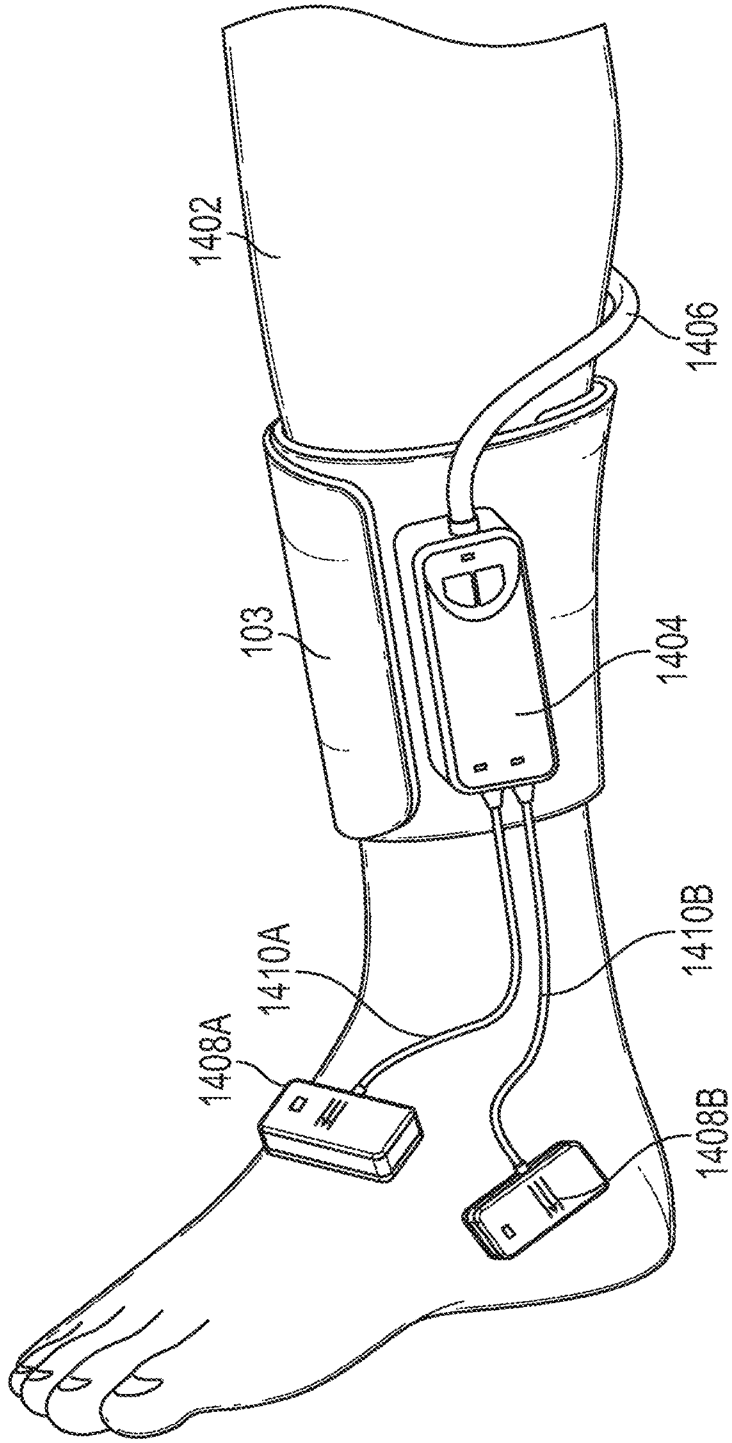
FIG. 14 shows an illustrative example of portions of a modular system, having a different partition of componentry, and showing portions of a possible environment in which it can be used.

FIG. 14 shows an illustrative example of portions of a modular system 100, having a different partition of componentry, and showing portions of a possible environment in which it can be used. FIG. 14 shows an example in which a cuff 103 can be worn on a left leg 1402 of a patient. An auxiliary unit 1404 can be attached to the cuff 103, such as by VELCRO hook-and-loop fastener or otherwise. The auxiliary unit 1404 can include an electronics unit, such as described herein with respect to the carrier 102, as well as a pump in fluid communication with the cuff 103 for inflating the cuff 103. The auxiliary unit 1404 can be connected to the cuff 103 by a pressure tube 1406, which can convey pressure from the pump in the auxiliary unit 1404 to the cuff 103 for inflating the cuff 103. The electronics unit in the auxiliary unit 1404 can include controller circuitry 308, cuff interface circuitry 302, or the like for controlling the pump for inflating the cuff 103.

FIG. 14 shows an example in which the system can also include one or multiple acoustic transducer carriers 1408. The transducer carriers 1408 can be tethered to the auxiliary unit 1404, such as by corresponding multi-conductor or other suitable electrical cables 1410, or can be wirelessly coupled thereto. An individual one of transducer carriers 1408 can include an array or other arrangement of transducers 402, such as described herein. Control and signal processing electronics for such transducer 402 can be included in the auxiliary unit 1404, in the transducer carriers 1408, or partitioned between the two. The auxiliary unit 1404 can include a wireless communication transceiver, such as for communicating wirelessly with the user interface 104, as explained herein. The auxiliary unit 1404 can include a battery or other power source, such as for powering the pump, the electronics, or both. The arrangement shown in FIG. 14, with two transducer carriers 1408A-B, can permit concurrent, sequential, or other insonation, interrogation, and analysis from multiple different locations on the patient, which can help yield accurate results more quickly and with less need to re-position the transducer carriers 1408 to obtain the desired Doppler flow measurements. The transducer carriers 1408 can include multiple portions, such as to help affixation, acoustic impedance matching, and to better partition re-usable and single-use disposable components, such as to help meet sanitary objectives in making measurements from different patients. The various components, such as the auxiliary unit 1404, and the transducer carriers 1408 can respectively include LED or other indicator lights, displays, or the like, such as to help communicate information to the end-user.

For example, as explained herein, the present approach can involve searching for a combination of piezoelectric transducers 402 that yields the highest Doppler-shift frequency. This combination can define the geometry or orientation of the blood vessel path, as explained herein. Such information can be recorded, displayed, or used for further signal processing, such as described herein. Such displayed information can be displayed on the display 106 of the user interface 104. Additionally or alternatively, such displayed information can also be provided on a display that can be included on the auxiliary unit 1404, or on a display included on the transducer carrier 1408, or both. For example, FIG. 14 depicts arrows that can be displayed on respective displays associated with the transducer carriers 1408A, 1408B, such as to provide blood flow direction or other information to the user. This can effectively provide the user with Doppler blood flow tomography information, such as which can include blood flow direction or other information, which can be helpful to the user in locating, positioning, re-positioning, or using the transducer carriers 1408A-B.

The respective displays that can be included on the transducer carriers 1408A-B can include a color, backlit, high resolution display that shows a path of blood flow. Other information can also be included and displayed on such a display, or on the display 106. Such other displayed information can include, among other things, a depth (below the skin) of the targeted blood vessel. As explained herein, triangulation can be used to locate the targeted blood vessel, such as by employing various combinations of transducer pairs, such as to help perform such triangulation. The system 100 can use the different Doppler shift frequencies measured from each pair (or other combination) of transducers 402 to calculate the path of the blood flow through the blood vessel. The signal strength of the received echo Doppler response signal from each of the differently positioned transducers 402 can be used to infer the depth of the targeted blood vessel.

Figure 15A:
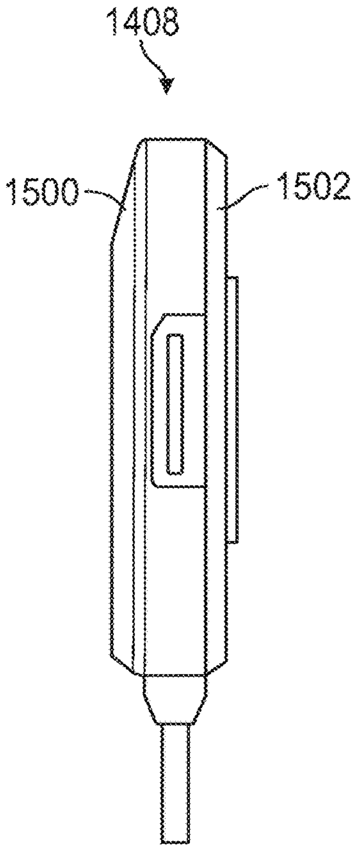
FIGS. 15A, 15B, and 15C show an example of portions of a transducer carrier.
Figure 15B:
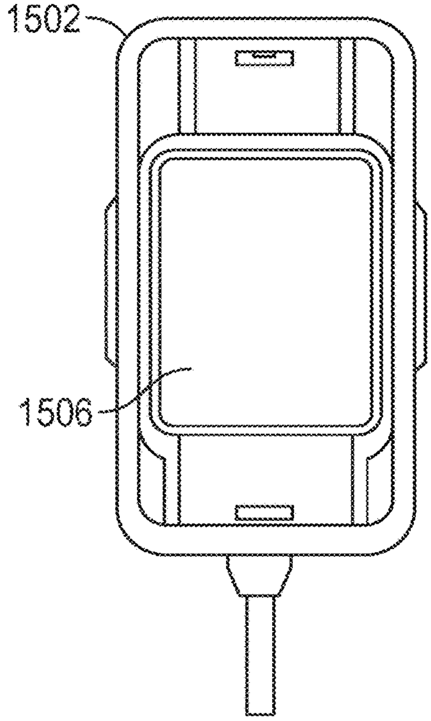
Figure 15C:
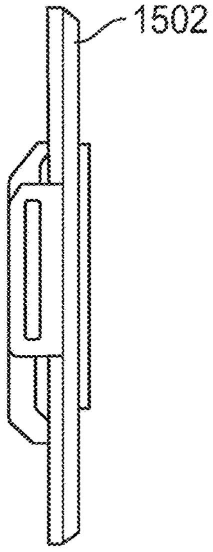

FIGS. 15A, 15B, and 15C show an example of portions of a transducer carrier 1408. FIG. 15A is a side view, showing a reusable transducer housing 1500, such as which can include transducer elements 402, transducer control or signal processing electronic circuitry, or both. The side view of FIG. 15A also shows a base 1502, into which the transducer housing 1500 can be end-user-attached, end-user-detached, or both, such as by one or more snap-fitting clips that can be located on the base 1502, on the transducer housing 1500, or both. A patient-facing surface of the base 1502 can include an adhesive tape or other adhesive, such as to help affix the base 1502 to the patient at the desired location. The side view of FIG. 15C shows the base 1502 by itself. The top view of FIG. 15B shows a side of the base 1502 that faces the transducer housing 1500, before snap-fitting engagement between these two components. The base 1502 can also include an acoustic reservoir or acoustic window 1506, which can include a sealed or other gel-pack of acoustic couplant material between a skin-facing surface of the base 1502 or carrier 102 to help provide good acoustic impedance matching for insonation and interrogation by the transducer elements 402. In this example, the base 1502 can be a single-use disposable component, while the transducer housing 1500 and its contents can be a re-usable component.

Figure 16B:
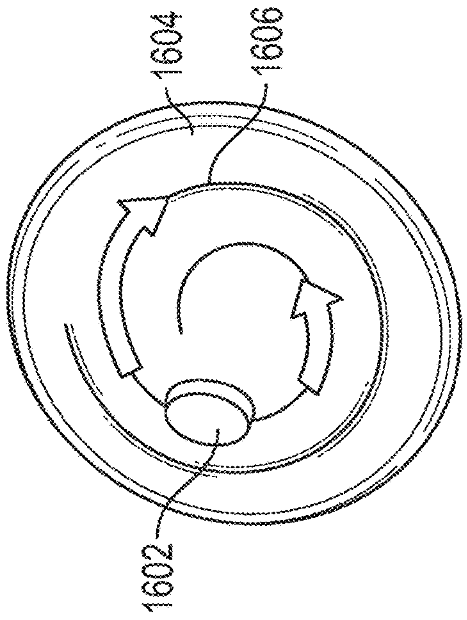
FIGS. 16A, 16B, and 16C show another example of portions of wearable transducer housings and portions of a patient's ankle that can be included in an environment in which they can be used as part of the system.
Figure 16C:
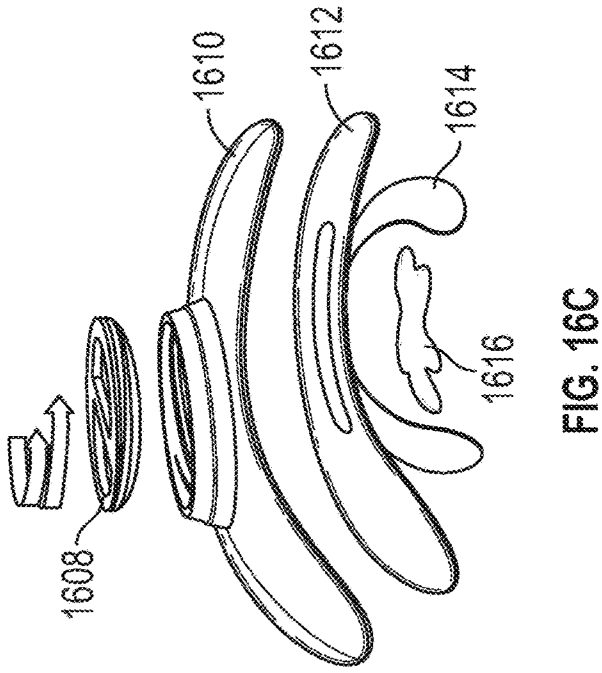
Figure 16A:
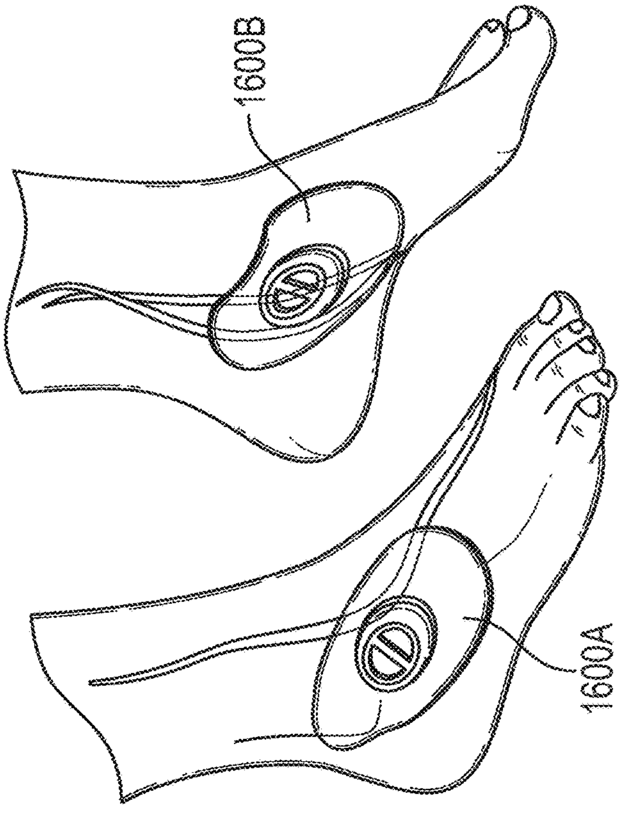

FIGS. 16A, 16B, and 16C show another example of portions of wearable transducer housings 1600A-B and portions of a patient's ankle that can be included in an environment in which they can be used as part of the system 100. FIG. 16A shows an example of wearable transducer housings 1600A-B that can be adhesively fixed near a patient's ankle, which can advantageously take advantage of using the patient's ankle as a biological fiducial marker for locating a region at which the transducer housing 1600 is to be affixed. FIG. 16B shows an ultrasound transducer element or array 1602 that can be located in engagement with a circular, spiral, linear, or other track 1606 in a transducer carrier 1604. This can enable end-user physical movement of the transducer element or array 1602 along the track. The track can include a ramp, such that a movable housing or a stage carrying the transducer element or array 1602 can be re-positioned along the track and, in so doing, can adjust at least one of a transmit angle, a receive angle, or a skin offset distance between a skin surface of the subject and at least one of the acoustic transmitter or the acoustic receiver. This can help permit positioning or re-positioning of the transducer element or array 1602 with respect to the patient by an end-user, either manually or using an electromechanical actuator. FIG. 16C is an exploded view of the transducer housing 1600, showing a twistable transducer carrier 1608 carrying a transducer element or array 1602. The twistable transducer carrier 1608 can be placed within—and rotated with respect to—a corresponding receptacle of abase exterior patch 1610. An underside of the base exterior patch 1610 can include an adhesive, such as to permit affixation to the patient. A peel-away layer 1614 can protect the adhesive from contacting and adhering to another object until the peel-away layer 1614 is removed. An acoustic coupling gel 1616 can be applied to the patient before affixation, or mixed with the adhesive. The acoustic coupling gel 1616 can help provide acoustic impedance matching at the interface with the patient's skin. The adhesive patch transducer housing 1600 can be applied by peeling away the protective peel-away layer 1614 to adhere the adhesive patch transducer housing 1600 to the patient. In an example, the device can include a void or opening through which the acoustic coupling gel 1616 can be administered after affixation to the patient. The Doppler transducer element or array 1602 can be twisted into the receptacle in the exterior patch 1610 such as to obtain a desired location of the transducer element or array 1602 with respect to a target region of the patient to be insonated and interrogated. The transducer element or array 1602 can be translated along the spiral or other track 1606, such as to traverse a spiral pattern during searching for an artery of interest from which Doppler flow information is to be obtained.

Figure 17B:
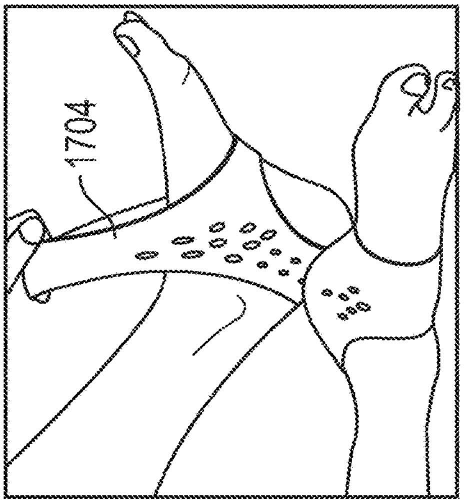
FIGS. 17A, 17B, and 17C show an example of portions of wearable "heel cup" transducer housings, and portions of a patient's heel that can be included in an environment in which the wearable transducer housings can be used as part of the system.
Figure 17C:
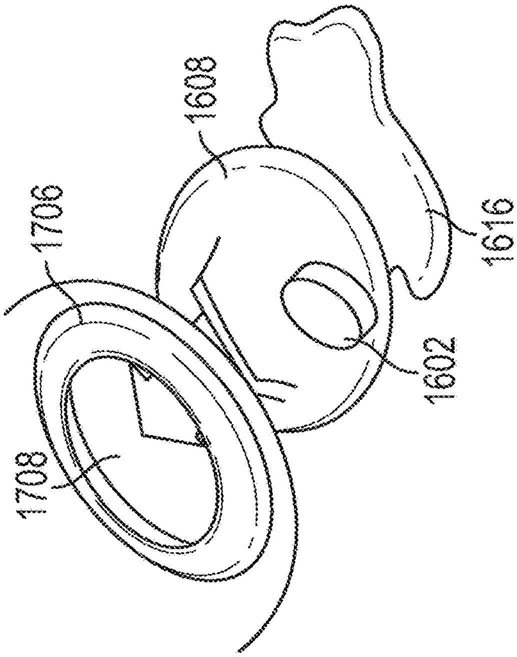
Figure 17A:
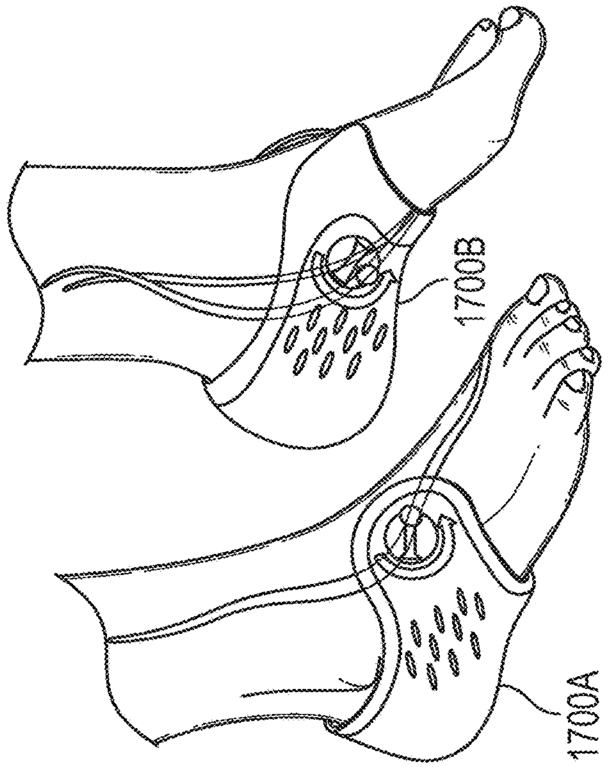

FIGS. 17A, 17B, and 17C show an example of portions of wearable "heel cup" transducer housings 1700A-B, and portions of a patient's heel that can be included in an environment in which the wearable transducer housings 1700A-B can be used as part of the system 100. The wearable "heel cup" transducer housings 1700A-B can include a silicone material or other conformable wearable portion that can be fitted under a heel of the patient, such as with one or more wings, tabs, lobes, or wrap-around portions that can extend partially or fully along the sides of the patient's foot, over the top of the patient's foot, or both. In this way, the transducers 402 can be located near the patient's ankle, such as at a similar location to that shown in FIGS. 16A, 16B, and 16C, near the desired target blood vessel of interest, without requiring adhesion of the heel cup wearable to the patient. Similar mechanisms to those shown in FIGS. 16A-C for allowing end-user movement of the transducers 402 can be employed in the example of FIGS. 17A-C, such as shown in FIG. 17C. In FIG. 17C, a rotatable transducer carrier 1608 can be placed within a receptacle 1708 that can be embedded or otherwise included in the heel cup wearable transducer housing 1700A-B, such as to allow end-user movement of the transducer or transducers 402, 1602. The rotatable transducer carrier 1608 can include a sealed gel-pack, such as for carrying acoustic couplant gel, as explained herein. The sealed gel-pack "pillow" can be end-user removable, end-user attachable, or both, such as to allow exchange of the gel-pack pillow between uses. A stretchable wrap-around strap 1704 can be extended across the top of the foot of the patient, such as shown in FIG. 17B, and secured to another wearable portion of the heel cup transducer housings 1700A-B. This can help hold the heel cup wearable in place with the transducers 402, 1602 properly and stably located in a desired manner near a target region of interest. The silicone material of the wearable transducer housings 1700A-B can include perforations in the silicone material, such as shown in FIGS. 17A, 17B, such as to help provide additional elasticity for helping during stretching the strap 1704 or other desired portion of the wearable transducer housings 1700A-B.

Figure 18B:
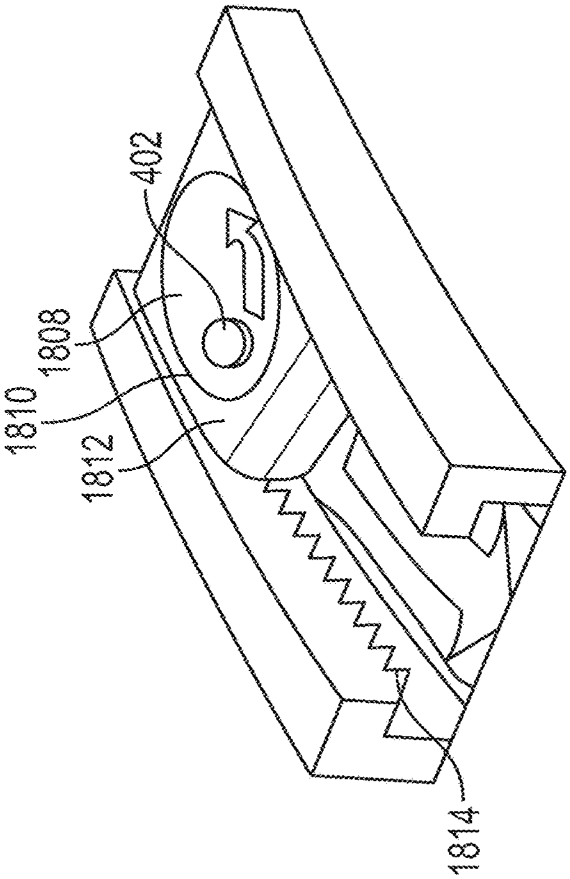
FIGS. 18A, 18B show an example of portions of wearable "instep brace" carriers, and portions of a patient's feet that can be included in an environment in which the wearable carriers can be used as part of the system.
Figure 18A:
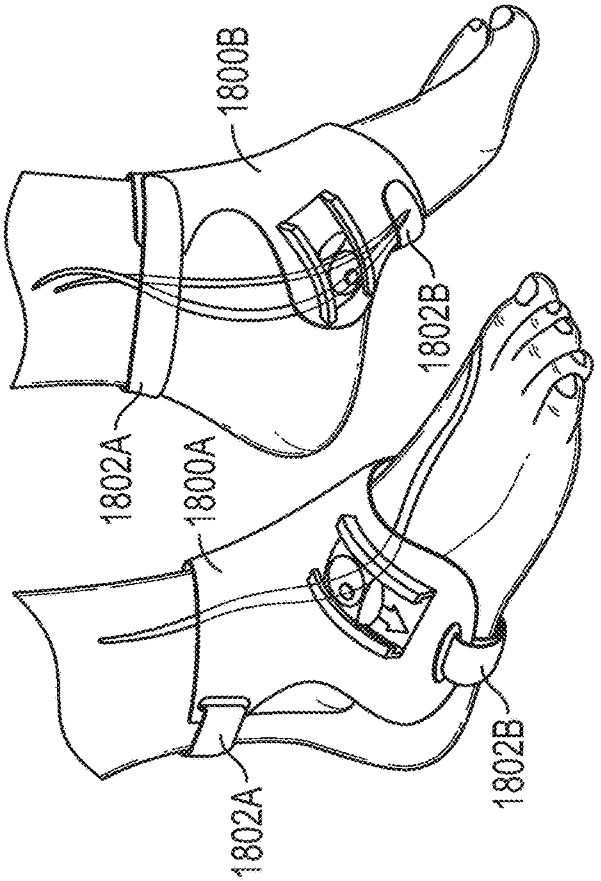

FIGS. 18A, 18B show an example of portions of wearable "instep brace" carriers 1800A-B, and portions of a patient's feet that can be included in an environment in which the wearable carriers 1800A-B can be used as part of the system 100. The wearable "instep brace" carriers 1800A-B can include a silicone material or other conformable wearable portion that can be fitted against a top instep portion of a foot of the patient, such as with straps 1802 that can extend about the patient's leg or under the patient's foot to secure the instep brace carriers 1800A-B at their desired locations. The instep brace carriers 1800A-B can carry respective arrangements of one or more transducers 402, such as which can be located near the patient's ankle, such as at a similar location to that shown in FIGS. 16A, 16B, and 16C, near the desired target blood vessel of interest, without requiring adhesion of the instep braces 1800A-B wearable to the patient. Similar mechanisms to those shown in FIGS. 16A-C for allowing end-user movement of the transducers 402 can be employed in the example of FIGS. 18A, 18B. In FIG. 18B, a rotatable transducer carrier 1808 can be placed within a receptacle 1810 in an indexed or other sliding shuttle 1812 that can translate along or within an indexed or other track 1814. By providing both rotation and translation capabilities for the arrangement of one or more transducers 402, more flexibility can be provided in positioning such transducers 402 with respect to a desired target region of interest. Such combined rotation and translation capability can also be applied to the other configurations described herein. The rotatable transducer carrier 1808 can include a sealed gel-pack, such as for carrying acoustic couplant gel, as explained herein. The sealed gel-pack "pillow" can be end-user removable, end-user attachable, or both, such as to allow exchange of the gel-pack pillow between uses.

Figure 19B:
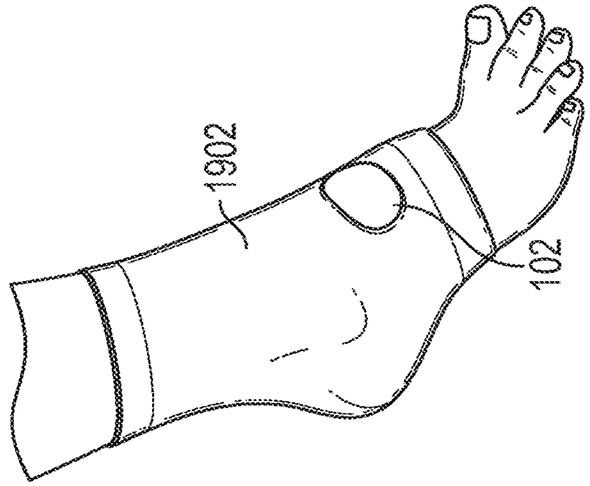
FIGS. 19A, 19B, and 19C show an example of a similar arrangement to that shown and described with respect to FIGS. 18A, 18B, but with the addition of a "stretch sock."
Figure 19C:
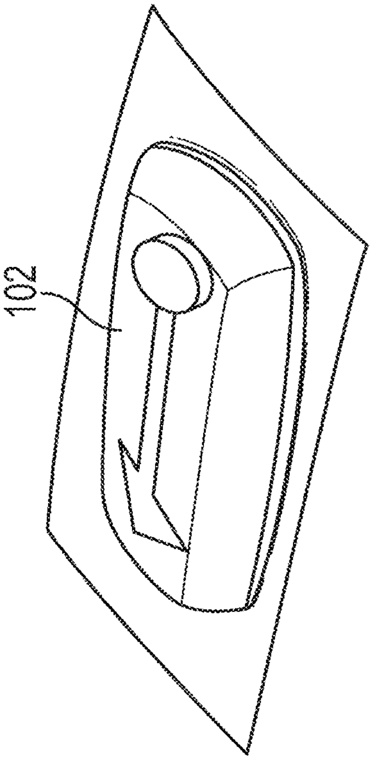
Figure 19A:
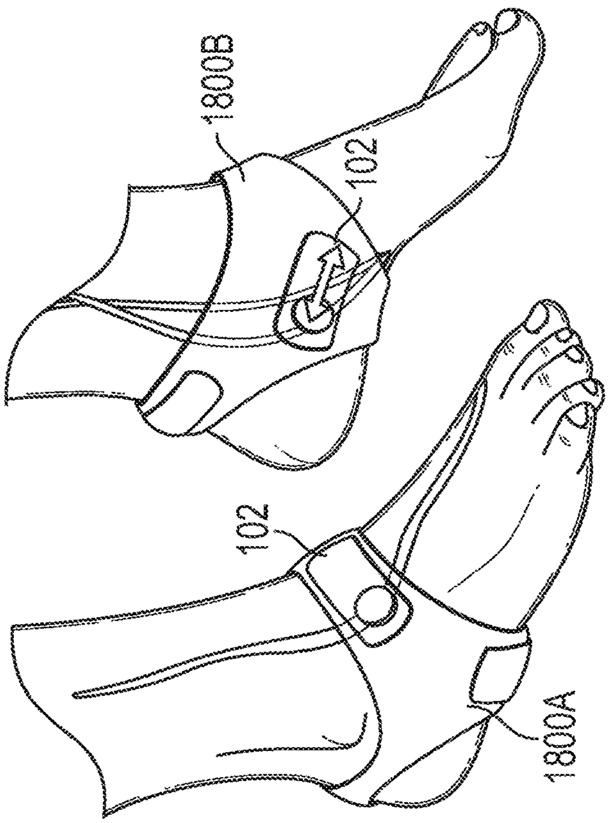

FIGS. 19A, 19B, and 19C show an example of a similar arrangement to that shown and described with respect to FIGS. 18A, 18B, but with the addition of a "stretch sock" 1902 that can be worn over a transducer carrier carrying one or more transducers 402 such as to help secure the transducers 402 at a desired location with respect to a target region of the patient.

Figure 20:
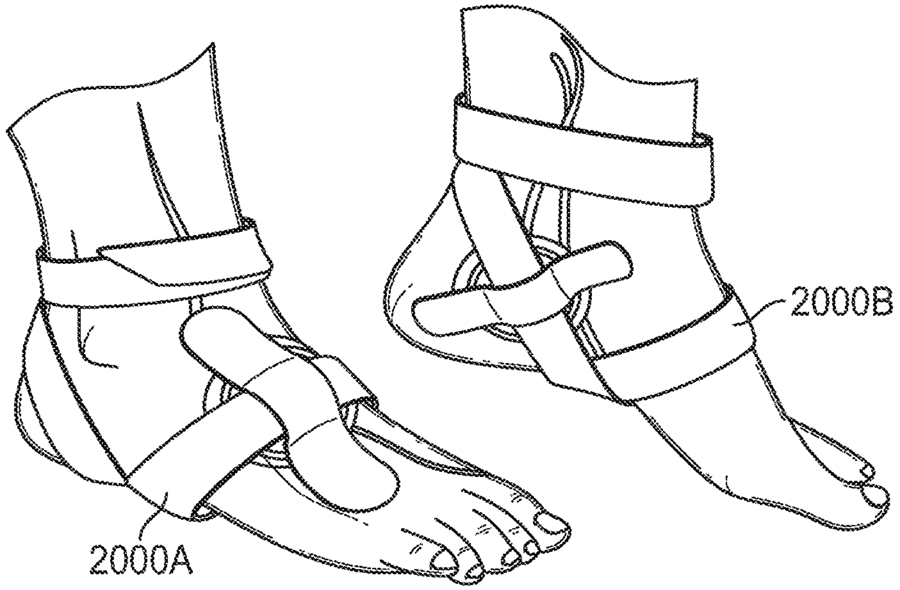
FIG. 20 shows an example of a single strap arrangement that can be wound around the leg, heel, and foot as shown to secure a rotatable and/or translatable transducer carrier at a desired location against the subject.

FIG. 20 shows an example of a single strap arrangement 2000 that can be wound around the leg, heel, and foot as shown to secure a rotatable and/or translatable transducer carrier at a desired location against the subject.

Figure 21B:
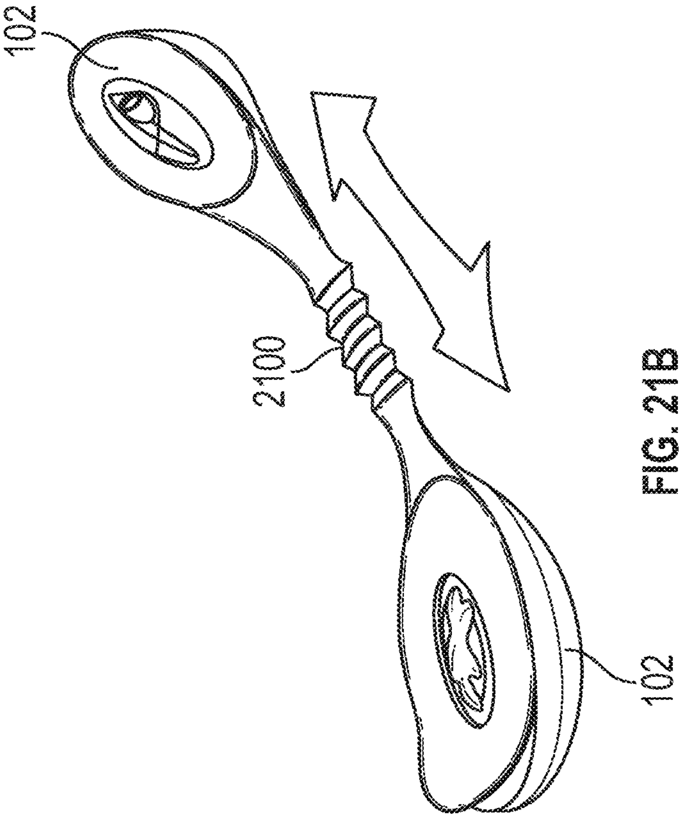
FIG. 21A, 21B shows an example of a flexible bridge transducer carrier, such as which can include one or more transducer carriers that can adhesively be secured at a desired location on a foot of the subject, with an accordion-style or other articulating bridge that can be located over and across a top of the patient's foot.
Figure 21A:
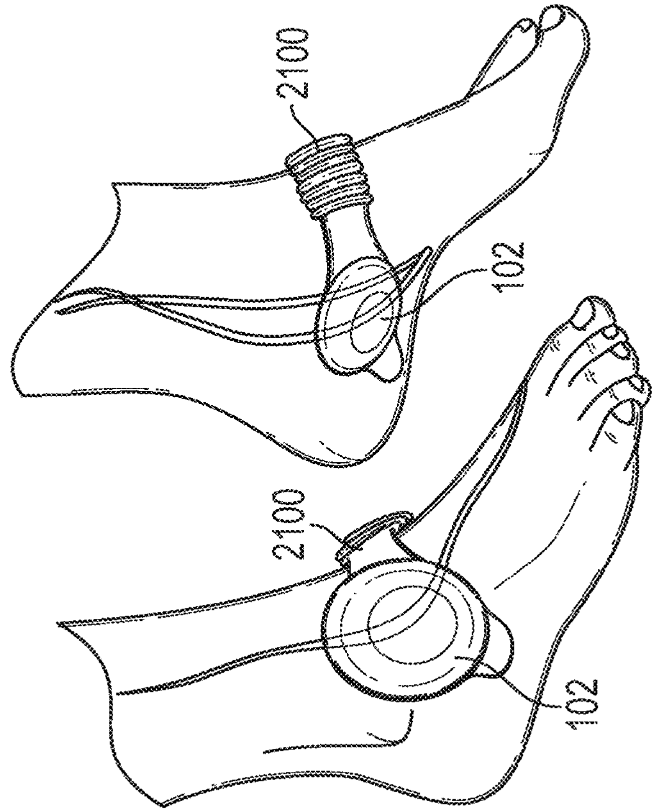

FIG. 21A, 21B shows an example of a flexible bridge wearable 2100, such as which can include one or more transducer carriers 102 that can adhesively be secured at a desired location on afoot of the subject, with an accordion-style or other articulating bridge that can be located over and across a top of the patient's foot.

Artificial Intelligence or Machine Learning Example

The system 100 may include control and signal processing and other functionality, portions of which can be implemented in analog or digital hardware, firmware, or software performing instructions using processor 112 or controller 308 circuitry. The software may employ one or more deterministic algorithms. The software may additionally or alternatively employ artificial intelligence or machine learning, such as which include training a statistical learning model and then using the trained statistical learning model in an inference mode.

Figure 22:
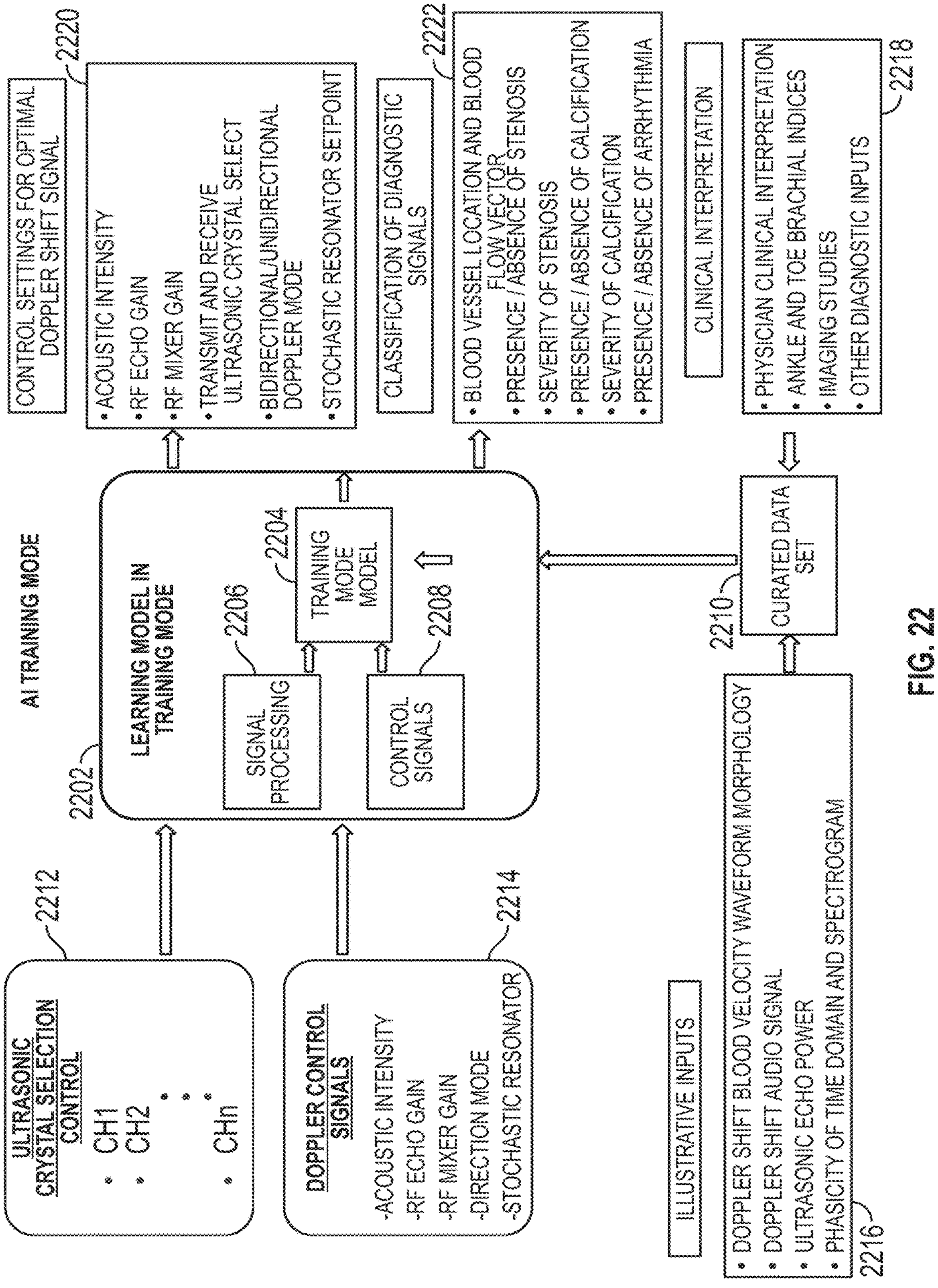
FIG. 22 is a block diagram showing portions of a technique for training an AI statistical learning model.

FIG. 22 is a block diagram showing portions of a technique for training an AI statistical learning model, such as which can be included in or coupled to the system 100 using the processor 112 or the controller 308 circuitry. A statistical learning model 2202 can include a training mode engine 2204, such as which can receive signal processing inputs 2206 and control signal inputs 2208, as well as inputs from a curated data set 2210 that can be stored in a database in memory circuitry that can be included or coupled to the processor 112 or the controller 308 circuitry. The learning model 2202 can also include inputs from the electronics unit of the carrier 102, such as ultrasonic crystal transducer 402 selection control componentry 2212 (e.g., for selecting individual ones of "n" channels, CH1, CH2, . . . CHn), or Doppler control signals 2214 (e.g., acoustic intensity, RF echo gain, RF mixer gain, direction mode, stochastic resonator settings).

For example, an acoustic intensity parameter can be specified to establish or adjust a drive signal level of an insonating piezoelectric transducer 402. An RF echo gain parameter can be specified to establish or adjust a gain setting of the impedance matching RF amplifier 414 to which a receive mode piezoelectric transducer is connected for receiving a response-to-insonation signal from the target region. An RF mixer gain can be specified to establish or adjust a gain setting of one or both of the mixers 1106A-B. A direction mode can be specified to establish or adjust a flow direction setting such as which can be toggled between forward flow and reverse flow. The stochastic resonator settings can be specified to establish or adjust one or more of the intensity or bandwidth of injected SR signal from the audio response signal injection circuit 418.

The curated data set 2210 can include system operation training inputs 2216 such as: Doppler shift blood velocity waveform morphology, Doppler shift audio signal, ultrasonic echo power, phasicity of the time domain Doppler shift signal and/or the spectrogram. The curated data set 2210 can also include other training inputs, such as clinical interpretation inputs 2218, such as a physician clinical interpretation of the Doppler shifted audio signal, ankle and/or toe brachial indices, imaging studies, or other diagnostic inputs.

The learning model 2202 can be trained using ground-truth training data. Such ground-truth training data can include the curated data set 2210, which can be formed using one or both of the system operation training inputs 2216 or the clinical interpretation data inputs 2218. The trained learning model can be trained such as to provide recommended or optimized output Doppler shift control signals 2220 (e.g., acoustic intensity, RF echo gain, RF mixer gain, direction mode, stochastic resonator settings), such as which can be based primarily or solely on the system operation training inputs 2216, but which can optionally also include aspects from the clinical interpretation data inputs 2218. Additionally or alternatively, the learning model 2202 can be trained, using ground truth training data, such as to provide classification 2222 of diagnostic signals (e.g., blood vessel location and blood flow vector, presence or absence of stenosis, severity of stenosis, presence or absence of calcification, severity of calcification, presence/absence of arrhythmia), such as which can be based primarily or solely on the clinical interpretation data inputs 2218, but which can optionally also include aspects from the system operation data inputs 2216.

Figure 23:
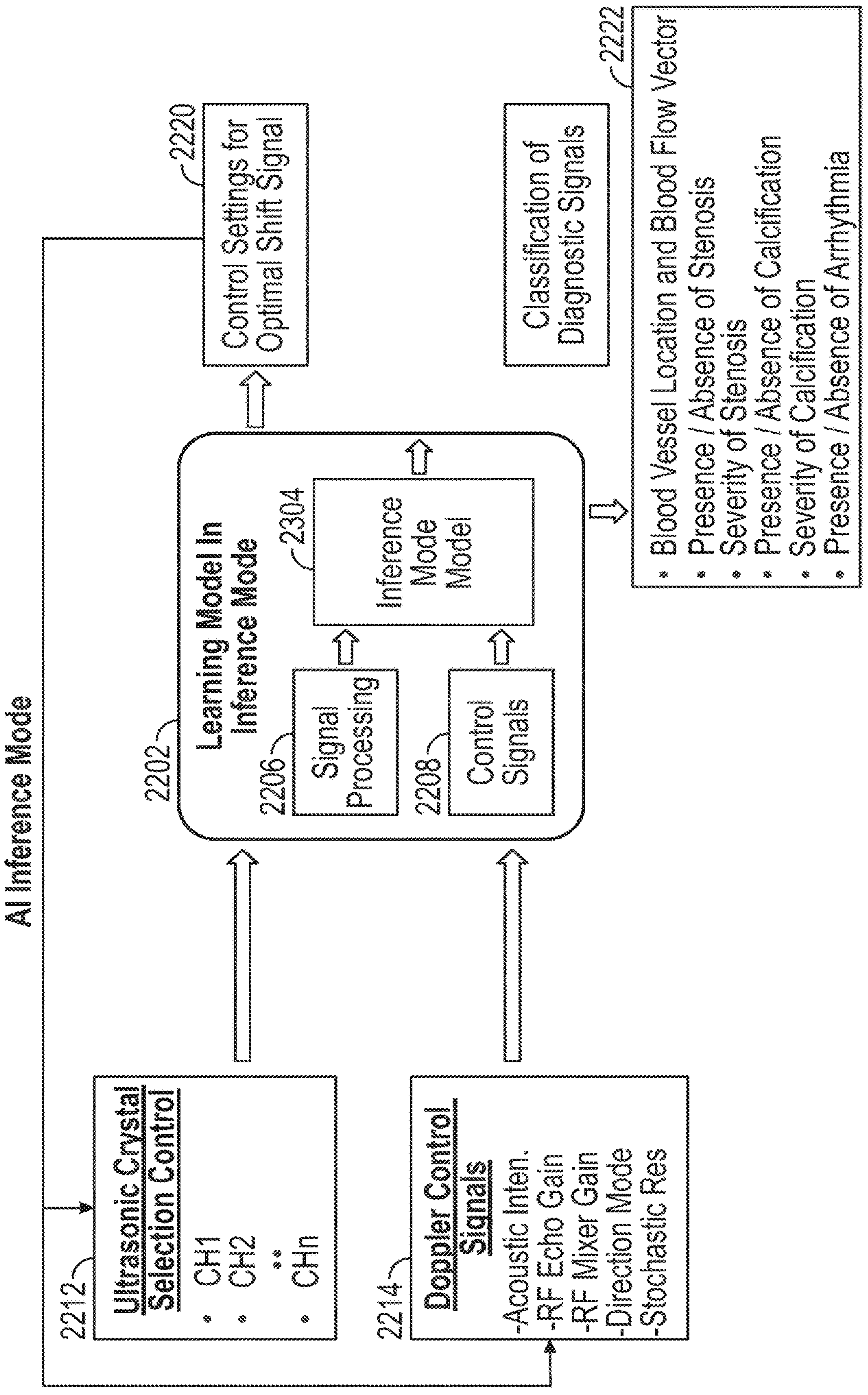
FIG. 23 shows the arrangement of the example of FIG. 22, in which the learning model has been trained into an inference mode learning model, such as for use at run-time in an inference-mode.

FIG. 23 shows the arrangement of the example of FIG. 22, in which the learning model 2204 has been trained into an inference mode learning model 2304, such as for use at run-time in an inference-mode. For example, the trained inference mode learning model 2304 in inference mode can be used to select system operation parameter control settings 2220, such as for helping to obtain a suitable or even "optimal" set of system operation parameter control settings, such as can be used with selection control componentry 2212 for selecting individual ones of "n" channels, CH1, CH2, . . . CHn), or Doppler control signals 2214 (e.g., acoustic intensity, RF echo gain, RF mixer gain, direction mode, stochastic resonator settings. Additionally or alternatively, the trained inference mode learning model 2304 can be used for classification of diagnostic signals 2222.

Figure 24:
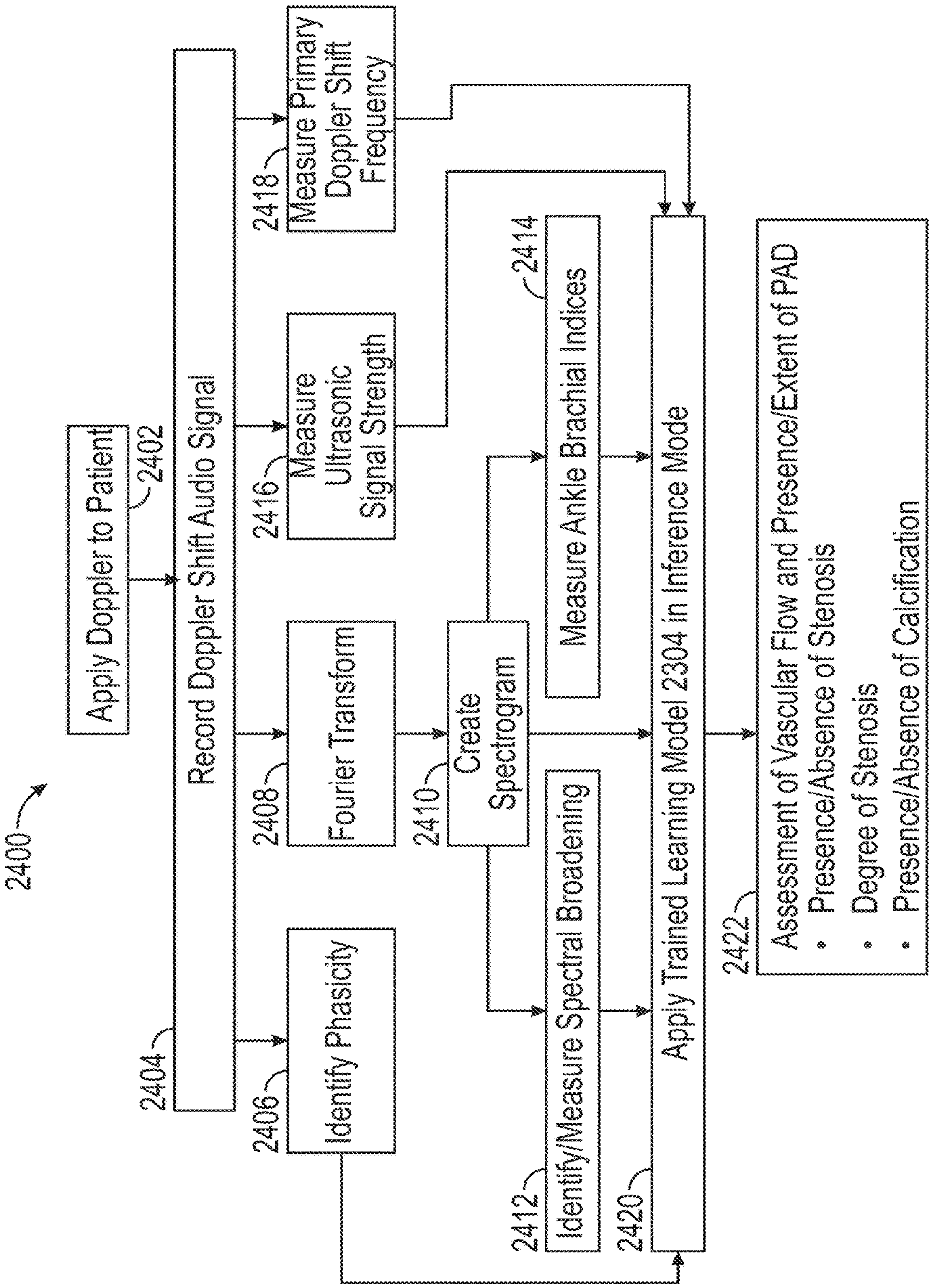
FIG. 24 is a flow chart showing an example of portions of a method for using the trained inference mode learning model in an inference mode for classification of diagnostic signals.

FIG. 24 is a flow chart showing an example of portions of a method 2400 for using the trained inference mode learning model 2304 in an inference mode for classification of diagnostic signals 2222. At 2402, a selected set of system operation parameter control settings 2220 can be used to apply Doppler insonation to the patient, such as using a first transducer 402 in a transmit mode, and to receive the RF echo response signal, such as using a different second transducer 402 in a receive mode.

At 2404, a resulting Doppler shifted audio signal can be obtained, such as described herein, and recorded in memory circuitry of the system 100. Using this resulting recorded Doppler-shifted audio signal, various signal-processing and analysis techniques can be applied.

At 2406, for example, phase information such as a phasicity can be identified. For a given insonation and response, the time-domain Doppler-shifted audio response signal can manifest one of various different possible phasicities, such as monophasic, biphasic, or triphasic. A monophasic Doppler-shifted audio response signal can include an amplitude increase followed by an amplitude decrease, where the amplitude crossing is not followed by another amplitude increase. A biphasic Doppler-shifted audio response signal can include an amplitude increase followed by an amplitude decrease, which is again followed by another amplitude increase followed by another amplitude decrease. A triphasic Doppler-shifted audio response signal can include an amplitude increase followed by an amplitude decrease, which is again followed by another amplitude increase followed by another amplitude decrease, and that include multiple zero-crossings, a further amplitude oscillation (increase and decrease), or both. The type of phasicity, degree of phasicity, or other characteristic of the phasicity can be identified and provided to the trained learning model 2304, such as during operation at run-time in inference mode.

At 2408, for example, an FFT or other Fourier transform can additionally or alternatively be performed on the recorded time-domain Doppler-shifted audio signal to obtain a resulting frequency-domain representation of the recorded time-domain Doppler-shifted audio signal.

At 2410, a spectrogram can be created using the frequency-domain representation of the recorded time-domain Doppler-shifted audio signal. The spectrogram can be one or more of recorded, displayed (e.g., using the display 106), or further processed (e.g., using the processor 112). The spectrogram can provide a visual way of representing the signal strength or signal intensity of a signal over time at various different frequencies that are present in the frequency-domain representation of the recorded time-domain Doppler-shifted audio signal. The spectrogram can also be provided to the trained learning model 2304, such as during operation at run-time in inference mode.

At 2412, using the spectrogram, using the frequency-domain representation of the recorded time-domain Doppler-shifted audio signal, or both, a "spectral broadening" can be identified, measured, or both. The presence of spectral broadening, the degree of spectral broadening, or both can be provided to the trained learning model 2304, such as during operation at run-time in inference mode.

Spectral broadening of the Doppler-shifted audio signal can occur when blood flow transitions from laminar to more turbulent, such as in the presence of stenosis in a blood vessel. When such turbulent flow occurs, there is a wider spectrum of frequencies in the Doppler-shifted audio signal due to a wider distribution of velocities of blood flow. The wider spectrum of frequencies in the Doppler-shifted audio signal is exhibited as a "thickening" or more "dense" spectrogram or spectral analysis waveform representing amplitude (y-axis) against frequency (x-axis). The degree of stenosis can be evaluated based on the degree of spectral broadening that is observed in the spectrogram.

The degree of spectral broadening can be determined from a continuous-wave Doppler-shifted audio signal using the frequency domain spectrogram. This degree of spectral broadening can be represented as a Spectral Broadening Index (SBI). The SBI can be used as a proxy to represent a degree of stenosis of the vessel. The SBI can be determined from the amplitude vs. frequency data as follows:

$$SBI=(F_{max}-F_{mean})/F_{max}\times 100=100-F_{mean}/F_{max}\times 100.$$

In the above equation, $F_{max}$ is the frequency in the spectrogram at which the maximum amplitude signal is observed, $F_{mean}$ is the frequency in the spectrogram at which the average or mean amplitude signal is observed. The SBI can be used in training a statistical learning model, or at run-time at which the trained statistical learning model is being used in inference mode.

At 2414, using one or more of the spectrogram, the time-domain Doppler-shifted audio signal, or the frequency domain representation of the time-domain Doppler-shifted audio signal, one or more Ankle Brachial Indexes (ABIs) can be measured or otherwise determined. The ABIs can be one or more of recorded, displayed (e.g., using the display 106), or further processed (e.g., using the processor 112), or provided to the trained learning model 2304 operating in inference mode.

At 2416, an ultrasonic signal strength can be measured or otherwise determined, such as can include using amplitude information from the time-domain Doppler-shifted audio signal. One or more indications of the resulting signal strength can be recorded, displayed (e.g., using the display 106), or further processed (e.g., using the processor 112), or provided to the trained learning model 2304 operating in inference mode.

At 2418, a primary Doppler-shift frequency can be identified, measured, or both, such as from the recorded time-domain Doppler-shifted audio signal, from its frequency-domain representation or both. This primary Doppler-shift frequency information can be one or more of recorded, displayed (e.g., using the display 106), or further processed (e.g., using the processor 112), or provided to the trained learning model 2304 operating in inference mode. This primary Doppler-shift frequency information can be useful for determining one or more blood flow characteristics, either or any of which can be provide to the trained learning model 2304 operating in inference mode, such as for providing one or more classifications of diagnostic signals at 222, for selecting one or more control settings for system operating parameters at 2220, or both.

At 2420, the trained learning model 2304 operating at run-time in inference mode can be applied, such as for selecting one or more control settings for system operating parameters at 2220, or both.

At 2422, the trained learning model 2304 operating at run-time in inference mode can be used to provide an assessment of vascular flow and the presence or extent of PAD, such as can be one or more of recorded, displayed (e.g., using the display 106), or further processed (e.g., using the processor 112). Examples of useful information that can be provided using the assistance of the trained learning model 2304 operating at run-time in inference mode can include, among other things one or more of: (1) presence or absence of vessel stenosis; (2) degree of vessel stenosis; or presence or absence of calcification.

Because the trained learning model 2304 can include multiple inputs along different dimensions, as shown in FIG. 24, the trained learning model 2304 can provide better inferences at run-time, such as for a patient for which useful diagnostic information spans such multiple inputs along multiple dimensions. For example, by receiving ABIs at 2414 and flow velocity information from the determined primary Doppler-shift frequency at 2418 and/or from the spectrogram at 2410, the trained learning model 2304 can better identify the presence or one or more characteristics of the disease state in a patient with a near normal ABI, but with an altered flow velocity waveform pattern. This can help reduce false negatives in PAD diagnosis or assessment.

Figure 25:
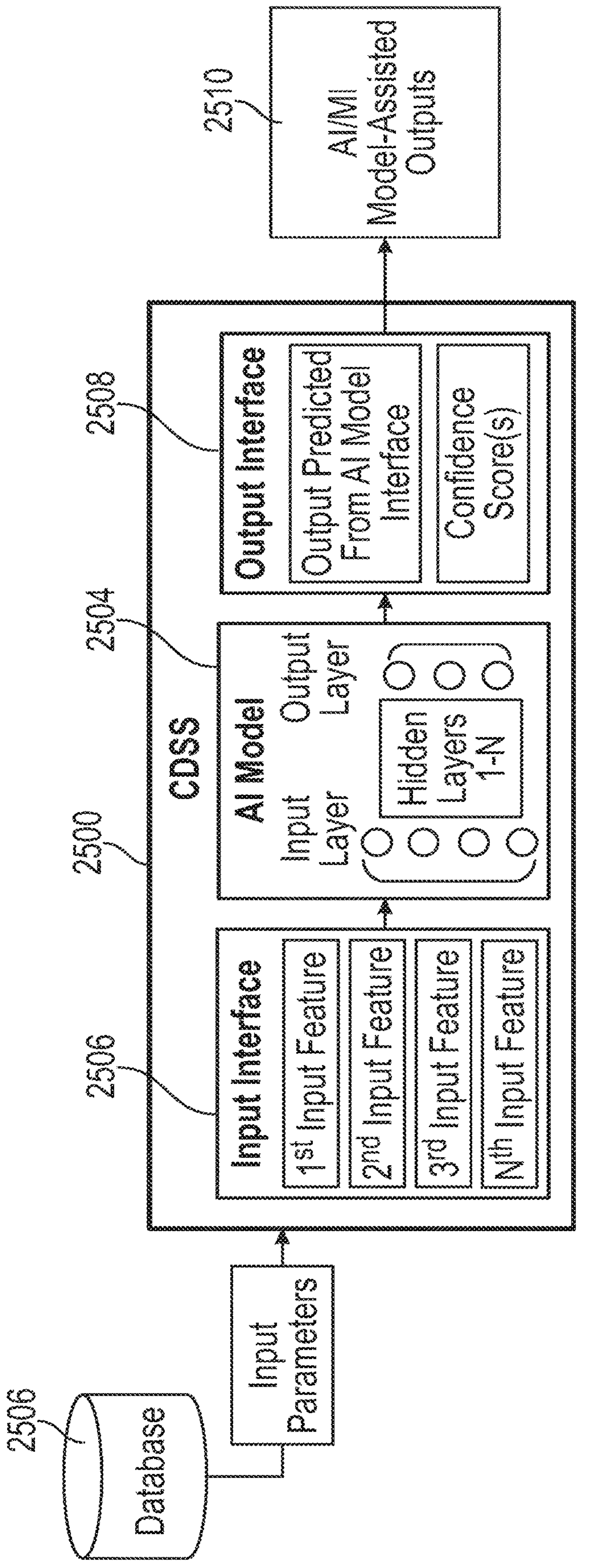
FIG. 25 is a block diagram of an example of an apparatus, device, or machine upon which any one or more of the AI/ML or other techniques (e.g., methodologies) discussed herein may be performed.

FIG. 25 is a block diagram of an example of an apparatus, device, or machine 2500 upon which any one or more of the AI/ML or other techniques (e.g., methodologies) discussed herein may be performed. FIG. 25 shows a schematic diagram of an example of portions of a computer-based clinical decision support system (CDSS) 2500, which can be included in or used as an adjunct to other portions of the system 100 described herein, such as the processor 112, the controller 308, or both. The CDSS can be configured to use the trained inference mode model 2304 to generate one or more system operational control settings 2220 or diagnostic classifications 2222, such as described herein. The CDSS can include an input interface 2506 through which the input features described with respect to FIGS. 22-24 can be provide as inputs to the learning model 2204, 2304, 2504. This can include input features that can be patient specific. The learning model 2204, 2304, can employ one or more of these input features to, at run-time in inference mode, an inference operation in which the one or more input features can be applied to the model to generate the model-assisted outputs 2510, which can be communicated to a user or to a device configured to serve as a proxy for such user or for other purposes.

The input interface 2506 can include a direct data link between the CDSS 2500 and one or more medical devices, such as the system 100, that generate at least some of the input features. For example, the input interface 2506 may transmit one or more input features, such as described herein, directly to the CDSS 2500 during a medical procedure. Additionally, or alternatively, the input interface 2506 may include a user interface, such as the user interface 104, to facilitate interaction between a user and the CDSS 2500 For example, the input interface 2500 may facilitate a user interface 104 through which the user may manually enter one or more of the input features described herein. Additionally, or alternatively, the input interface 2506 may provide the CDSS 2500 with access to an electronic patient record, such as from a database 2506, from which one or more input features may be extracted.

Based on one or more of the above input features, the processor 112 can operate at run-time in an inference mode such as to perform an inference operation using the AI model 2504 to generate one or more model-assisted outputs 2510. For example, input interface 2506 may deliver the one or more input features into an input layer of the AI model 2504 that can propagate the one or more input features through the AI model 2504 to an output layer. The AI model 2504 can provide a computer or other system with the ability to perform tasks, without requiring explicitly being programmed, by making inferences based on patterns found in the analysis of data. For example, the AI model 2504 can explore the study or construction of one or more algorithms (e.g., machine-learning algorithms) that may learn from existing data and make predictions about new data. Such ML algorithms can operate by building an AI model 2504 from ground-truth or other training data in order to make data-driven predictions or decisions that can be expressed as outputs or assessments.

The system 100 can employ one or more of supervised ML or unsupervised ML. Supervised ML can use prior knowledge (e.g., examples that correlate inputs to outputs or outcomes) to learn the relationships between the inputs and the outputs. A goal of supervised ML can be to learn a function that, given some training data, such as described herein, best approximates the relationship between the training inputs and outputs so that the ML model can implement similar relationships when given inputs to generate the corresponding outputs. Unsupervised ML can include training of an ML algorithm using information that is neither classified nor labeled, and can allow the ML algorithm to act on that information without guidance. Unsupervised ML can be particularly useful in exploratory analysis because it can automatically identify structure in data. Unsupervised learning can include one or more generative learning techniques, such as Generative Adversarial Networks (GAN) or the like.

For example, certain tasks suitable for supervised ML can include classification problems and regression problems. Classification problems ca also be referred to as categorization problems. Classification problems can aim at classifying items into one of several category values (for example, is this object an apple or an orange?). Regression algorithms can aim at quantifying some items (for example, by providing a score to the value of some input). Some examples of supervised-ML algorithms can include Logistic Regression (LR), Naive-Bayes, Random Forest (RF), neural networks (NN), deep neural networks (DNN), matrix factorization, and Support Vector Machines (SVM).

Some examples of tasks for unsupervised ML can include clustering, representation learning, and density estimation. Some examples of unsupervised-ML algorithms can include K-means clustering, principal component analysis, and autoencoders.

Another type of ML is federated learning (also referred to as collaborative learning). Federated learning can be used to help train an algorithm across multiple decentralized devices holding local data, without exchanging the data. This approach stands in contrast to a centralized machine-learning technique in which the local datasets are uploaded to one server, as well as to more decentralized approaches that can often assume that local data samples are identically distributed. Federated learning can help enables multiple actors to build a common, robust machine learning model without sharing data, thus allowing to address useful issues such as data privacy, data security, data access rights and access to heterogeneous data.

As explained herein, the AI model may be trained initially, continuously, or recurrently, such as before run-time performance of the inference operation by the processor 112. Then, during the inference operation, the patient specific input features provided to the AI model 2504 may be propagated, such as from an input layer, through one or more hidden layers, and ultimately to an output layer that corresponds to the AI/ML model-assisted outputs.

During or after the inference operation, one or more of the model-assisted outputs 2510 can be one or more of recorded, further processed, or communicated to the user, such as via the user interface (UI) 104, or can automatically cause the system 100 to perform a desired action, such as described herein.

The above description includes references to the accompanying drawings, which form apart of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or device-readable or machine-readable storage medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An ultrasound transducer assembly, including:

a unitary transducer carrier, including a first surface defining a first X-Y plane defining an X direction and a Y direction that is orthogonal to the X direction, and defining a Z direction that is orthogonal to the X-Y plane, the first surface configured to face toward a living subject to which the unitary transducer carrier is to be affixed to insonify the subject, the unitary transducer carrier including a second surface, generally opposing and offset in the Z direction from the first surface, the unitary transducer carrier including a plurality of transducer receptacles to carry respective ultrasound transducers; and wherein first and second ones of the ultrasound transducers are arranged for being used together to define an insonation region in the subject are located in respective transducer receptacles on the same unitary transducer carrier and oriented to define respective first and second axes through the first surface and into the subject at different angles from each other with respect to the first surface such that the respective first axis and the second axis intersect each other to define the insonation region.

2. The ultrasound transducer assembly of claim 1, the plurality of transducer receptacles arranged comprising:

individual ones of the receptacles being sized and shaped to accommodate corresponding individual ones of the ultrasound transducers, and respectively including at least a partial perimeter surface sized and shaped to be seated against a sidewall of the ultrasound transducer to provide a specified positioning alignment feature between an individual one of the receptacles and a corresponding individual one of the ultrasound transducers.

3. The ultrasound transducer assembly of claim 2, in which the individual one of the receptacles includes a corresponding recess in the unitary transducer carrier sized and shaped to receive a subject-facing side of the corresponding ultrasound transducer.

4. The ultrasound transducer assembly of claim 3, in which individual ones of the plurality of receptacles respectively include the corresponding recess having the partial perimeter shaped to provide an adjacent cutout to allow electrical lead access to a subject-facing electrode on a corresponding one of the ultrasound transducers that is located in the corresponding recess.

5. The ultrasound transducer assembly of claim 1, including a recess or channel located between adjacent individual ones of the plurality of receptacles to provide an acoustic barrier between the adjacent individual ones of the plurality of receptacles.

6. The ultrasound transducer assembly of claim 1, wherein individual ones of the plurality of receptacles respectively include an elongate receptacle sized and shaped to receive an elongate ultrasound transducer.

7. The ultrasound transducer assembly of claim 1, wherein the unitary transducer carrier is a wearable carrier, configured to be wearably affixed to a target location on a limb of the subject, and further including:

the first transducer, carried by the unitary transducer carrier using a first individual receptacle of the plurality of receptacles, the first transducer having a first location and having a first orientation in the Z direction, forming a first angle that is orthogonal to the first surface;

the second transducer, carried by the carrier using a second individual receptacle of the plurality of receptacles, the second transducer having a second location that is offset from the first transducer in the X direction, and having a second orientation that forms a second angle that is oblique to the Z direction and intersects the first orientation to define a first depth region of interest at a first depth beneath the first surface; and a third transducer, carried by the unitary transducer carrier using a third individual receptacle of the plurality of receptacles, the third transducer having a third location that is further offset from the first transducer in the X direction than the second transducer, and having a third orientation that forms a third angle that is oblique to the Z direction, wherein the third angle is larger than the second angle and intersects the first orientation to form a second depth region of interest at a second depth beneath the first surface that is closer to the first surface than the first depth.

8. The ultrasound transducer assembly of claim 7, in combination with:

controller circuitry, configured to:

select a first pair of transducers, forming an acoustic transmitter and an acoustic receiver, from a set of transducers including the first transducer, the second transducer, and the third transducer, and control the acoustic transmitter for insonating the subject with a first insonation signal at a first insonation frequency, and control the acoustic receiver to determine a first signal characteristic at the first depth region of interest;

then select a second pair of transducers, forming an acoustic transmitter and an acoustic receiver, from the set of transducers including the first transducer, the second transducer, and the third transducer, and control the acousting transmitter for insonating the subject with a second insonation signal at a second insonation frequency that alike with or different from the first insonation frequency, and control the acoustic receiver to determine a second signal characteristic at the second depth region of interest; and analyze the first and second signal characteristics to select one of the first pair of transducers and the second pair of transducers for further use in measuring a blood flow characteristic of the subject.

9. The ultrasound transducer assembly of claim 7, in combination with a blood vessel patency measurement system for assessing peripheral arterial disease (PAD) of a subject without requiring using a handheld Doppler flowmeter probe, the system including:

an inflatable cuff, wearable on a limb of the subject;

a Pump, in fluid communication with the inflatable cuff to inflate the inflatable cuff;

a pressure sensor, in fluid communication with the inflatable cuff to measure an inflation pressure of the inflatable cuff; and a wearable acoustic Doppler blood flowmeter, wearable on the limb of the subject to avoid requiring using a handheld Doppler flowmeter probe, the flowmeter including the ultrasound transducer assembly.

10. The ultrasound transducer assembly of claim 7, wherein the first receptacle is oriented such that a face of the first transducer is parallel to the first surface, wherein the second receptacle is oriented such that a face of the second transducer forms an oblique angle with respect to the first surface to define the second angle, and wherein the third receptacle is oriented such that a face of the third transducer forms an oblique angle with respect to the first surface to define the third angle.

11. The ultrasound transducer assembly of claim 7, wherein the second angle is between 10 degrees and 20 degrees with respect to the first surface, and wherein the first depth is between 20 and 40 millimeters beneath the first surface, and wherein the third angle is between 25 degrees and 35 degrees with respect to the first surface, and wherein the second depth is between 5 and 15 millimeters beneath the first surface.

12. The ultrasound transducer assembly of claim 1, wherein the first ultrasound transducer is oriented parallel to the first surface to define the first axis that projects orthogonally from the first surface into the subject, and wherein the second ultrasound transducer is oriented non-parallel to the first surface to define the second axis that projects at an oblique angle to the first axis to intersect the first axis to define the insonation region at which the first axis intersects the second axis.

13. An acoustic transducer assembly for affixation to a living subject, the acoustic transducer assembly including:

a unitary transducer carrier, including a first surface defining a first X-Y plane defining an X direction and a Y direction that is orthogonal to the X direction, and defining a Z direction that is orthogonal to the X-Y plane, the first surface configured to face toward a living subject to which the unitary transducer carrier is to be affixed to insonify the subject, the unitary transducer carrier including a second surface, generally opposing and offset in the Z direction from the first surface, the unitary transducer carrier including a plurality of transducer locations to carry respective acoustic transducers;

an acoustic first transducer, carried by the unitary transducer carrier using a first receptacle at a first location of the plurality of transducer locations, the first transducer having a first axis in a first orientation in the Z direction, forming a first angle that is orthogonal to the first surface;

an acoustic second transducer, carried by the unitary transducer carrier using a second receptacle at a second location of the plurality of transducer locations, the second location being offset from the first location in the X direction, and having a second axis in a second orientation that forms a second angle that is oblique to the Z direction and that intersects the first axis in the first orientation to define a first depth region of interest at a first depth beneath the first surface; and an acoustic third transducer, carried by the unitary transducer carrier using a third receptacle at a third location of the plurality of locations, the third location being further offset from the first location in the X direction than the second location, and having a third axis in a third orientation that forms a third angle that is oblique to the Z direction, wherein the third angle is larger than the second angle and intersects the first axis in the first orientation to form a second depth region of interest at a second depth beneath the first surface that is closer to the first surface than the first depth.

14. The acoustic transducer assembly of claim 13, in combination with:

controller circuitry, configured to:

select a first pair of transducers, forming an acoustic transmitter and an acoustic receiver, from a set of transducers including the first transducer, the second transducer, and the third transducer, and control the acoustic transmitter for insonating the subject with a first insonation signal at a first insonation frequency, and control the acoustic receiver to determine a first signal characteristic at the first depth region of interest;

then select a second pair of transducers, forming an acoustic transmitter and an acoustic receiver, from the set of transducers including the first transducer, the second transducer, and the third transducer, and control the acousting transmitter for insonating the subject with a second insonation signal at a second insonation frequency that is alike with or different from the first insonation frequency, and control the acoustic receiver to determine a second signal characteristic at the second depth region of interest; and analyze the first and second signal characteristics to select one of the first pair of transducers and the second pair of transducers for further use in measuring a blood flow characteristic of the subject.

15. The acoustic transducer assembly of claim 14, in combination with a blood vessel patency measurement system for assessing peripheral arterial disease (PAD) of a subject without requiring using a handheld Doppler flowmeter probe, the system including:

an inflatable cuff, wearable on a limb of the subject;

a pump, in fluid communication with the inflatable cuff to inflate the inflatable cuff;

a pressure sensor, in fluid communication with the inflatable cuff to measure an inflation pressure of the inflatable cuff; and a wearable acoustic Doppler blood flowmeter, wearable on the limb of the subject to avoid requiring using a handheld Doppler flowmeter probe, the flowmeter including the acoustic transducer assembly.

16. The acoustic transducer assembly of claim 13, comprising:

an acoustic fourth transducer, carried by the unitary transducer carrier using a fourth receptacle at a fourth location of the plurality of transducer locations, the fourth location being aligned with and offset from the first location in the Y direction, the fourth transducer having a first orientation in the Z direction, forming a fourth orientation at fourth angle that is orthogonal to the first surface;

an acoustic fifth transducer, carried by the unitary transducer carrier using a fifth receptacle at a fifth location of the plurality of transducer locations, the fifth location being aligned with and offset from the second location in the Y direction, the fifth location being offset from the fourth location in the X direction, and having a fifth orientation that forms a fifth angle that is oblique to the Z direction and that intersects the fourth orientation to define a third depth region of interest at a third depth beneath the first surface; and an acoustic sixth transducer, carried by the unitary transducer carrier using a sixth receptacle at a sixth location of the plurality of locations, the sixth location being aligned with and offset from the third location in the Y direction, and further offset from the fourth location in the X direction than the fifth location, and having a sixth orientation that forms a sixth angle that is oblique to the Z direction, wherein the sixth angle is larger than the fifth angle and intersects the fourth orientation to form a fourth depth region of interest at a fourth depth beneath the first surface that is closer to the first surface than the third depth.

17. The acoustic transducer assembly of claim 16, wherein the transducers are elongate transducers, individual ones of the elongate transducers having a transducer length greater than a transducer width, with the transducer length oriented in the Y direction.

18. The acoustic transducer assembly of claim 16, wherein the fourth receptacle is oriented such that a face of the fourth transducer is parallel to the first surface, wherein the fifth receptacle is oriented such that a face of the fifth transducer forms an oblique angle with respect to the first surface to define the fifth angle, and wherein the sixth receptacle is oriented such that a face of the sixth transducer forms an oblique angle with respect to the first surface to define the sixth angle.

19. The acoustic transducer assembly of claim 13, wherein the transducers are elongate transducers, individual ones of the elongate transducers having a transducer length greater than a transducer width, with the transducer length oriented in the Y direction, and wherein at least two of the transducers are aligned in a row in the X direction and are offset from another one of transducers in both the X and Y directions.

20. The acoustic transducer assembly of claim 13, wherein the transducers are elongate transducers, individual ones of the elongate transducers having a transducer length greater than a transducer width, with the transducer length oriented in the Y direction, and wherein one of the transducers is offset from an adjacent one of transducers in both the X and Y directions.

21. The acoustic transducer assembly of claim 20, in which each transducer is separated from any adjacent transducer by a recess or channel in the unitary transducer carrier, the recess or channel located between adjacent individual ones of the transducers to provide an acoustic barrier between adjacent transducers.

22. The acoustic transducer assembly of claim 21, in which the unitary transducer carrier includes a plurality of transducer receptacles to carry respective acoustic transducers.

23. The acoustic transducer assembly of claim 13, comprising:

at least two rows of at least two transducers, each row extending in the Y direction and offset from each other in the X direction; and a further row of at least two transducers, extending in the Y direction and offset from the at least two rows in both the X direction and the Y direction.

24. The acoustic transducer assembly of claim 13, wherein the first receptacle is oriented such that a face of the first transducer is parallel to the first surface, wherein the second receptacle is oriented such that a face of the second transducer forms an oblique angle with respect to the first surface to define the second angle, and wherein the third receptacle is oriented such that a face of the third transducer forms an oblique angle with respect to the first surface to define the third angle.

25. The acoustic transducer assembly of claim 13, wherein the second angle is between 10 degrees and 20 degrees with respect to the first surface, and wherein the first depth is between 20 and 40 millimeters beneath the first surface, and wherein the third angle is between 25 degrees and 35 degrees with respect to the first surface, and wherein the second depth is between 5 and 15 millimeters beneath the first surface.

26. A blood vessel patency measurement system for assessing peripheral arterial disease (PAD) of a living subject without requiring using a handheld Doppler flowmeter probe, the system including:

an inflatable cuff, wearable on a limb of the subject;

a pump, in fluid communication with the inflatable cuff to inflate the inflatable cuff;

a pressure sensor, in fluid communication with the inflatable cuff to measure an inflation pressure of the inflatable cuff; and an acoustic Doppler blood flowmeter, configured to be affixable to a living subject to avoid requiring using a handheld Doppler flowmeter probe, the flowmeter including:

a unitary transducer carrier, including a first surface defining a first X-Y plane defining an X direction and a Y direction that is orthogonal to the X direction, and defining a Z direction that is orthogonal to the X-Y plane, the first surface configured to face toward a living subject to which the unitary transducer carrier is to be affixed to insonify the subject, the unitary transducer carrier including a second surface, generally opposing and offset in the Z direction from the first surface, the unitary transducer carrier including a plurality of transducer receptacles to carry respective ultrasound transducers;

controller circuitry, configured to:

select a first pair of transducers located on the unitary transducer carrier, forming an acoustic transmitter and an acoustic receiver, from a set of transducers including a first transducer, a second transducer, and a third transducer, and control the acoustic transmitter for insonating the subject with a first insonation signal at a first insonation frequency, and control the acoustic receiver to determine a first signal characteristic at a first depth region of interest;

then select a second pair of transducers located on the unitary transducer carrier, forming an acoustic transmitter and an acoustic receiver, from the set of transducers including the first transducer, the second transducer, and the third transducer, and control the acoustic transmitter for insonating the subject with a second insonation signal at a second insonation frequency that is alike with or different from the first insonation frequency, and control the acoustic receiver to determine a second signal characteristic at a second depth region of interest; and analyze the first and second signal characteristics to select one of the first pair of transducers and the second pair of transducers for further use in measuring a blood flow characteristic of the subject; and signal processing circuitry, configured to translate a transduced acoustic response signal from the insonation frequency to an audio response signal in an audio frequency range, such that the audio response signal includes Doppler-shift information corresponding to detected blood flow when blood flow is detected by the Doppler blood flowmeter.

27. The system of claim 26, wherein the transducers include:

an acoustic first transducer, carried by the unitary transducer carrier using a first receptacle at a first location of a plurality of transducer locations, the first transducer having a first axis in a first orientation in the Z direction, forming a first angle that is orthogonal to the first surface;

an acoustic second transducer, carried by the unitary transducer carrier using a second receptacle at a second location of the plurality of transducer locations, the second location being offset from the first location in the X direction, and having a second axis in a second orientation that forms a second angle that is oblique to the Z direction and that intersects the first axis in the first orientation to define a first depth region of interest at a first depth beneath the first surface; and an acoustic third transducer, carried by the unitary transducer carrier using a third receptacle at a third location of the plurality of locations, the third location being further offset from the first location in the X direction than the second location, and having a third axis in a third orientation that forms a third angle that is oblique to the Z direction, wherein the third angle is larger than the second angle and intersects the first axis in the first orientation to form a second depth region of interest at a second depth beneath the first surface that is closer to the first surface than the first depth.

* * * * *